(12) United States Patent
Sizemore et al.

(10) Patent No.: US 12,297,179 B2
(45) Date of Patent: May 13, 2025

(54) CRYSTALLINE AND SALT FORMS OF AN ORGANIC COMPOUND AND PHARMACEUTICAL COMPOSITIONS THEREOF

(71) Applicant: Servier Pharmaceuticals LLC, Boston, MA (US)

(72) Inventors: Jacob Sizemore, Dickinson, TX (US); Shijie Zhang, Nashua, NH (US)

(73) Assignee: Servier Pharmaceuticals LLC, Boston, MA (US)

( * ) Notice: Subject to any disclaimer, the term of this patent is extended or adjusted under 35 U.S.C. 154(b) by 997 days.

(21) Appl. No.: 17/416,910

(22) PCT Filed: Dec. 20, 2019

(86) PCT No.: PCT/US2019/067897
§ 371 (c)(1),
(2) Date: Jun. 21, 2021

(87) PCT Pub. No.: WO2020/132471
PCT Pub. Date: Jun. 25, 2020

(65) Prior Publication Data
US 2022/0055995 A1    Feb. 24, 2022

Related U.S. Application Data

(60) Provisional application No. 62/882,712, filed on Aug. 5, 2019, provisional application No. 62/791,571, filed on Jan. 11, 2019, provisional application No. 62/784,083, filed on Dec. 21, 2018.

(51) Int. Cl.
*C07D 249/18* (2006.01)

(52) U.S. Cl.
CPC ........ *C07D 249/18* (2013.01); *C07B 2200/13* (2013.01)

(58) Field of Classification Search
CPC .................................................... C07D 249/18
See application file for complete search history.

(56) References Cited

U.S. PATENT DOCUMENTS

| | | | |
|---|---|---|---|
| 9,630,932 B2 * | 4/2017 | Thunuguntla | A61K 31/454 |
| 9,937,155 B2 * | 4/2018 | Hosahalli | A61K 31/5377 |
| 10,080,740 B2 * | 9/2018 | Thunuguntla | A61K 31/5377 |
| 11,147,801 B2 | 10/2021 | Nellore et al. | |
| 11,717,512 B2 * | 8/2023 | Ulanet | A61P 35/00 |
| | | | 514/359 |
| 2018/0369206 A1 | 12/2018 | Nellore et al. | |
| 2019/0025313 A1 | 1/2019 | Si et al. | |
| 2019/0105304 A1 | 4/2019 | Thunuguntla et al. | |
| 2021/0088520 A1 | 3/2021 | Si et al. | |
| 2021/0113531 A1 | 4/2021 | Ulanet et al. | |
| 2023/0285364 A1 * | 9/2023 | Coco | A61K 31/7068 |
| 2023/0285365 A1 * | 9/2023 | Coco | A61K 31/475 |

FOREIGN PATENT DOCUMENTS

| | | | |
|---|---|---|---|
| CN | 102348689 A | 2/2012 | |
| CN | 103476770 A | 12/2013 | |
| CN | 103965133 A | 8/2014 | |
| EP | 3019482 B1 * | 8/2018 | ......... A61K 31/4192 |
| JP | 2007-015952 A | 1/2007 | |
| JP | 2012-520251 A | 9/2012 | |
| JP | 2012-520252 A | 9/2012 | |
| RU | 2374256 C2 | 11/2009 | |
| WO | 2001/24785 A2 | 4/2001 | |
| WO | 2010/102825 A1 | 9/2010 | |
| WO | 2014/128669 A2 | 8/2014 | |
| WO | 2018/077923 A1 | 5/2018 | |
| WO | 2018/197997 A1 | 11/2018 | |

OTHER PUBLICATIONS

Anderson et al., Latest Medicinal Chemistry vol. 2, Technomic Co., Ltd., Japan. Sep. 25, 1999, pp. 347-365.
International Search Report and Written Opinion for Application No. PCT/US2019/067897, dated Mar. 12, 2020, 12 pages.
Bastin et al., Salt Selection and Optimisation Procedures for Pharmaceutical New Chemical Entities. Org Proc Res Dev. 2000;4(5):427-435.
Caira, Crystalline Polymorphism of Organic Compounds. Topics in Curren Chemistry, Design of Organic Solids. 1998;198:163-208.
Morissette et al., High-throughput crystallization: polymorphs, salts, co-crystals and solvates of pharmaceutical solids. Adv Drug Deliv Rev. Feb. 23, 2004;56(3):275-300.

(Continued)

*Primary Examiner* — John S Kenyon
*Assistant Examiner* — Rehana Ismail
(74) *Attorney, Agent, or Firm* — McCarter & English, LLP; Wei Song

(57) ABSTRACT

Provided herein are various salts, including tris(hydroxymethyl)aminomethane salts and sodium salts, as well as various crystalline forms of the compound represented by the structural formula: Also provided are pharmaceutical compositions comprising these salts and crystalline forms, methods for their manufacture, and uses thereof for treating conditions, including but not limited to conditions that would benefit from inhibition of dihydroorotate dehydrogenase (DHODH).

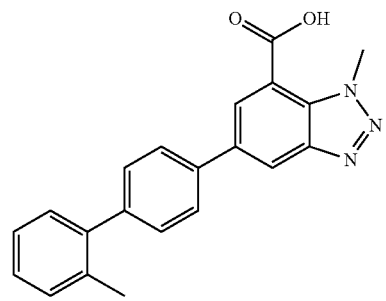

22 Claims, 18 Drawing Sheets

(56) References Cited

OTHER PUBLICATIONS

Serajuddin et al., Salt formation to improve drug solubility. Adv Drug Deliv Rev. Jul. 30, 2007;59(7):603-16.
Russian Office Action for Application No. 2021121387, dated Jul. 20, 2023, 34 pages.
Vyas et al., Recent developments in the medicinal chemistry and therapeutic potential of dihydroorotate dehydrogenase (DHODH) inhibitors. Mini Rev Med Chem. Oct. 2011;11(12):1039-55.

* cited by examiner

| Pos. [°2Th.] | Height [cts] | Rel. Int. [%] | Pos. [°2Th.] | Height [cts] | Rel. Int. [%] |
|---|---|---|---|---|---|
| 5.82 | 2657.38 | 100.00 | 21.87 | 173.92 | 6.54 |
| 8.15 | 1044.09 | 39.29 | 23.36 | 72.07 | 2.71 |
| 11.41 | 776.92 | 29.24 | 24.60 | 552.58 | 20.79 |
| 11.63 | 2098.91 | 78.98 | 24.94 | 591.59 | 22.26 |
| 12.82 | 1727.30 | 65.00 | 25.14 | 606.90 | 22.84 |
| 16.28 | 128.22 | 4.82 | 26.06 | 184.80 | 6.95 |
| 16.95 | 713.22 | 26.84 | 27.03 | 244.08 | 9.18 |
| 17.65 | 244.24 | 9.19 | 28.48 | 113.53 | 4.27 |
| 18.40 | 148.38 | 5.58 | 31.72 | 211.47 | 7.96 |
| 19.89 | 101.14 | 3.81 | | | |

| Pos. [°2Th.] | Height [cts] | Rel. Int. [%] | Pos. [°2Th.] | Height [cts] | Rel. Int. [%] |
|---|---|---|---|---|---|
| 6.49 | 4807.99 | 44.80 | 20.53 | 1306.06 | 12.17 |
| 8.51 | 1101.05 | 10.26 | 21.90 | 992.13 | 9.24 |
| 8.75 | 312.04 | 2.91 | 22.24 | 299.38 | 2.79 |
| 11.05 | 1029.62 | 9.59 | 22.88 | 589.68 | 5.49 |
| 11.40 | 1499.14 | 13.97 | 23.29 | 582.34 | 5.43 |
| 12.95 | 4275.39 | 39.83 | 24.31 | 496.63 | 4.63 |
| 13.11 | 3279.16 | 30.55 | 25.14 | 10732.88 | 100.00 |
| 13.55 | 186.33 | 1.74 | 25.90 | 1292.12 | 12.04 |
| 14.25 | 418.65 | 3.90 | 26.52 | 283.17 | 2.64 |
| 15.67 | 2641.11 | 24.61 | 27.26 | 470.11 | 4.38 |
| 16.09 | 746.95 | 6.96 | 28.14 | 407.36 | 3.80 |
| 16.61 | 797.39 | 7.43 | 28.85 | 884.16 | 8.24 |
| 17.26 | 1395.08 | 13.00 | 29.65 | 245.80 | 2.29 |
| 17.76 | 348.27 | 3.24 | 30.67 | 159.23 | 1.48 |
| 18.40 | 866.81 | 8.08 | 31.73 | 560.22 | 5.22 |
| 19.78 | 376.21 | 3.51 | 33.82 | 197.83 | 1.84 |
| 20.13 | 340.17 | 3.17 | 37.27 | 107.31 | 1.00 |

| Pos. [°2Th.] | Height [cts] | Rel. Int. [%] | Pos. [°2Th.] | Height [cts] | Rel. Int. [%] |
|---|---|---|---|---|---|
| 3.24 | 512.84 | 14.34 | 18.42 | 358.14 | 10.02 |
| 5.71 | 1479.25 | 41.38 | 18.96 | 138.85 | 3.88 |
| 10.40 | 69.12 | 1.93 | 23.01 | 49.75 | 1.39 |
| 11.41 | 1073.57 | 30.03 | 25.00 | 3575.12 | 100.00 |
| 12.84 | 291.72 | 8.16 | 27.04 | 140.08 | 3.92 |
| 16.22 | 182.57 | 5.11 | 27.51 | 225.28 | 6.30 |
| 17.37 | 343.09 | 9.60 | 31.72 | 180.45 | 5.05 |

| Pos. [°2Th.] | Height [cts] | Rel. Int. [%] | Pos. [°2Th.] | Height [cts] | Rel. Int. [%] |
|---|---|---|---|---|---|
| 5.94 | 1975.92 | 100.00 | 20.84 | 256.77 | 12.99 |
| 11.19 | 367.74 | 18.61 | 22.04 | 207.97 | 10.53 |
| 11.91 | 1732.79 | 87.70 | 22.50 | 289.63 | 14.66 |
| 12.68 | 269.42 | 13.64 | 22.70 | 208.76 | 10.57 |
| 13.44 | 219.79 | 11.12 | 23.28 | 335.86 | 17.00 |
| 14.33 | 120.63 | 6.10 | 24.56 | 220.11 | 11.14 |
| 15.25 | 38.87 | 1.97 | 25.16 | 92.77 | 4.70 |
| 17.07 | 548.61 | 27.76 | 26.11 | 137.27 | 6.95 |
| 17.88 | 117.30 | 5.94 | 27.04 | 78.96 | 4.00 |
| 18.77 | 198.29 | 10.04 | 31.70 | 163.25 | 8.26 |
| 19.66 | 224.20 | 11.35 | | | |

| Pos. [°2Th.] | Height [cts] | Rel. Int. [%] | Pos. [°2Th.] | Height [cts] | Rel. Int. [%] |
|---|---|---|---|---|---|
| 4.37 | 6718.72 | 100.00 | 25.51 | 684.19 | 10.18 |
| 8.68 | 483.82 | 7.20 | 26.24 | 303.01 | 4.51 |
| 11.48 | 712.75 | 10.61 | 27.00 | 203.44 | 3.03 |
| 13.93 | 131.56 | 1.96 | 27.69 | 141.84 | 2.11 |
| 15.23 | 385.00 | 5.73 | 28.04 | 244.92 | 3.65 |
| 15.63 | 1432.41 | 21.32 | 29.02 | 193.37 | 2.88 |
| 16.43 | 604.65 | 9.00 | 29.75 | 95.65 | 1.42 |
| 18.56 | 344.76 | 5.13 | 30.34 | 104.19 | 1.55 |
| 18.92 | 899.58 | 13.39 | 31.77 | 222.09 | 3.31 |
| 19.57 | 699.01 | 10.40 | 32.28 | 62.67 | 0.93 |
| 19.93 | 301.57 | 4.49 | 34.70 | 51.07 | 0.76 |
| 20.52 | 322.32 | 4.80 | 35.83 | 73.11 | 1.09 |
| 21.43 | 399.96 | 5.95 | 36.32 | 74.54 | 1.11 |
| 21.82 | 274.14 | 4.08 | 37.72 | 46.52 | 0.69 |
| 23.05 | 77.93 | 1.16 | 39.07 | 54.85 | 0.82 |
| 25.14 | 496.48 | 7.39 | | | |

| Pos. [°2Th.] | Height [cts] | Rel. Int. [%] | Pos. [°2Th.] | Height [cts] | Rel. Int. [%] |
|---|---|---|---|---|---|
| 5.97 | 7062.21 | 100.00 | 19.00 | 432.70 | 6.13 |
| 6.96 | 2499.84 | 35.40 | 19.35 | 198.30 | 2.81 |
| 7.20 | 1833.25 | 25.96 | 21.58 | 242.92 | 3.44 |
| 9.35 | 722.81 | 10.23 | 22.05 | 115.64 | 1.64 |
| 11.85 | 178.54 | 2.53 | 24.17 | 40.83 | 0.58 |
| 12.47 | 755.45 | 10.70 | 24.97 | 63.39 | 0.90 |
| 13.92 | 81.38 | 1.15 | 26.77 | 88.72 | 1.26 |
| 14.37 | 282.65 | 4.00 | 28.22 | 80.22 | 1.14 |
| 15.59 | 541.74 | 7.67 | 35.14 | 82.49 | 1.17 |
| 16.11 | 106.45 | 1.51 | 37.65 | 33.30 | 0.47 |
| 18.26 | 92.12 | 1.30 | | | |

| Pos. [°2Th.] | Height [cts] | Rel. Int. [%] | Pos. [°2Th.] | Height [cts] | Rel. Int. [%] |
|---|---|---|---|---|---|
| 4.49 | 5484.92 | 100.00 | 22.48 | 951.86 | 17.35 |
| 11.49 | 318.78 | 5.81 | 22.75 | 507.64 | 9.26 |
| 13.47 | 3370.90 | 61.46 | 23.54 | 1828.56 | 33.34 |
| 14.32 | 1486.43 | 27.10 | 24.29 | 237.84 | 4.34 |
| 14.66 | 139.45 | 2.54 | 24.95 | 247.86 | 4.52 |
| 15.30 | 77.84 | 1.42 | 26.30 | 234.29 | 4.27 |
| 16.28 | 570.81 | 10.41 | 26.72 | 182.93 | 3.34 |
| 17.39 | 76.40 | 1.39 | 27.90 | 181.69 | 3.31 |
| 18.00 | 3835.74 | 69.93 | 28.68 | 151.53 | 2.76 |
| 18.34 | 1523.83 | 27.78 | 29.01 | 185.49 | 3.38 |
| 19.00 | 1092.44 | 19.92 | 29.60 | 229.64 | 4.19 |
| 19.82 | 250.53 | 4.57 | 30.27 | 306.05 | 5.58 |
| 20.15 | 381.35 | 6.95 | 31.16 | 86.36 | 1.57 |
| 20.56 | 223.06 | 4.07 | 32.30 | 127.32 | 2.32 |
| 20.92 | 139.32 | 2.54 | 34.82 | 155.42 | 2.83 |
| 21.21 | 669.67 | 12.21 | 38.00 | 62.71 | 1.14 |
| 21.43 | 324.23 | 5.91 | 38.72 | 148.96 | 2.72 |

CRYSTALLINE AND SALT FORMS OF AN ORGANIC COMPOUND AND PHARMACEUTICAL COMPOSITIONS THEREOF

RELATED APPLICATIONS

This application is a 35 U.S.C. § 371 national stage filing of International Application No. PCT/US2019/067897, filed on Dec. 20, 2019 which in turn claims the benefit of priority of U.S. Provisional Patent Application No. 62/784,083, filed Dec. 21, 2018; U.S. Provisional Application No. 62/791,571, filed Jan. 11, 2019; and U.S. Provisional Application No. 62/882,712, filed Aug. 5, 2019. The entire contents of each of which are incorporated by reference in their entireties.

BACKGROUND

Dihydroorotate dehydrogenase (DHODH) is an enzyme that catalyzes one of the steps in the de novo pyrimidine nucleotide biosynthetic pathway. It catalyzes the only oxidation/reduction reaction in that pathway, which is the step of converting DHO (dihydroorotate) to orotate with the aid of flavin cofactor and an electron acceptor. Inhibitors of dihydroorotate dehydrogenase have been found to possess wider applications as chemotherapeutic agents.

1-methyl-5-(2'-methyl-[1,1'-biphenyl]-yl)-1H-benzo[d][1,2,3]triazole-7-carboxylic acid, hereinafter also referred to as "Compound 1" (structural formula shown below), has been characterized as an inhibitor of DHODH. See e.g., International Patent Application Publication No. WO 2014/128669 and U.S. Pat. No. 9,630,932, the contents of which are incorporated herein by reference.

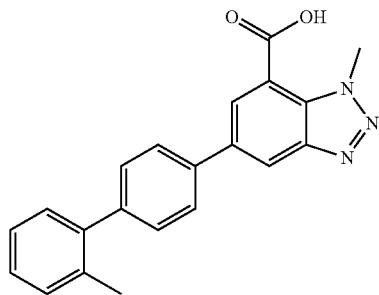 [SMILES: Cc1ccccc1-c1ccc(-c2cc(C(=O)O)c3c(c2)nnn3C)cc1]

Compound 1 was developed to treat conditions and disorders that would benefit from inhibition of DHODH, such as but not limited to solid cancers, hematological cancers, viral-mediated diseases, transplant rejection, rheumatoid arthritis, psoriasis, autoimmune diseases, and inflammatory disorders. Given its therapeutic benefits, and the great promise for treating a plethora of different diseases, there is a need to develop alternative forms of Compound 1 in an effort to facilitate isolation, manufacturing, and formulation development for various routes of administration, as well as to enhance storage stability.

SUMMARY

As described in greater detail in the following paragraphs, it has now been found that the Tris salt of Compound 1 has superior properties relative to the free acid and other salt forms of the compound. It has also been found that the Tris salt Form C is superior to other Tris salt forms.

During the salt screening studies described herein, over 50 different salt hits of Compound 1 which included 10 counterions and five different solvents were evaluated. 12 different crystalline forms were identified (see Table 8). Of these crystalline salt forms, the Tris salt form was found to be superior. Specifically, Tris salt Form A and Tris salt Form C of Compound 1 stood out as leading crystalline salt forms with sharp XRPD peaks (see Example 3, Table 8 and FIG. 6). Good crystallinity of drug substance typically translates to better physical and chemical stability and is therefore a desirable characteristic of an active pharmaceutical ingredient (API). Moreover, the thermogravimetric analysis (TGA) data reflects negligible weight loss for the Tris salt Form A and Tris salt Form C of Compound 1 (see Table 9), therefore indicating minimal residual solvents and an anhydrate polymorph, which is often preferred over solvated/hydrated forms for oral solid dosage form development. The differential scanning calorimetry (DSC) data for the Tris salt Form A and Tris salt Form C of Compound 1 (see Table 9) further indicates one sharp melting endotherm prior to decomposition, indicates a low likelihood of polymorphic changes and low possibility of phase transformations that are often undesirable from the perspective of physical stability of the API.

Comparing the Tris salt Form A and Tris salt Form C of Compound 1, thermodynamic stability studies using slurry competition experiments indicated that Tris salt Form C is more thermodynamically stable (see Example 5). Furthermore, Tris salt Form C of Compound 1 was also found to be less hygroscopic than its Tris salt Form A counterpart, making it more easily disintegrate in solvents during formulation development.

Comparing the pharmacokinetic properties of the free acid and the Tris salt of Compound 1, the Tris salt form is clearly superior in terms of achieving a higher maximum concentration (i.e., higher $C_{max}$) within a shorter time period (i.e., lower $T_{max}$) (see Example 8 and Table 13). Although initial forms of the free acid having low crystallinity and purity show comparable exposure to the Tris salt as indicated by AUC values (see Table 13 and FIG. 10A), such high AUC values could not reproduced with a near-final form of the free acid having improved crystallinity and purity, and despite particle size reduction (see Table 13 and FIG. 10B).

The PK data indicates that the Tris salt of Compound 1 shows excellent exposure, as well as faster and higher absorption compared to the free acid form. The relatively clean DSC profile with the sharp melting endotherm for Tris salt Form C of Compound 1, coupled with excellent thermodynamic properties and low hygroscopicity, is an indication of reliable solid state properties of this particular salt form from the perspective of physical stability and suitability of oral solid dosage form development.

Provided herein are tris(hydroxymethyl)aminomethane salt, sodium salt and crystalline forms of the compound referred to herein as Compound 1.

Also provided herein are pharmaceutical compositions comprising the tris(hydroxymethyl)aminomethane (Tris) salt, sodium salt, and other pharmaceutically acceptable salts of Compound 1 and crystalline forms, methods for their manufacture, and uses thereof for treating conditions, including but not limited to conditions that would benefit from inhibition of dihydroorotate dehydrogenase (DHODH).

Also provided herein are solid dispersions comprising Compound 1 or a pharmaceutically acceptable salt thereof, the Tris salt of Compound 1, or the sodium salt of Compound 1 and one or more polymer(s). Also provided herein are pharmaceutical compositions comprising these solid dispersions, methods for their manufacture and uses thereof for treating conditions, including but not limited to conditions that would benefit from inhibition of DHODH.

DETAILED DESCRIPTION

Definitions

Figure 1:
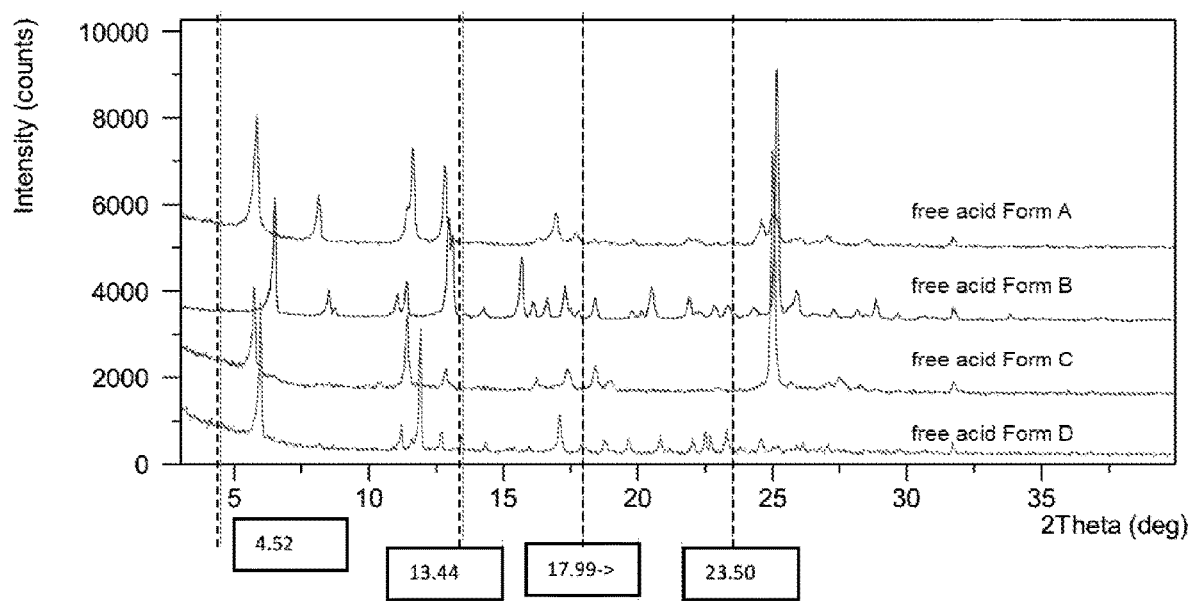
FIG. 1 depicts the XRPD for Forms A, B, C and D of Compound 1.

When used alone, the terms "Form A", "Form B", "Form C", and "Form D", when describing Compound 1, refer to the crystalline forms A, B, C and D of Compound 1, respectively. Additionally, the terms "Form A", "Form B", and "Form C", when describing the tris(hydroxymethyl)aminomethane (Tris) salt of Compound 1, refer to the crystalline forms A, B and C of the tris(hydroxymethyl)aminomethane salt of Compound 1, respectively. The terms "Form A", "crystalline Form A", referring to either a crystalline form A of Compound 1 or the Tris salt of Compound 1, are used interchangeably. Similarly, "Form B" and "crystalline Form B", and "Form C" and "crystalline Form C", referring to either a crystalline form B or form C of Compound 1 or the Tris salt of Compound 1 respectively, as well as "Form D" and "crystalline Form D" referring to a crystalline form D of Compound 1 are used interchangeably.

The term "amorphous" means a solid that is present in a non-crystalline state or form. Amorphous solids are disordered arrangements of molecules and therefore possess no distinguishable crystal lattice or unit cell and consequently have no definable long range ordering. Solid state ordering of solids may be determined by standard techniques known in the art, e.g., by X-ray powder diffraction (XRPD) or differential scanning calorimetry (DSC). Amorphous solids can also be differentiated from crystalline solids e.g., by birefringence using polarized light microscopy.

In general, Compound 1 can contain one or more impurities in any amount(s). In some embodiments the term "impurities" refers to chemical impurities such as for example, reaction by-products. In this application this can also be referred to as chemical purity. In other embodiments, the term "impurities" refer to other solid state forms of Compound 1 or salts thereof. In such embodiments, other solid state forms of Compound 1 or its salts can include amorphous or other crystalline forms. As used herein, the term "substantially amorphous" refers to forms and compositions of amorphous Compound 1 that are free of impurities and/or free of crystalline forms of Compound 1 (including crystalline salts of Compound 1) at a particular weight percentage. Particular weight percentages are 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or any percentage between 60% and 100% free of impurities and/or crystalline forms of Compound 1. In some embodiments, substantially amorphous refers to a free form or salt form of Compound 1 that is at least 90% pure. In other embodiments, substantially amorphous refers to a free form or salt form of Compound 1 that is at least 80% pure. In other embodiments, the term substantially amorphous refers to a free form or salt form that is at least 70% pure. In other embodiments, substantially amorphous refers to a composition comprising Compound 1 having less than about 30%, having less than about 20%, less than about 15%, less than about 10%, less than about 5%, or less than about 1% crystalline Compound 1.

As used herein, "crystalline" refers to a solid form of Compound 1 or a Tris salt of Compound 1 wherein there exists long-range atomic order in the positions of the atoms. The crystalline nature of a solid can be confirmed, for example, by examination of the X-ray powder diffraction pattern. If the XRPD shows sharp intensity peaks in the XRPD then the compound is crystalline. A solid form of Compound 1 or a Tris salt of Compound 1 that is "crystalline" is a solid that is completely crystalline or partially crystalline, and encompasses solids that are at least 80% crystalline, 85% crystalline, 90% crystalline, 95% crystalline, and 99% crystalline, by weight. Contrary to amorphous solids that have been defined above, crystalline solids are ordered arrangements of molecules that possess distinguishable crystal lattice or unit cell, and consequently have definable long range ordering. In some embodiments, substantially crystalline refers to a solid form of Compound 1 or a Tris salt of Compound 1 that is at least 80% crystalline. In other embodiments, substantially crystalline refers to a solid form that is at least 90% crystalline.

As used herein, chemical purity refers to extent to which the disclosed form is free from materials having different chemical structures. Chemical purity of the compound in the disclosed crystal forms means the weight of the compound divided by the sum of the weight of the compound plus materials/impurities having different chemical structures multiplied by 100%, i.e., percent by weight. In one embodiment, the compound in the disclosed crystalline forms has a chemical purity of at least 60%, at least 70%, at least 80%, at least 90%, at least 95%, or at least 99% by weight.

The term "solvate" refers to a crystalline Compound 1 or a crystalline Tris salt of Compound 1 wherein a stoichiometric or non-stoichiometric amount of solvent, or mixture of solvents, is incorporated into the crystal structure.

The term "hydrate" refers to a crystalline Compound 1 or a crystalline Tris salt of Compound 1 where a stoichiometric or non-stoichiometric amount of water is incorporated into the crystal structure. A hydrate is a solvate wherein the solvent incorporated into the crystal structure is water. The term "anhydrous" when used with respect to a compound means substantially no solvent incorporated into the crystal structure, e.g., less than 0.1% by weight as determined by Karl Fisher analysis. A compound that is anhydrous is referred to herein as an "anhydrate".

As used herein, the term "major peak" refers to the three most intense peaks of an XRPD data pattern, or to the peaks having at least 50% of the 100% relative intensity of the most intense peak.

A single crystalline form of Compound 1 or the Tris salt of Compound 1 means that 1-methyl-5-(2'-methyl-[1,1'-biphenyl]-yl)-1H-benzo[d][1,2,3]triazole-7-carboxylic acid or 1-methyl-5-(2'-methyl-[1,1'-biphenyl]-yl)-1H-benzo[d][1,2,3]triazole-7-carboxylate Tris salt is present as a single crystal or a plurality of crystals, in which each crystal has the same crystal form (i.e., Form A, B, C or D for free acid or Form A, B, or C for the Tris salt). When the crystal form is defined as a specified percentage of one particular single crystalline form of the compound, the remainder is made up of amorphous form and/or crystalline forms other than the one or more particular forms that are specified. In one embodiment, the crystalline form is at least 60% a single crystalline form, at least 70% a single crystalline form, at least 80% a single crystalline form, at least 90% a single crystalline form, at least 95% a single crystalline form, or at least 99% a single crystalline form by weight. Percent by weight of a particular crystal form is determined by the weight of the particular crystal form divided by the sum weight of the particular crystal, plus the weight of the other crystal forms present plus the weight of amorphous form present multiplied by 100%.

The 2-theta values of the X-ray powder diffraction patterns for the crystalline forms described herein may vary slightly from one instrument to another and also depending on variations in sample preparation and batch to batch variation. Therefore, unless otherwise defined, the XRPD patterns and/or the 2-theta peak values recited herein are not to be construed as absolute and can vary by ±0.2 degrees. The 2-theta values provided herein were obtained using Cu Kα1 radiation.

Temperature values, e.g., for DSC peak temperatures and DSC onset temperatures herein may vary slightly from one instrument to another and also depending on variations in sample preparation, the rate of temperature increases over the course of the experiment, batch to batch variation of the material, and other environmental factors. Therefore, unless otherwise defined, temperature values recited herein are not to be construed as absolute and can vary by ±5 degrees.

"Substantially the same XRPD pattern" or "an X-ray powder diffraction pattern substantially similar to" a defined figure means that for comparison purposes, at least 90% of the peaks shown are present. It is to be further understood that for comparison purposes some variability in 2-theta peak positions from those shown is allowed, such as ±0.2 degrees. It should be understood that when the expression "characterized by X-ray powder diffraction peaks at 2θ angles (±0.2°)" followed by a list of 2-theta peak positions that the ±0.2 degrees applies to each and every one of the peak positions listed.

A "therapeutically effective amount" of a crystalline form of Compound 1, or a crystalline Tris salt form of Compound 1, or a salt of Compound 1 (e.g., non-crystalline or amorphous or partially crystalline Tris salt or Na salt of Compound 1), as described herein, is an amount sufficient to provide a therapeutic benefit in the treatment of a condition or to delay or minimize one or more symptoms associated with the condition. The term "therapeutically effective amount" and "effective amount" are used interchangeably. In one aspect, a therapeutically effective amount of a compound means an amount of therapeutic or active agent, alone or in combination with other therapies, which provides a therapeutic benefit in the treatment of the condition. The terms "therapeutic agent" and "active agent" are used interchangeably. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for eliciting therapeutic effects in the treatment of a cancer (including solid tumors and hematological cancers as further described herein), a viral-mediated disease, transplant rejection, rheumatoid arthritis, psoriasis, an autoimmune disease, or an inflammatory disorder. In certain embodiments, a therapeutically effective amount is an amount sufficient for eliciting therapeutic effects in the treatment of a cancer (including solid tumors and hematological cancers as further described herein), a viral-mediated disease, transplant rejection, rheumatoid arthritis, psoriasis, an autoimmune disease, or an inflammatory disorder, wherein the condition is responsive to inhibition of dihydroorotate dehydrogenase (DHODH). In certain embodiments, a therapeutically effective amount is an amount sufficient for regulating DHODH levels such that it improves overall therapy, reduces or avoids symptoms, signs, or causes of the condition, and/or enhances the therapeutic efficacy of another therapeutic agent. A therapeutically effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to reduce the likelihood of or delay their recurrence.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment. In certain embodiments, the term "subject" refers to a human subject in need of treatment of a disease. In certain embodiments, the term "subject" refers to a human subject in need of treatment by inhibition of DHODH. In certain embodiments, the term "subject" refers to a human adult over 18 years old in need of treatment of a disease. In certain embodiments, the term "subject" refers to a human child no more than 18 years old in need of treatment of a disease.

The term "pharmaceutically acceptable carrier" refers to a non-toxic carrier, adjuvant, or vehicle that does not adversely affect the pharmacological activity of the compound with which it is formulated, and which is also safe for human use.

The term "pharmaceutically acceptable excipient" refers to a substance or substances that aids the administration of an active agent to a subject by, for example, modifying the stability of an active agent or modifying the absorption by a subject upon administration. A pharmaceutically acceptable excipient typically has no significant adverse toxicological effect on the patient.

In this description, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

As used herein, the terms "about" and "approximately" when used in combination with a numeric value or range of values used to characterize a particular crystal form, amorphous form, or mixture thereof of a compound mean the value or range of values may deviate to an extent deemed reasonable to one of ordinary skill in the art while describing the particular crystal form, amorphous form, or mixture thereof.

As used herein, "% w/w" is used to mean by weight as a percentage of a total weight that is used as the basis for calculating the weight percentage of an individual component. By way of example, for a bulk composition, the % w/w of an individual component may be calculated as a percentage of the total weight of all of the components of the bulk composition. By way of another example, for a single oral dosage form, the % w/w of an individual component may be calculated as a percentage of the total weight of all of the components of the single oral dosage form. For example, when the single oral dosage form is a capsule, the total weight may be the total weight of all the components of the capsule.

The term "intragranular excipients" refers to ingredients that are incorporated in the formulation prior to granulation, i.e., ingredients that are located internally in the granule structure.

The term "extragranular excipients" refers to ingredients that are incorporated after granulation, i.e., ingredients that are located externally to the granule structure.

As used herein, the singular form "a", "an", and "the" include plural references unless the context clearly dictates otherwise. For example, the term "an intragranular excipient" includes one or more intragranular excipients.

Compounds

Tris(hydroxymethyl)aminomethane Salts of Compound 1

In a first embodiment, the present disclosure is drawn to a tris(hydroxymethyl)aminomethane (Tris) salt of a compound represented by the formula:

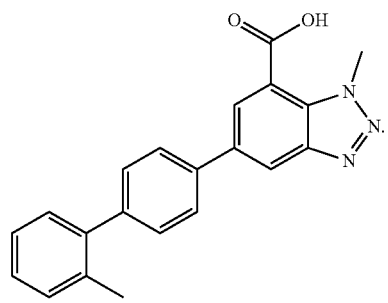 [SMILES: Cc1ccccc1-c1ccc(-c2cc(C(=O)O)c3c(c2)nnn3C)cc1]

In a second embodiment, at least 80% by weight of the Tris salt in accordance with the first embodiment is crystalline. In other embodiment, at least 85%, at least 90%, at least 95% or at least 99% by weight of the Tris salt in accordance with the first embodiment is crystalline.

In a third embodiment, the Tris salt in accordance with the second embodiment is at least 60% a single crystalline form, at least 70% a single crystalline form, at least 80% a single crystalline form, at least 90% a single crystalline form, at least 95% a single crystalline form, or at least 99% a single crystalline form by weight.

In a fourth embodiment, the Tris salt in accordance with any one of the first, second and third embodiments has a chemical purity of at least 60%, at least 70%, at least 80%, at least 90%, at least 95%, or at least 99% by weight.

In a fifth embodiment, the Tris salt in accordance with any one of the first, second, third and fourth embodiments is an anhydrate.

In a sixth embodiment, the Tris salt in accordance with any one of the first, second, third, fourth and fifth embodiments is crystalline Form A characterized by X-ray powder diffraction peaks at 2θ angles (±0.2°) 4.4°, 15.6°, and 18.9°.

In a seventh embodiment, the Tris salt in accordance with any one of the first, second, third, fourth and fifth embodiments is crystalline Form A characterized by major X-ray powder diffraction peaks at 2θ angles (±0.2°) 4.4°, 15.6°, and 18.9°.

In an eighth embodiment, the crystalline Form A in accordance with any one of the sixth and seventh embodiments is further characterized by X-ray powder diffraction peaks at 2θ angles (±0.2°) 11.5°, 16.4°, 19.6° and 25.5°.

In a ninth embodiment, the crystalline Form A in accordance with any one of the sixth, seventh and eighth embodiments is further characterized by at least one X-ray powder diffraction peaks at 2θ angles (±0.2°) selected from 8.7°, 15.2°, 18.6°, 21.4° and 25.1°.

Figures 7A, 7B:
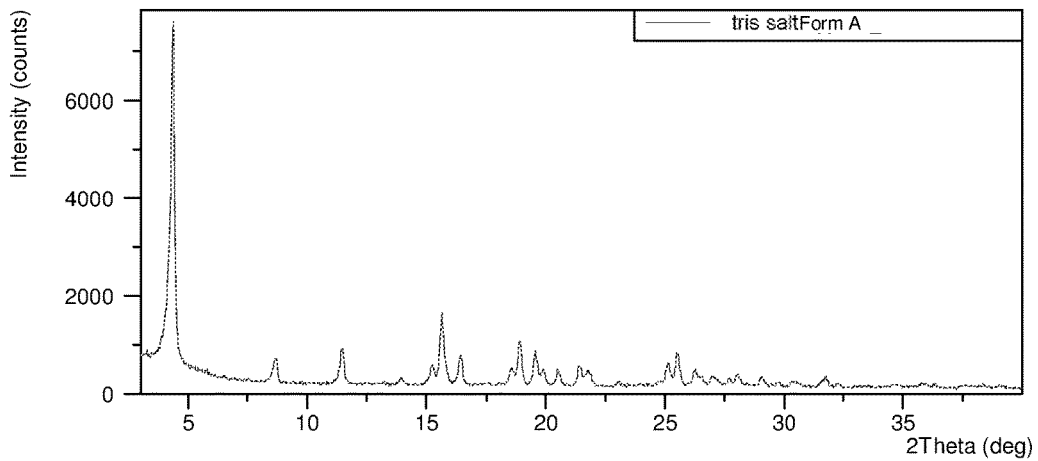
FIG. 7A depicts the XRPD pattern for crystalline Form A of the Tris salt of Compound 1.
FIG. 7B is an XRPD peak list for the crystalline Form A of the Tris salt of Compound 1.

In a tenth embodiment, the crystalline Form A in accordance with any one of the sixth, seventh, eighth and ninth embodiments is characterized by an X-ray powder diffraction pattern substantially similar to FIG. 7A, and XRPD peaks as listed in FIG. 7B.

Figure 7C:
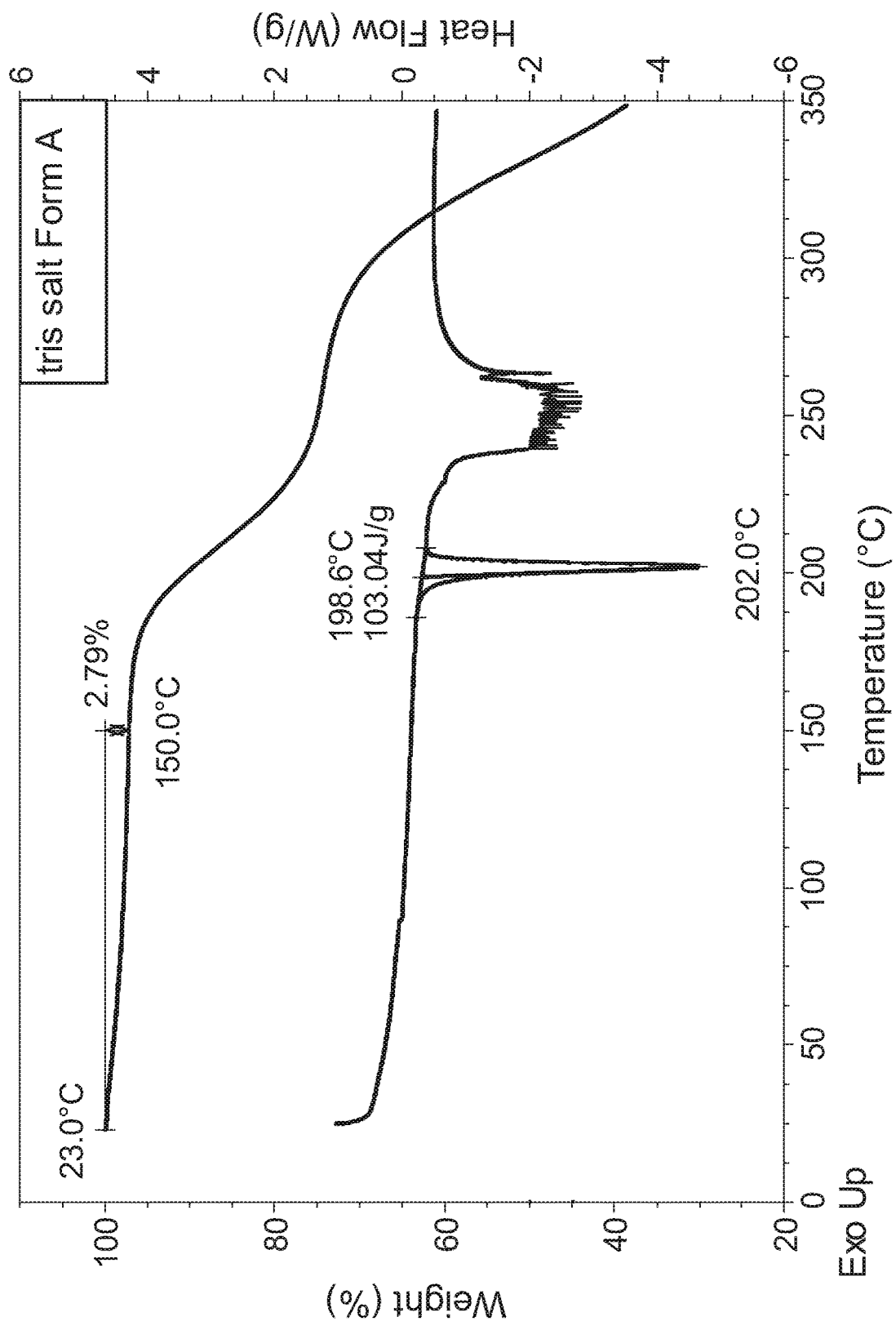
FIG. 7C depicts the combined differential scanning calorimetry (DSC) thermogram and thermogravimetric analysis (TGA) thermogram for the crystalline Form A of the Tris salt of Compound 1.

In an eleventh embodiment, the crystalline Form A in accordance with any one of the sixth, seventh, eighth and ninth embodiments is characterized by a differential scanning calorimetry (DSC) thermograph comprising an endotherm peak temperature at about 202.0° C.±2° C. (see FIG. 7C).

In a twelfth embodiment, the crystalline Form A in accordance with any one of the sixth, seventh, eighth and ninth embodiments is characterized by a thermogravimetric analysis (TGA) thermogram comprising a weight loss of about 2.8% up to about 150° C. (see FIG. 7C)

In a thirteenth embodiment, the Tris salt in accordance with any one of the first, second, third, fourth and fifth embodiments is crystalline Form B characterized by X-ray powder diffraction peaks at 2θ angles (±0.2°) 6.0°, 7.0°, and 7.2°. The X-ray powder diffraction peaks at 2θ angles (±0.2°) 6.0°, 7.0°, and 7.2° are in one embodiment major peaks.

In a fourteenth embodiment, the crystalline Form B in accordance with the thirteenth embodiment is further characterized by at least one X-ray powder diffraction peak at 2θ angles (±0.2°) selected from 9.3° and 12.5°.

In a fifteenth embodiment, the crystalline Form B in accordance with any one of the thirteenth and fourteenth embodiments is further characterized by at least one X-ray powder diffraction peaks at 2θ angles (±0.2°) selected from 15.6° and 19.0°.

Figures 8A, 8B:
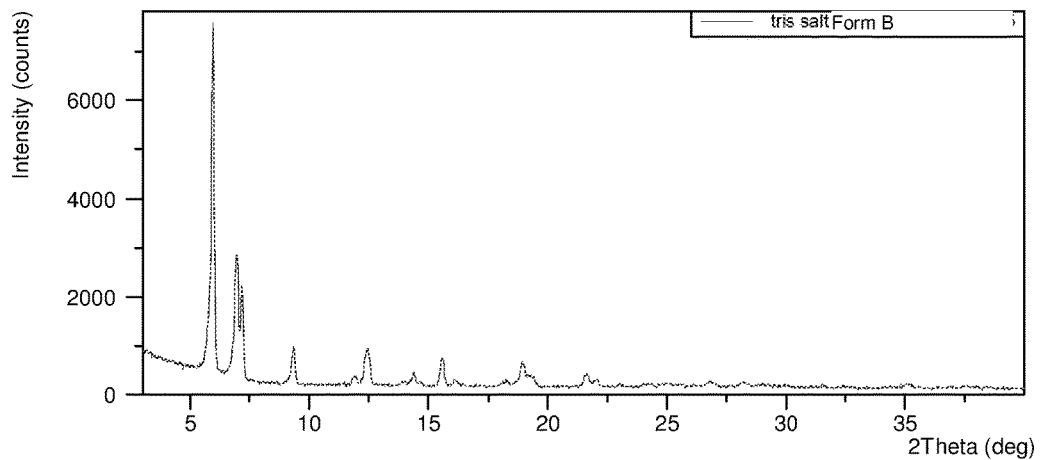
FIG. 8A depicts the XRPD pattern for crystalline Form B of the Tris salt of Compound 1.
FIG. 8B is an XRPD peak list for the crystalline Form B of the Tris salt of Compound 1.

In a sixteenth embodiment, the crystalline Form B in accordance with any one of the thirteenth, fourteenth and fifteenth embodiments is characterized by an X-ray powder diffraction pattern substantially similar to FIG. 8A, and XRPD peaks as listed in FIG. 8B.

In a seventeenth embodiment, the crystalline Form B in accordance with any one of the thirteenth, fourteenth, fifteenth and sixteenth embodiments is characterized by a differential scanning calorimetry (DSC) thermograph comprising an overlapped endo-/exotherm peak temperature at about 129.9° C.±2° C. and an endotherm peak temperature at about 205.8° C.±2° C. (see FIG. 8C).

In an eighteenth embodiment, the crystalline Form B in accordance with any one of the thirteenth, fourteenth, fifteenth, sixteenth and seventeenth embodiments is characterized by a thermogravimetric analysis (TGA) thermogram comprising a weight loss of about 10.8% up to about 190° C. (see FIG. 8C).

In a nineteenth embodiment, the Tris salt in accordance with any one of the first, second, third, fourth and fifth embodiments is crystalline Form C characterized by X-ray powder diffraction peaks at 2θ angles (±0.2°) 4.5°, 13.5°, and 18.0°.

In a twentieth embodiment, the Tris salt in accordance with any one of the first, second, third, fourth and fifth embodiments is crystalline Form C characterized by major X-ray powder diffraction peaks at 2θ angles (±0.2°) 4.5°, 13.5°, and 18.0°.

In a twenty-first embodiment, the crystalline Form C in accordance with any one of the nineteenth and twentieth embodiments is further characterized by at least one X-ray powder diffraction peak at 2θ angles (±0.2°) selected from 14.3°, 18.3°, and 23.5°.

In a twenty-second embodiment, the crystalline Form C in accordance with any one of the nineteenth, twentieth and twenty-first embodiments is further characterized by at least one X-ray powder diffraction peaks at 2θ angles (±0.2°) selected from 16.3°, 19.0°, 21.2°, 21.4°, 22.5°, and 22.8°.

Figures 9A, 9B:
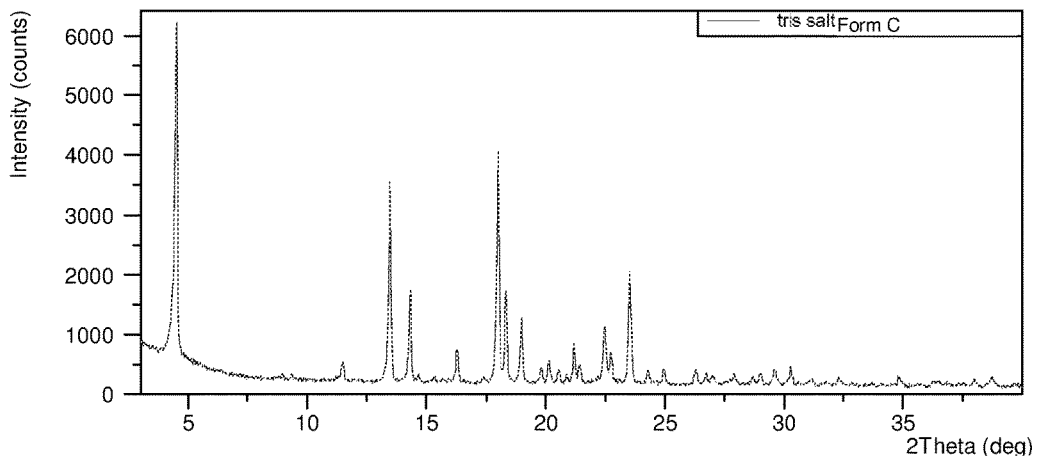
FIG. 9A depicts the XRPD pattern for crystalline Form C of the Tris salt of Compound 1.
FIG. 9B is an XRPD peak list for the crystalline Form C of the Tris salt of Compound 1.

In a twenty-third embodiment, the crystalline Form C in accordance with any one of the nineteenth, twentieth, twenty-first and twenty-second embodiments is characterized by an X-ray powder diffraction pattern substantially similar to FIG. 9A, and XRPD peaks as listed in FIG. 9B.

Figure 9C:
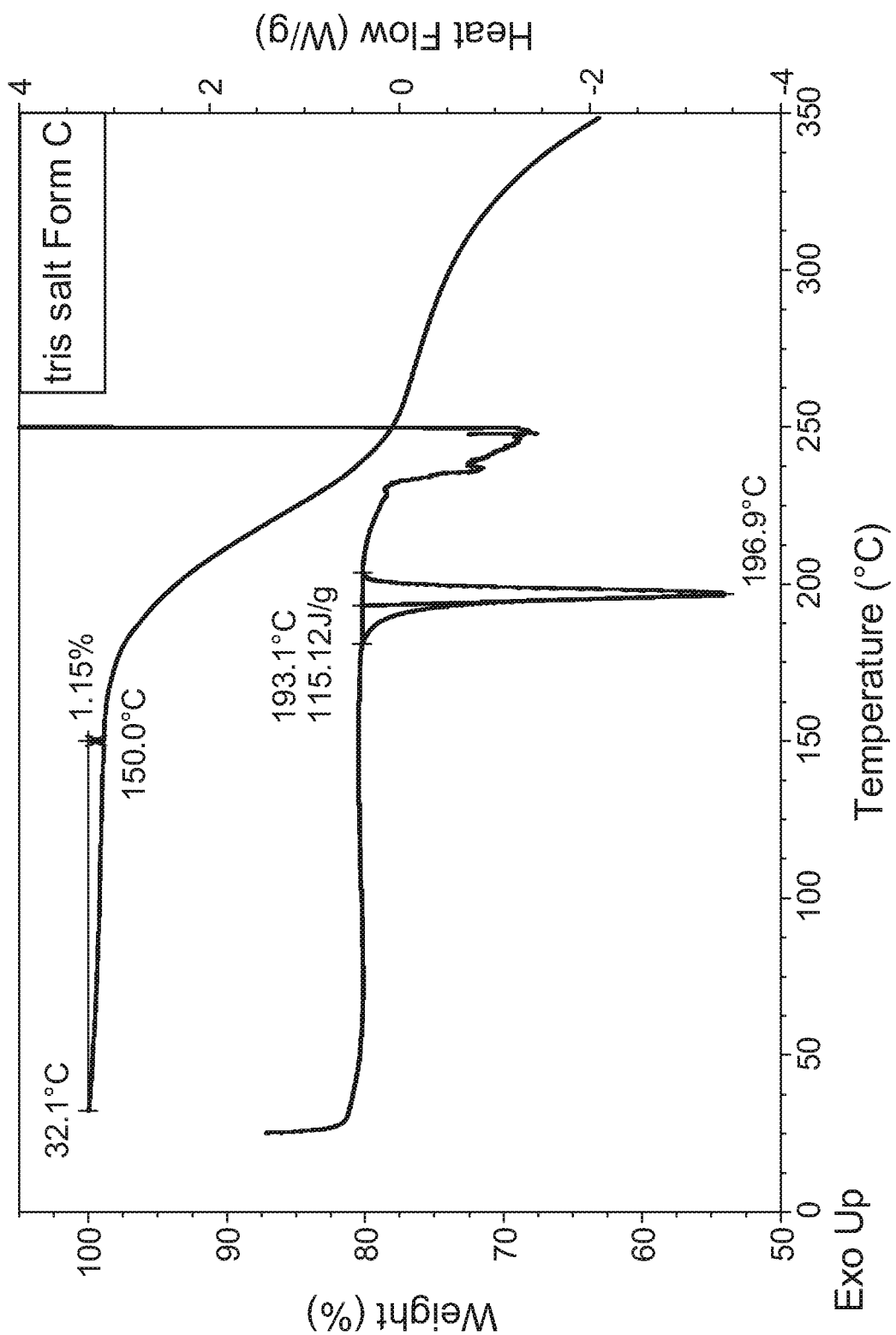
FIG. 9C depicts the combined DSC thermogram and TGA thermogram for the crystalline Form C of the Tris salt of Compound 1.

In a twenty-fourth embodiment, the crystalline Form C in accordance with any one of the nineteenth, twentieth, twenty-first, twenty-second and twenty-third embodiments is characterized by a differential scanning calorimetry (DSC) thermograph comprising an endotherm peak temperature at about 196.9° C.±2° C. (see FIG. 9C).

In a twenty-fifth embodiment, the crystalline Form C in accordance with any one of the nineteenth, twentieth, twenty-first, twenty-second, twenty-third and twenty-fourth embodiments is characterized by a thermogravimetric analysis (TGA) thermogram comprising a weight loss of about 1.2% up to about 150° C. (see FIG. 9C).

In a twenty-sixth embodiment, the present disclosure is drawn to a sodium salt of a compound represented by the formula:

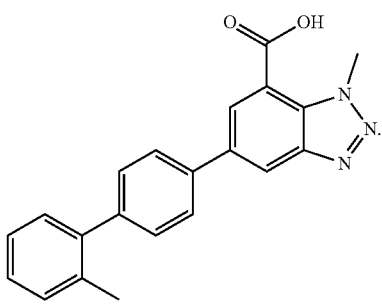 [SMILES: Cc1ccccc1-c1ccc(-c2cc(C(=O)O)c3c(c2)nnn3C)cc1]

The sodium salt of Compound 1 is preferably in a solid or solid crystalline form.

In a twenty-seventh embodiment, the present disclosure is drawn to a crystalline form of a compound represented by the formula:

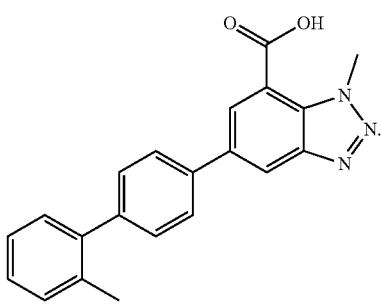 [SMILES: Cc1ccccc1-c1ccc(-c2cc(C(=O)O)c3c(c2)nnn3C)cc1]

In a twenty-eighth embodiment, the crystalline form in accordance with the twenty-seventh embodiment is an anhydrate.

In a twenty-ninth embodiment, the crystalline form in accordance with the twenty-seventh embodiment is a solvate.

In a thirtieth embodiment, the crystalline form in accordance with any one of the twenty-seventh and twenty-eighth embodiments is crystalline Form A characterized by X-ray powder diffraction peaks at 2θ angles (±0.2°) 5.8°, 11.6°, and 12.8°.

In a thirty-first embodiment, the crystalline form in accordance with any one of the twenty-seventh and twenty-eighth embodiments is crystalline Form A characterized by major X-ray powder diffraction peaks at 2θ angles (±0.2°) 5.8°, 11.6°, and 12.8°.

In a thirty-second embodiment, the crystalline Form A in accordance with any one of the thirtieth and thirty-first embodiments is further characterized by an X-ray powder diffraction peaks at 2θ angle (±0.2°) 8.1° and 16.9°.

In a thirty-third embodiment, the crystalline Form A in accordance with any one of the thirtieth, thirty-first and thirty-second embodiments is further characterized by at least one X-ray powder diffraction peaks at 2θ angles (±0.2°) selected from 11.4°, 18.4°, 21.9°, 24.6°, 24.9° and 25.1°.

Figures 2A, 2B:
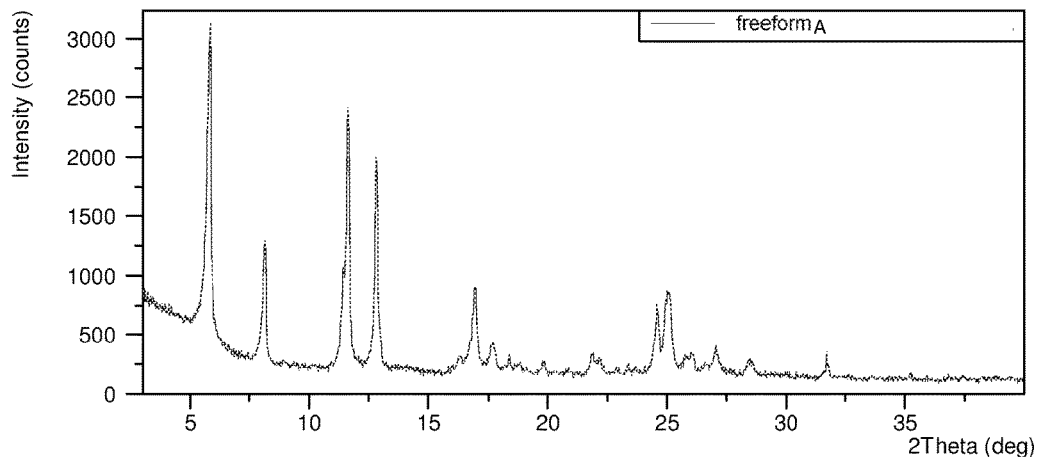
FIG. 2A depicts the XRPD pattern for crystalline Form A of Compound 1.
FIG. 2B is an XRPD peak list for the crystalline Form A of Compound 1.

In a thirty-fourth embodiment, the crystalline Form A in accordance with any one of the thirtieth, thirty-first, thirty-second and thirty-third embodiments is characterized by an X-ray powder diffraction pattern substantially similar to FIG. 2A, and XRPD peaks as listed in FIG. 2B.

Figure 2C:
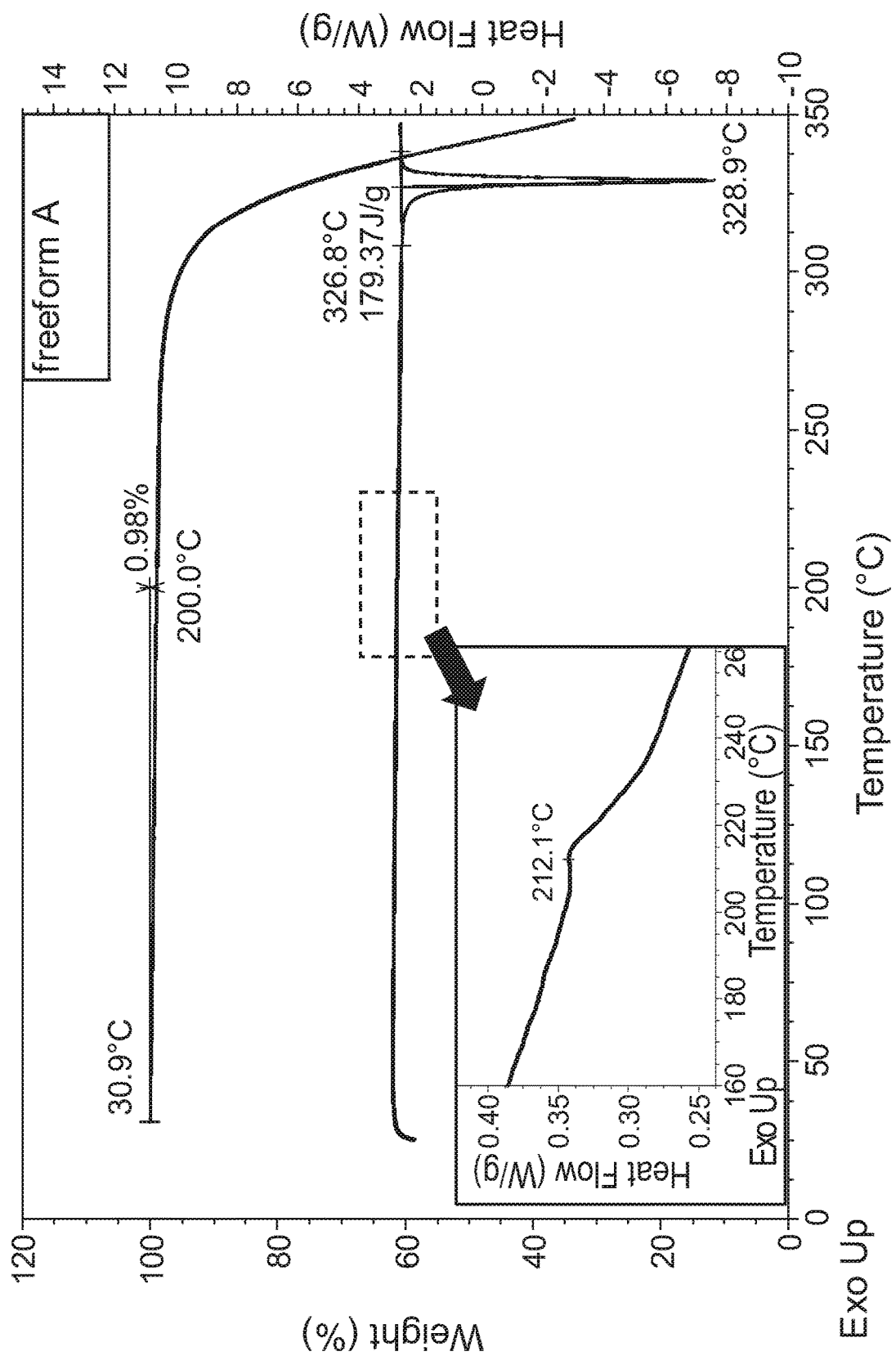
FIG. 2C depicts the combined DSC thermogram and TGA thermogram for the crystalline Form A of Compound 1.

In a thirty-fifth embodiment, the crystalline Form A in accordance with any one of the thirtieth, thirty-first, thirty-second, thirty-third and thirty-fourth embodiments is characterized by a differential scanning calorimetry (DSC) thermograph comprising peak temperatures at about 212.1° C.±2° C. (exothermic) and 328.9° C.±2° C. (endothermic) (see FIG. 2C).

In a thirty-sixth embodiment, the crystalline Form A in accordance with any one of the thirtieth, thirty-first, thirty-second, thirty-third, thirty-fourth and thirty-fifth embodiments is characterized by a thermogravimetric analysis (TGA) thermogram comprising a weight loss of about 1.0% up to about 200° C. (see FIG. 2C).

In a thirty-seventh embodiment, the crystalline form in accordance with any one of the twenty-seventh and twenty-eighth embodiments is crystalline Form B characterized by X-ray powder diffraction peaks at 2θ angles (±0.2°) 6.5°, 12.9°, and 25.1°.

In a thirty-eighth embodiment, the crystalline form in accordance with any one of the twenty-seventh and twenty-eighth embodiments is crystalline Form B characterized by major X-ray powder diffraction peaks at 2θ angles (±0.2°) 6.5°, 12.9°, and 25.1°.

In a thirty-ninth embodiment, the crystalline Form B in accordance with any one of the thirty-seventh and thirty-eighth embodiments is further characterized by an X-ray powder diffraction peaks at 2θ angle (±0.2°) 13.1° and 15.7°.

In a fortieth embodiment, the crystalline Form B in accordance with any one of the thirty-seventh, thirty-eighth and thirty-ninth embodiments is further characterized by at least one X-ray powder diffraction peaks at 2θ angles (±0.2°) selected from 8.5°, 11.1°, 11.4°, 17.3°, 20.5°, 21.9° and 25.9°.

Figures 3A, 3B:
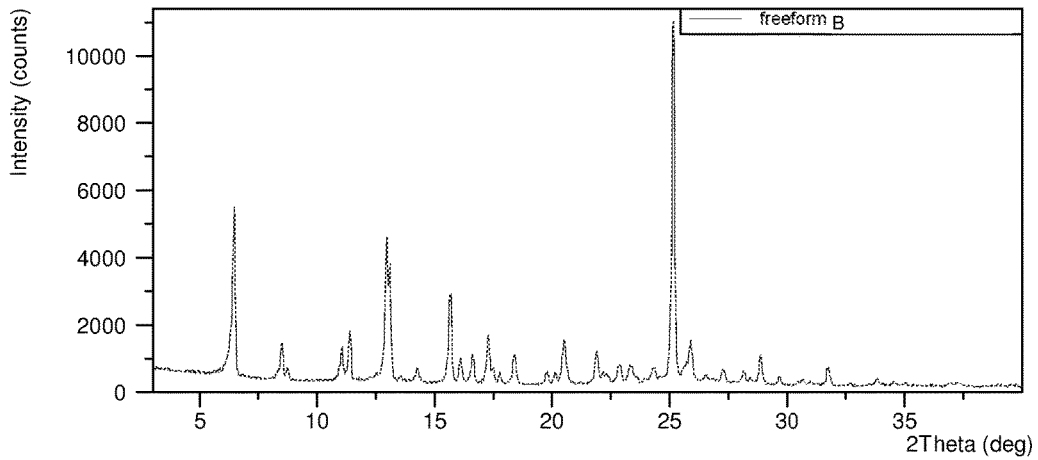
FIG. 3A depicts the XRPD pattern for crystalline Form B of Compound 1.
FIG. 3B is an XRPD peak list for the crystalline Form B of Compound 1.

In a forty-first embodiment, the crystalline Form B in accordance with any one of the thirty-seventh, thirty-eighth, thirty-ninth and fortieth embodiments is characterized by an X-ray powder diffraction pattern substantially similar to FIG. 3A, and XRPD peaks as listed in FIG. 3B.

Figure 3C:
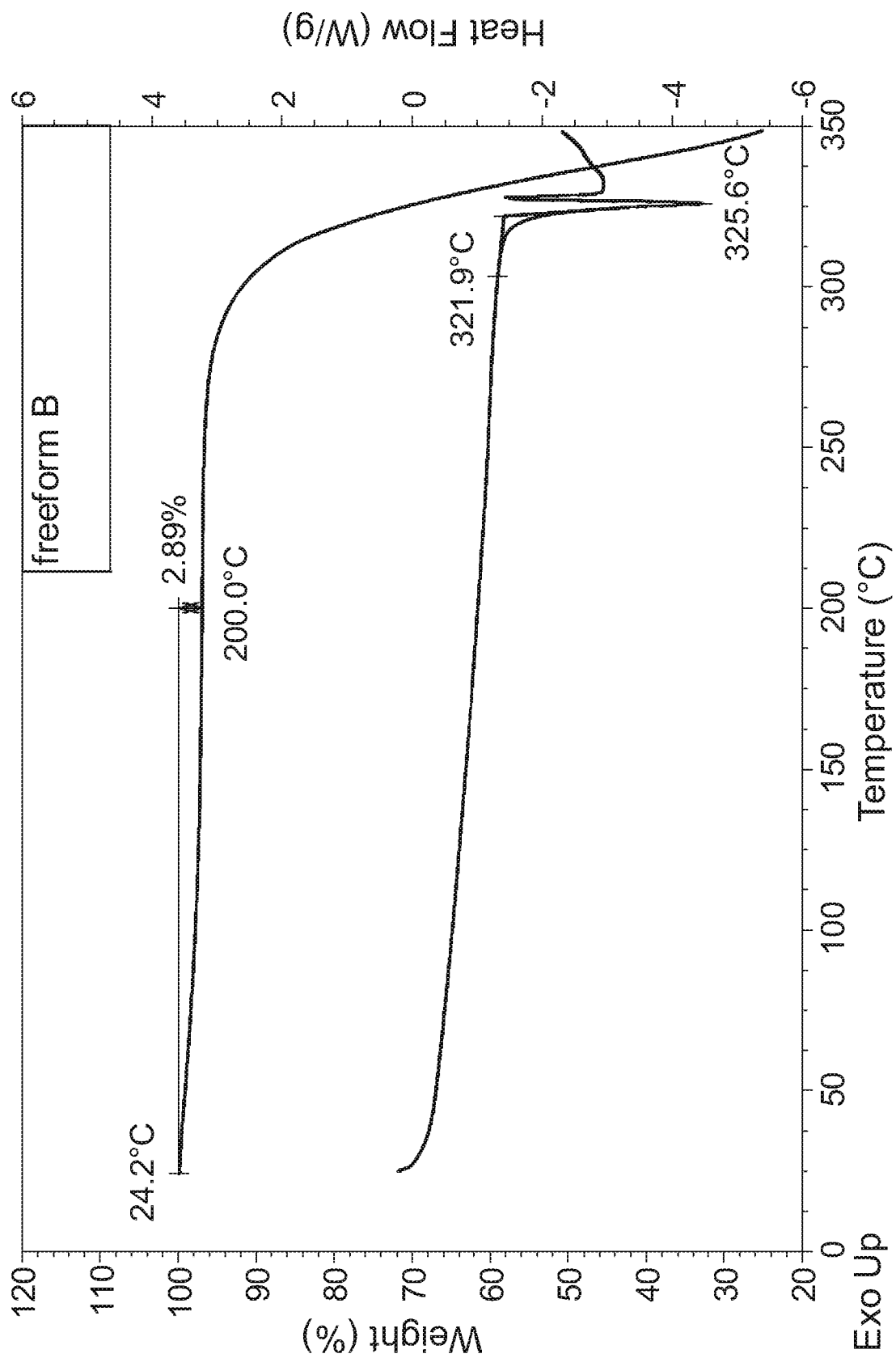
FIG. 3C depicts the combined DSC thermogram and TGA thermogram for the crystalline Form B of Compound 1.

In a forty-second embodiment, the crystalline Form B in accordance with any one of the thirty-seventh, thirty-eighth, thirty-ninth, fortieth and forty-first embodiments is characterized by a differential scanning calorimetry (DSC) thermograph comprising an endotherm peak temperature at about 325.6° C.±2° C. (see FIG. 3C).

In a forty-third embodiment, the crystalline Form B in accordance with any one of the thirty-seventh, thirty-eighth, thirty-ninth, fortieth, forty-first and forty-second embodiments is characterized by a thermogravimetric analysis (TGA) thermogram comprising a weight loss of about 2.9% up to about 200° C. (see FIG. 3C).

In a forty-fourth embodiment, the crystalline form in accordance with any one of the twenty-seventh and twenty-eighth embodiments is crystalline Form C characterized by X-ray powder diffraction peaks at 2θ angles (±0.2°) 5.7°, 11.4°, and 25.0°.

In a forty-fifth embodiment, the crystalline form in accordance with any one of the twenty-seventh, twenty-eighth and twenty-ninth embodiments is crystalline Form C characterized by major X-ray powder diffraction peaks at 2θ angles (±0.2°) 5.7°, 11.4°, and 25.0°.

In a forty-sixth embodiment, the crystalline Form C in accordance with any one of the forty-fourth and forty-fifth embodiments is further characterized by an X-ray powder diffraction peaks at 2θ angle (±0.2°) 3.2°, 17.4° and 18.4°.

In a forty-seventh embodiment, the crystalline Form C in accordance with any one of the forty-fourth, forty-fifth and forty-sixth embodiments is further characterized by at least one X-ray powder diffraction peak at 2θ angles (±0.2°) selected from 12.8°, 16.2°, 19.0°, 27.5°, and 31.7°.

Figures 4A, 4B:
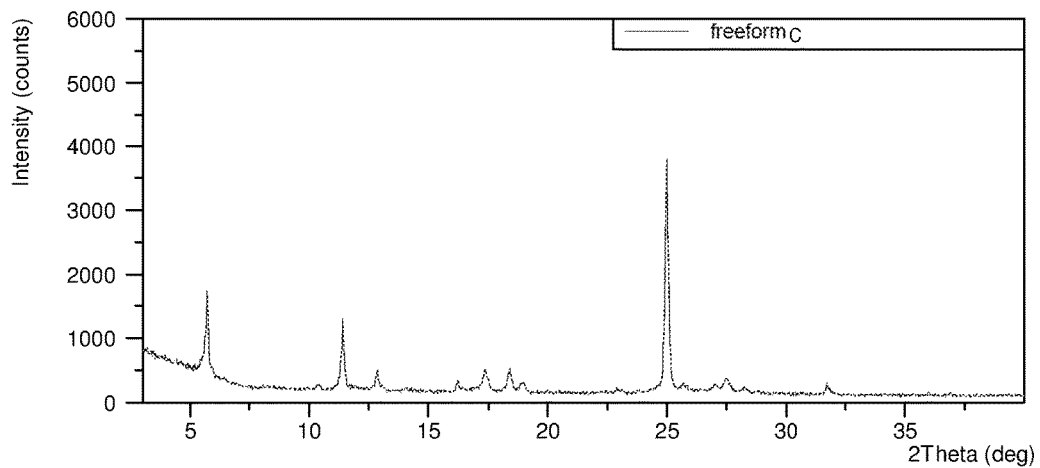
FIG. 4A depicts the XRPD pattern for crystalline Form C of Compound 1.
FIG. 4B is an XRPD peak list for the crystalline Form C of Compound 1.

In a forty-eighth embodiment, the crystalline Form C in accordance with any one of the forty-fourth, forty-fifth, forty-sixth and forty-seventh embodiments is characterized by an X-ray powder diffraction pattern substantially similar to FIG. 4A, and XRPD peaks as listed in FIG. 4B.

Figure 4C:
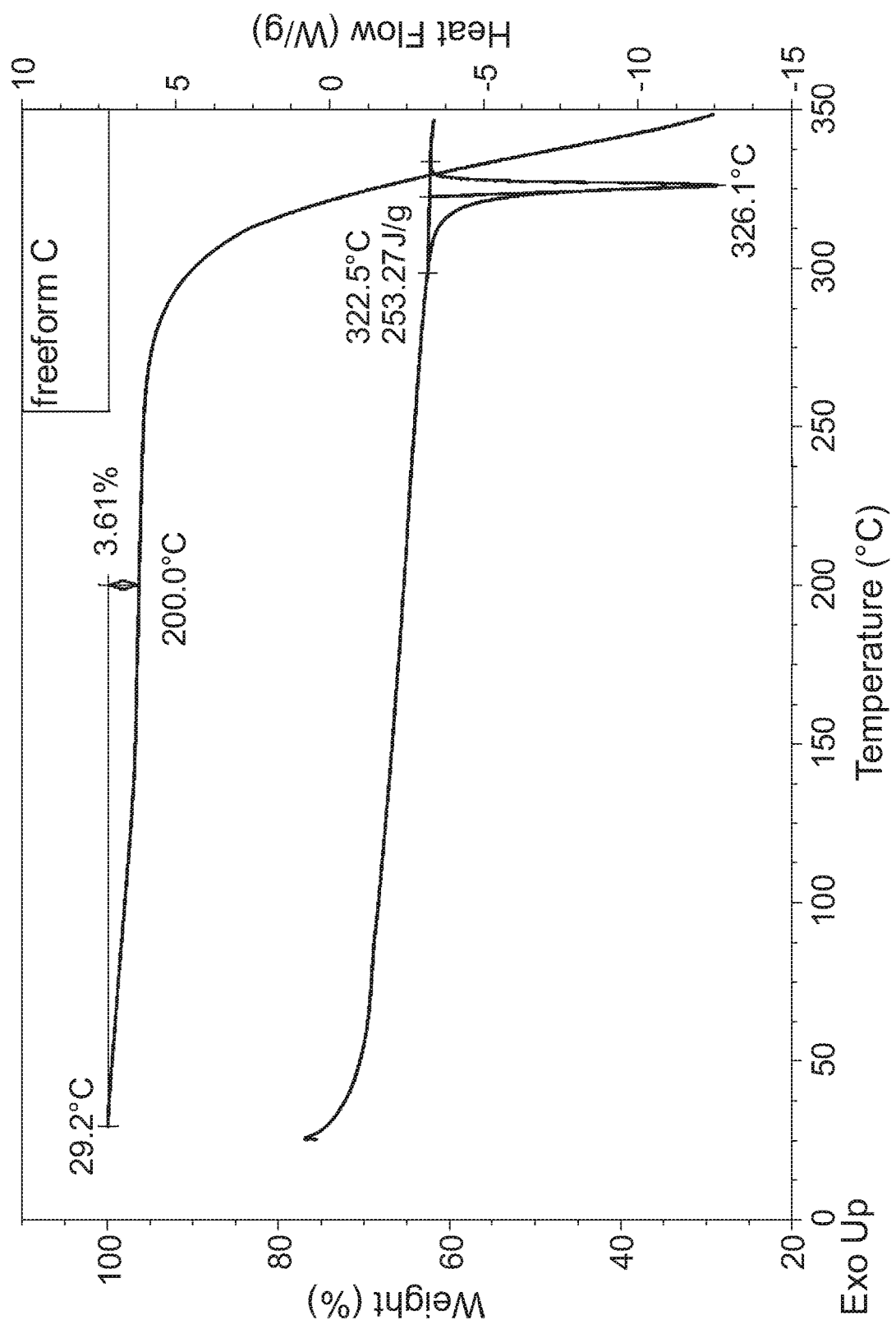
FIG. 4C depicts the combined DSC thermogram and TGA thermogram for the crystalline Form C of Compound 1.

In a forty-ninth embodiment, the crystalline Form C in accordance with any one of the forty-fourth, forty-fifth, forty-sixth, forty-seventh and forty-eighth embodiments is characterized by a differential scanning calorimetry (DSC) thermograph comprising an endotherm peak temperature at about 326.1° C.±2° C. (see FIG. 4C).

In a fiftieth embodiment, the crystalline Form C in accordance with any one of the forty-fourth, forty-fifth, forty-sixth, forty-seventh, forty-eighth and forty-ninth embodiments is characterized by a thermogravimetric analysis (TGA) thermogram comprising a weight loss of about 3.6% up to about 200° C. (see FIG. 4C).

In a fifty-first embodiment, the crystalline form in accordance with any one of the twenty-seventh and twenty-eighth embodiments is crystalline Form D characterized by X-ray powder diffraction peaks at 2θ angles (±0.2°) 5.9°, 11.9°, and 17.1°.

In a fifty-second embodiment, the crystalline form in accordance with any one of the twenty-seventh, twenty-eighth and twenty-ninth embodiments is crystalline Form D characterized by major X-ray powder diffraction peaks at 2θ angles (±0.2°) 5.9°, 11.9°, and 17.1°.

In a fifty-third embodiment, the crystalline Form D in accordance with any one of the fifty-first and fifty-second embodiments is further characterized by an X-ray powder diffraction peaks at 2θ angle (±0.2°) 11.2° and 23.3°.

In a fifty-fourth embodiment, the crystalline Form D in accordance with any one of the fifty-first, fifty-second and fifty-third embodiments is further characterized by at least one X-ray powder diffraction peak at 2θ angles (±0.2°) selected from 12.7°, 13.4°, 18.8°, 19.7°, 20.8°, 22.0°, 22.5°, 22.7° and 24.6°.

Figures 5A, 5B:
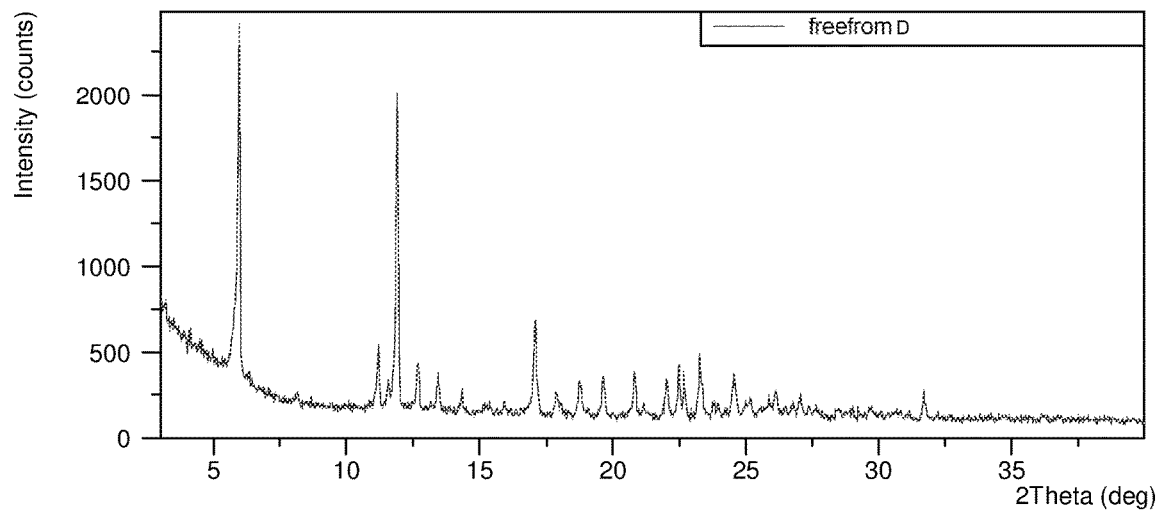
FIG. 5A depicts the XRPD pattern for crystalline form D of Compound 1.
FIG. 5B is an XRPD peak list for the crystalline form D of Compound 1.

In a fifty-fifth embodiment, the crystalline Form D in accordance with any one of the fifty-first, fifty-second, fifty-third and fifty-fourth embodiments is characterized by an X-ray powder diffraction pattern substantially similar to FIG. 5A, and XRPD peaks as listed in FIG. 5B.

Figure 5C:
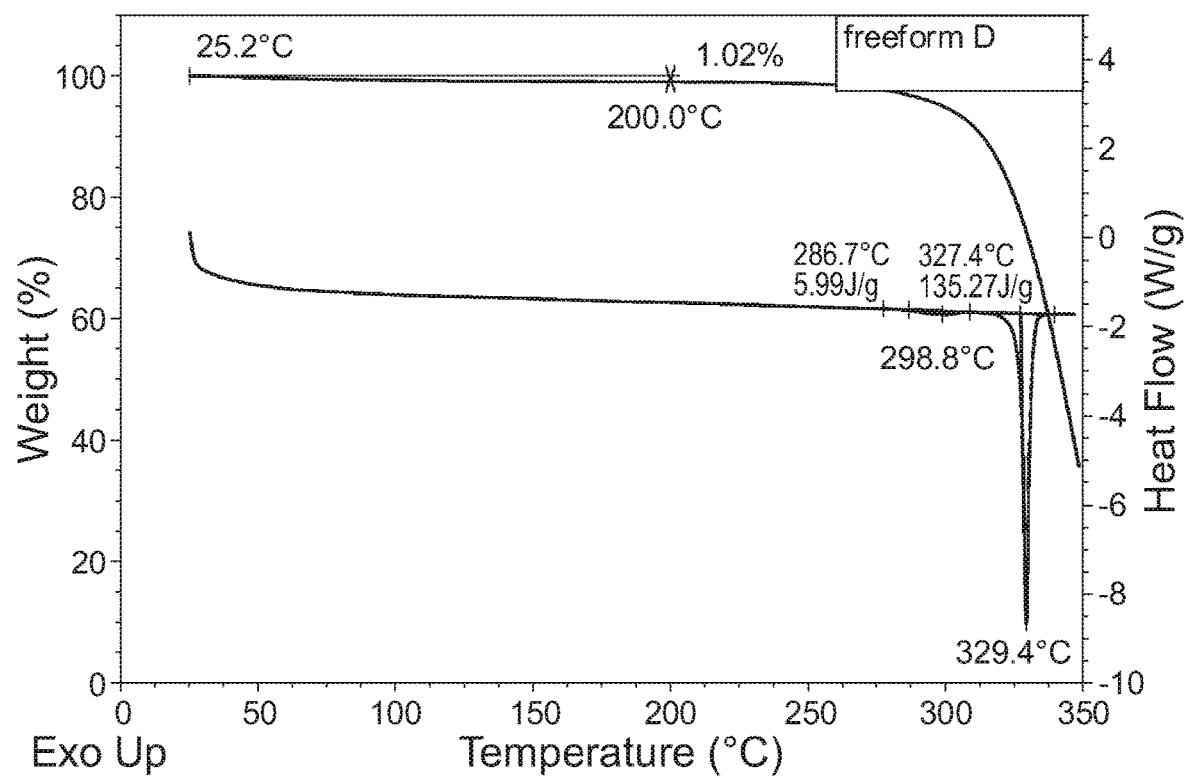
FIG. 5C depicts the combined DSC thermogram and TGA thermogram for the crystalline form D of Compound 1.

In a fifty-sixth embodiment, the crystalline Form D in accordance with any one of the fifty-first, fifty-second, fifty-third, fifty-fourth and fifty-fifth embodiments is characterized by a differential scanning calorimetry (DSC) thermograph comprising an endotherm peak temperature at about 329.4° C.±2° C. (see FIG. 5C).

In a fifty-seventh embodiment, the crystalline Form D in accordance with any one of the fifty-first, fifty-second, fifty-third, fifty-fourth, fifty-fifth and fifty-sixth embodiments is characterized by a thermogravimetric analysis (TGA) thermogram comprising a weight loss of about 1.0% up to about 200° C. (see FIG. 5C).

In a fifty-eighth embodiment, the crystalline form in accordance with any one of the twenty-seventh through fifty-seventh embodiments is at least 60% a single crystalline form, at least 70% a single crystalline form, at least 80% a single crystalline form, at least 90% a single crystalline form, at least 95% a single crystalline form, or at least 99% a single crystalline form by weight.

In a fifty-ninth embodiment, the crystalline form in accordance with any one of the twenty-seventh through fifty-eighth embodiments has a chemical purity of at least 60%, at least 70%, at least 80%, at least 90%, at least 95%, or at least 99% by weight.

Another embodiment of the invention is Compound 1 or the Tris salt of Compound 1 in amorphous form.

Compositions and Administration

Provided herein are pharmaceutical compositions comprising: i) the Tris salt of Compound 1, e.g., in amorphous form or in one of the disclosed crystalline forms of the Tris salt; or ii) one of the disclosed crystalline forms of Compound 1; or iii) the amorphous form of Compound 1; or iv) the sodium salt of Compound 1; or v) a pharmaceutically acceptable salt of Compound 1, and a pharmaceutically acceptable carrier. Also provided are pharmaceutical compositions comprising: i) the Tris salt of Compound 1, e.g., in amorphous form or in one of the disclosed crystalline forms of the Tris salt; or ii) one of the disclosed crystalline forms of Compound 1; or iii) the amorphous form of Compound 1; or iv) the sodium salt of Compound 1; or v) a pharmaceutically acceptable salt of Compound 1, as an active agent, and one or more intragranular excipients. Also provided are pharmaceutical compositions comprising: i) the Tris salt of Compound 1, e.g., in amorphous form or in one of the disclosed crystalline forms of the Tris salt; or ii) one of the disclosed crystalline forms of Compound 1; or iii) the amorphous form of Compound 1; or iv) the sodium salt of Compound 1; or v) a pharmaceutically acceptable salt of Compound 1, as an active agent, and one or more intragranular excipients and one or more extragranular excipients. Also provided are compositions comprising: i) the Tris salt of Compound 1, e.g., in amorphous form or in one of the disclosed crystalline forms of the Tris salt; or ii) one of the disclosed crystalline forms of Compound 1; or iii) the amorphous form of Compound 1; or iv) the sodium salt of Compound 1; or v) a pharmaceutically acceptable salt of Compound 1, as part of a solid dispersion. In some embodiments such compositions comprise an amorphous solid dispersion. In other embodiments such compositions comprise a substantially amorphous solid dispersion. In still other embodiments such compositions comprise a partially crystalline solid dispersion. In still other embodiments such compositions comprise a substantially crystalline solid dispersion. Also provided are pharmaceutical compositions, comprising: i) the Tris salt of Compound 1, e.g., in amorphous form or in one of the disclosed crystalline forms of the Tris salt; or ii) one of the disclosed crystalline forms of Compound 1; or iii) the amorphous form of Compound 1; or iv) the sodium salt of Compound 1 or v) a pharmaceutically acceptable salt, as part of a solid dispersion, and one or more pharmaceutically acceptable carrier(s). Suitable pharmaceutical compositions are described in U.S. Pat. No. 9,360,932 and below.

Compositions described herein may be administered orally, parenterally, by inhalation spray, topically, rectally, nasally, buccally, transmucosally, or in an ophthalmic preparation. The term "parenteral" as used herein includes subcutaneous, intravenous, intramuscular, intra-articular, intrasynovial, intrasternal, intrathecal, intrahepatic, intralesional and intracranial injection or infusion techniques. In one aspect, the pharmaceutical compositions provided herewith are orally administered in an orally acceptable dosage form including, but not limited to, capsules, tablets, emulsions and aqueous suspensions, dispersions and solutions.

The amount of provided crystalline or amorphous form that may be combined with carrier materials to produce a composition in a single dosage form will vary depending upon the subject to be treated and the particular mode of administration. For example, a specific dosage and treatment regimen for any particular subject will depend upon a variety of factors, including age, body weight, general health, sex, diet, time of administration, rate of excretion, drug combination, the judgment of the treating physician, and the severity of the particular disease being treated. The amount of a provided crystalline form in the composition will also depend upon the particular form (e.g., Form A, B, C, D of the crystalline form of Compound 1 or Form A, B, C of the Tris salt form of Compound 1) in the composition. In one aspect, a provided composition may be formulated such that a dosage equivalent is about 0.001 to about 100 mg/kg body weight/day of Compound 1.

In one embodiment, the pharmaceutical composition comprises: i) Compound 1 or a pharmaceutically acceptable salt thereof; ii) a diluent; iii) a disintegrant; and iv) a lubricant. In another embodiment, the pharmaceutical composition comprises: i) Compound 1 or a pharmaceutically acceptable salt thereof; ii) a diluent; iii) a disintegrant; iv) a binder; v) a surfactant; vi) a glidant; and vii) a lubricant. In another embodiment, the pharmaceutical composition comprises: i) Compound 1 or a pharmaceutically acceptable salt thereof; ii) a diluent; iii) a disintegrant; iv) a binder; and v) a lubricant. In such compositions, Compound 1 can be provided as, for example: i) one of the disclosed crystalline forms of Compound 1; or ii) the amorphous form of Compound 1 or iii) as a mixture thereof. In other embodiments of such compositions, Compound 1 can be provided as the Tris salt of Compound 1 for example: i) in amorphous form; or ii) in one of the disclosed crystalline forms of the Tris salt or iii) as a mixture thereof. In still other embodiments of such pharmaceutical compositions, Compound 1 can be provided in a non-salt form or as a Tris salt form or as a mixture thereof. In one aspect, the pharmaceutical composition is in the form of a capsule. In another aspect, the pharmaceutical composition is in the form of a tablet.

In certain embodiments, the pharmaceutical composition is a capsule composition comprising a crystalline form of Compound 1 as an active agent, and one or more intragranular excipients. In one embodiment, the capsule composition comprises Form A of Compound 1 as an active agent, and one or more intragranular excipients. In one embodiment, the capsule composition comprises Form B of Compound 1 as an active agent, and one or more intragranular excipients. In one embodiment, the capsule composition comprises Form C of Compound 1 as an active agent, and one or more intragranular excipients. In one embodiment, the capsule composition comprises Form D of Compound 1 as an active agent, and one or more intragranular excipients.

In certain embodiments, the pharmaceutical composition is a capsule composition comprising a crystalline form of Compound 1 as an active agent, one or more intragranular excipients and one or more extragranular excipients. In one embodiment, the capsule composition comprises Form A of Compound 1 as an active agent, one or more intragranular excipients and one or more extragranular excipients. In one embodiment, the capsule composition comprises Form B of Compound 1 as an active agent, one or more intragranular excipients and one or more extragranular excipients. In one embodiment, the capsule composition comprises Form C of Compound 1 as an active agent, one or more intragranular excipients and one or more extragranular excipients. In one embodiment, the capsule composition comprises Form D of Compound 1 as an active agent, one or more intragranular excipients and one or more extragranular excipients.

In certain embodiments, the pharmaceutical composition is a capsule composition comprising the Tris salt of Compound 1 as an active agent, and one or more intragranular excipients. In one embodiment, the active agent used in the capsule compositions is one of the disclosed crystalline forms of the Tris salt of Compound 1. In one embodiment, the capsule composition comprises Tris salt Form A as an active agent, and one or more intragranular excipients. In one embodiment, the capsule composition comprises Tris salt Form B as an active agent, and one or more intragranular excipients. In one embodiment, the capsule composition comprises Tris salt Form C as an active agent, and one or more intragranular excipients.

In certain embodiments, the pharmaceutical composition is a capsule composition comprising the Tris salt of Compound 1 as an active agent, one or more intragranular excipients and one or more extragranular excipients. In one embodiment, the active agent used in the capsule compositions is one of the disclosed crystalline forms of the Tris salt of Compound 1. In one embodiment, the capsule composition comprises Tris salt Form A as an active agent, one or more intragranular excipients and one or more extragranular excipients. In one embodiment, the capsule composition comprises Tris salt Form B as an active agent, one or more intragranular excipients and one or more extragranular excipients. In one embodiment, the capsule composition comprises Tris salt Form C as an active agent, one or more intragranular excipients and one or more extragranular excipients.

In certain embodiments, the pharmaceutical composition is a capsule composition comprising the sodium salt of Compound 1 as an active agent, and one or more intragranular excipients. In certain embodiments, the pharmaceutical composition is a capsule composition comprising the sodium salt of Compound 1 as an active agent, one or more intragranular excipients and one or more extragranular excipients.

In certain embodiments, the pharmaceutical composition is a tablet composition comprising a crystalline form of Compound 1 as an active agent, and one or more intragranular excipients. In one embodiment, the tablet composition comprises Form A of Compound 1 as an active agent, and one or more intragranular excipients. In one embodiment, the tablet composition comprises Form B of Compound 1 as an active agent, and one or more intragranular excipients. In one embodiment, the tablet composition comprises Form C of Compound 1 as an active agent, and one or more intragranular excipients. In one embodiment, the tablet composition comprises Form D of Compound 1 as an active agent, and one or more intragranular excipients.

In certain embodiments, the pharmaceutical composition is a tablet composition comprising a crystalline form of Compound 1 as an active agent, one or more intragranular excipients and one or more extragranular excipients. In one embodiment, the tablet composition comprises Form A of Compound 1 as an active agent, one or more intragranular excipients and one or more extragranular excipients. In one embodiment, the tablet composition comprises Form B of Compound 1 as an active agent, one or more intragranular excipients and one or more extragranular excipients. In one embodiment, the tablet composition comprises Form C of Compound 1 as an active agent, one or more intragranular excipients and one or more extragranular excipients. In one embodiment, the tablet composition comprises Form D of Compound 1 as an active agent, one or more intragranular excipients and one or more extragranular excipients.

In certain embodiments, the pharmaceutical composition is a tablet composition comprising the Tris salt of Compound 1 as an active agent, and one or more intragranular excipients. In one embodiment, the active agent used in the tablet compositions is one of the disclosed crystalline forms of the Tris salt of Compound 1. In one embodiment, the tablet composition comprises Tris salt Form A as an active agent, and one or more intragranular excipients. In one embodiment, the tablet composition comprises Tris salt Form B as an active agent, and one or more intragranular excipients. In one embodiment, the tablet composition comprises Tris salt Form C as an active agent, and one or more intragranular excipients.

In certain embodiments, the pharmaceutical composition is a tablet composition comprising the Tris salt of Compound 1 as an active agent, one or more intragranular excipients and one or more extragranular excipients. In one embodiment, the active agent used in the tablet compositions is one of the disclosed crystalline forms of the Tris salt of Compound 1. In one embodiment, the tablet composition comprises Tris salt Form A as an active agent, one or more intragranular excipients and one or more extragranular excipients. In one embodiment, the tablet composition comprises Tris salt Form B as an active agent, one or more intragranular excipients and one or more extragranular excipients. In one embodiment, the tablet composition comprises Tris salt Form C as an active agent, one or more intragranular excipients and one or more extragranular excipients.

In certain embodiments, the pharmaceutical composition is a tablet composition comprising the sodium salt of Compound 1 as an active agent, and one or more intragranular excipients. In certain embodiments, the pharmaceutical composition is a tablet composition comprising the sodium salt of Compound 1 as an active agent, one or more intragranular excipients and one or more extragranular excipients.

In certain embodiments, the pharmaceutical compositions provided herein comprise Compound 1 or a pharmaceutically acceptable salt thereof in an amount from about 10% to about 90% by weight based on the total weight of the pharmaceutical composition (e.g., between about 20% w/w and about 80% w/w; between about 30% w/w and about 70% w/w; between about 40% w/w and about 60% w/w; or between about 10% and 20% w/w).

In certain embodiments, the pharmaceutical compositions provided herein comprise Compound 1 or a pharmaceutically acceptable salt thereof in an amount of from about 15% to about 65%; from about 45% to about 65%; or from about 15% to about 17% by weight based on the total weight of the pharmaceutical composition. In certain embodiments, the pharmaceutical compositions provided herein comprise Compound 1 or the Tris salt of Compound 1 in an amount of about 16%, about 45%, about 54%, or about 60% by weight based on the total weight of the pharmaceutical composition. In certain embodiments, the pharmaceutical compositions provided herein comprise Compound 1 or the Tris salt of Compound 1 in an amount of about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, or about 65% by weight based on the total weight of the pharmaceutical composition. In certain embodiments, the Tris salt of Compound 1 is Tris salt Form C.

In certain embodiments, the pharmaceutical compositions provided herein may comprise one or more intragranular excipients and one or more extragranular excipients. In certain embodiments, the intragranular excipients comprise a diluent, a disintegrant, a binder, a surfactant, a glidant, and a lubricant. In certain embodiments, the intragranular excipients comprise a diluent, a disintegrant, a binder, a surfactant, and a lubricant. In certain embodiments, the intragranular excipients comprise a diluent, a disintegrant, a binder, a glidant, and a lubricant. In certain embodiments, the intragranular excipients comprise a diluent, a disintegrant, a binder, and a lubricant. In certain embodiments, the intragranular excipients comprise a diluent, a disintegrant, and a lubricant. In certain embodiments, the extragranular excipients comprise a glidant and a lubricant. In certain embodiments, the extragranular excipients comprise a glidant. In certain embodiments, the extragranular excipients comprise a lubricant. In certain embodiments, no extragranular excipients are used. In other embodiments, no intragranular or extragranular excipients are used.

1. Intragranular Excipients

In one embodiment, the pharmaceutical compositions provided herein comprise one or more intragranular excipients selected from a diluent, a disintegrant, a binder, a surfactant, a glidant, and a lubricant.

Diluents are excipients used in pharmaceutical formulations in various amounts to help increase weight and aid in flowability, solubility, content uniformity, encapsulation, compressibility, decreasing tackiness, and imparting stability. It should be understood that as used herein, unless stated expressly to the contrary that the terms diluent(s), filler(s) or bulking agent(s) are used interchangeably. Exemplary diluents include calcium carbonate, sodium carbonate, calcium phosphate, dicalcium phosphate, calcium sulfate, calcium hydrogen phosphate, sodium phosphate, lactose, sucrose, cellulose, microcrystalline cellulose, kaolin, mannitol, sorbitol, inositol, sodium chloride, starch, pregelatinized starch, cornstarch, partially pregelatinized starch, powdered sugar, ethyl cellulose, isomalt, and mixtures thereof. In some embodiments, the diluents are starch, partially pregelatinized starch, microcrystalline cellulose, and mannitol, and mixtures thereof. In some embodiments, the diluents are dicalcium phosphate, starch, lactose, isomalt, and mixtures thereof. In some embodiments, the diluents are microcrystalline cellulose and mannitol and mixtures thereof. In some embodiments, the diluent is microcrystalline cellulose. In some embodiments, the diluent is mannitol. In some embodiments, the diluent is starch. In some embodiments, the diluent is partially pregelatinized starch.

In certain embodiments, the pharmaceutical composition comprises a diluent (or one or more diluents) in an amount of about 5 to about 80% by weight based on the total weight of the pharmaceutical composition (e.g., between about 10% w/w and about 75% w/w; between about 15% w/w and about 70% w/w; between about 25% w/w and about 65% w/w; between about 30% w/w and about 60% w/w; between about 35% w/w and about 55% w/w; between about 40% w/w and about 50% w/w). In certain embodiments, the pharmaceutical composition comprises a diluent (or one or more diluents) in an amount of from about 5% to about 15%; about 5% to about 45%; about 25% to about 45%; or from about 25% to about 80% by weight based on the total weight of the pharmaceutical composition. In certain embodiments, the pharmaceutical composition comprises a diluent (or one or more diluents) in an amount of about 5%, about 6%, about 8%, about 9%, about 10%, about 11%, about 15%, about 20%, about 21%, about 22%, about 23%, about 24%, about 25%, about 27%, about 28%, about 30%, about 31%, about 32%, about 33%, about 34%, about 35%, about 37%, about 40%, about 41%, about 42%, about 45%, about 50%, about 55%, about 60%, about 65%, about 70%, about 75%, about 78%, about 79%, or about 80% by weight based on the total weight of the pharmaceutical composition.

In certain embodiments, the pharmaceutical composition comprises microcrystalline cellulose in an amount of about 5% to about 80% by weight based on the total weight of the pharmaceutical composition, such as for example from about 5% to about 15%, from about 20% to about 40%, or from about 20% to about 80% by weight based on the total weight of the pharmaceutical composition. In certain embodiments, the pharmaceutical composition comprises microcrystalline cellulose in an amount of about 5%, about 6%, about 7%, about 8%, about 9%, about 10%, about 11%, about 12%, about 13%, about 14%, about 15%, about 20%, about 21%, about 22%, about 23%, about 24%, about 25%, about 27%, about 28%, about 30%, about 31%, about 32%, about 33%, about 34%, about 35%, about 37%, about 40%, about 41%, about 42%, about 45%, about 50%, about 55%, about 60%, about 65%, about 70%, about 75%, about 78%, about 79%, or about 80% by weight based on the total weight of the pharmaceutical composition.

In certain embodiments, the pharmaceutical composition comprises mannitol in an amount of about 5% to 80% by weight based on the total weight of the pharmaceutical composition, such as for example from about 5% to about 15%, from about 20% to about 40%, or from about 20% to about 80% by weight based on the total weight of the pharmaceutical composition. In certain embodiments, the pharmaceutical composition comprises mannitol in an amount of about 5%, about 6%, about 7%, about 8%, about 9%, about 10%, about 11%, about 12%, about 13%, about 14%, or about 15%, about 20%, about 21%, about 22%, about 23%, about 24%, about 25%, about 27%, about 28%, about 30%, about 31%, about 32%, about 33%, about 34%, about 35%, about 37%, about 40%, about 41%, about 42%, about 45%, about 50%, about 55%, about 60%, about 65%, about 70%, about 75%, about 78%, about 79%, or about 80% by weight based on the total weight of the pharmaceutical composition.

In certain embodiments, the pharmaceutical composition comprises starch in an amount of about 5% to about 80% by weight based on the total weight of the pharmaceutical composition, such as for example from about 5% to about 15%, from about 20% to about 40%, or from about 20% to about 80% by weight based on the total weight of the pharmaceutical composition. In certain embodiments, the pharmaceutical composition comprises starch in an amount of about 5%, about 6%, about 7%, about 8%, about 9%, about 10%, about 11%, about 12%, about 13%, about 14%, or about 15%, about 20%, about 21%, about 22%, about 23%, about 24%, about 25%, about 27%, about 28%, about 30%, about 31%, about 32%, about 33%, about 34%, about 35%, about 37%, about 40%, about 41%, about 42%, about 45%, about 50%, about 55%, about 60%, about 65%, about 70%, about 75%, about 78%, about 79%, or about 80% by weight based on the total weight of the pharmaceutical composition.

In certain embodiments, the pharmaceutical composition comprises partially pregelatinized starch in an amount of about 5% to about 80% by weight based on the total weight of the pharmaceutical composition, such as for example from about 5% to about 15%, from about 20% to about 40%, or from about 20% to about 80% by weight based on the total weight of the pharmaceutical composition. In certain embodiments, the pharmaceutical composition comprises partially pregelatinized starch in an amount of about 5%, about 6%, about 7%, about 8%, about 9%, about 10%, about 11%, about 12%, about 13%, about 14%, or about 15%, about 20%, about 21%, about 22%, about 23%, about 24%, about 25%, about 27%, about 28%, about 30%, about 31%, about 32%, about 33%, about 34%, about 35%, about 37%, about 40%, about 41%, about 42%, about 45%, about 50%, about 55%, about 60%, about 65%, about 70%, about 75%, about 78%, about 79%, or about 80% by weight based on the total weight of the pharmaceutical composition.

Disintegrants are excipients that are used to improve the disintegration of a pharmaceutical preparation, more particularly, they are excipients to be added to disintegrate a capsule or tablet by absorbing fluids in the body after administration, swelling, and thereby facilitating release of the active ingredient. In certain embodiments, the amount of disintegrants in the capsules and tablets provided herein is selected such that the rate of disintegration and/or rate of the dissolution of the capsule or tablet fall within a desired range. In certain embodiments, the amount of disintegrant in the capsule or tablet is about 10% by weight or less based on the total weight of the capsule or tablet.

Exemplary disintegrants include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof. In one embodiment, the disintegrant comprises crospovidone, sodium starch glycolate, croscarmellose sodium and mixtures thereof. In one embodiment, the disintegrant is crospovidone. In one embodiment, the disintegrant is sodium starch glycolate. In one embodiment, the disintegrant is croscarmellose sodium.

In certain embodiments, the amount of disintegrant in the pharmaceutical composition is from about 0.5% to about 8%, such as for example from about 0.5% to about 5% or from about 2% to about 5% by weight based on the total weight of the pharmaceutical composition. In one embodiment, the amount of the disintegrant is the pharmaceutical composition is from about 2% to about 4% by weight based on the total weight of the pharmaceutical composition. In one embodiment, the disintegrant is present in the pharmaceutical composition in an amount of about 3% by weight based on the total weight of the pharmaceutical composition. In one embodiment, the disintegrant is present in the pharmaceutical composition in an amount of about 4% by weight based on the total weight of the pharmaceutical composition. In one embodiment, the disintegrant is present in the pharmaceutical composition in an amount of about 5% by weight based on the total weight of the pharmaceutical composition.

In certain embodiments, the pharmaceutical composition comprises crospovidone in an amount of from about 0.5% to about 8%, such as for example from about 0.5% to about 5% or about 2% to about 5% by weight based on the total weight of the pharmaceutical composition. In one embodiment, the pharmaceutical composition comprises crospovidone in an amount of about 2% to about 4% by weight based on the total weight of the pharmaceutical composition. In one embodiment, the pharmaceutical composition comprises crospovidone in an amount of about 3% by weight based on the total weight of the pharmaceutical composition. In one embodiment, the pharmaceutical composition comprises crospovidone in an amount of about 4% by weight based on the total weight of the pharmaceutical composition. In one embodiment, the pharmaceutical composition comprises crospovidone in an amount of about 5% by weight based on the total weight of the pharmaceutical composition.

In certain embodiments, the pharmaceutical composition comprises sodium starch glycolate in an amount of from about 0.5% to about 8%, such as for example from about 0.5% to about 5% or about 2% to about 5% by weight based on the total weight of the pharmaceutical composition. In one embodiment, the pharmaceutical composition comprises sodium starch glycolate in an amount of about 2% to about 4% by weight based on the total weight of the pharmaceutical composition. In one embodiment, the pharmaceutical composition comprises sodium starch glycolate in an amount of about 3% by weight based on the total weight of the pharmaceutical composition. In one embodiment, the pharmaceutical composition comprises sodium starch glycolate in an amount of about 4% by weight based on the total weight of the pharmaceutical composition. In one embodiment, the pharmaceutical composition comprises sodium starch glycolate in an amount of about 5% by weight based on the total weight of the pharmaceutical composition.

In certain embodiments, the pharmaceutical composition comprises croscarmellose sodium in an amount of from about 0.5% to about 8%, such as for example from about 0.5% to about 5% or about 2% to about 5% by weight based on the total weight of the pharmaceutical composition. In one embodiment, the pharmaceutical composition comprises croscarmellose sodium in an amount of about 2% to about 4% by weight based on the total weight of the pharmaceutical composition. In one embodiment, the pharmaceutical composition comprises croscarmellose sodium in an amount of about 3% by weight based on the total weight of the pharmaceutical composition. In one embodiment, the pharmaceutical composition comprises croscarmellose sodium in an amount of about 4% by weight based on the total weight of the pharmaceutical composition. In one embodiment, the pharmaceutical composition comprises croscarmellose sodium in an amount of about 5% by weight based on the total weight of the pharmaceutical composition.

Binders are classified as excipients which impart the cohesiveness required for manufacturability of solid oral dosage forms. The amount of a binder in tablets or capsules provided herein varies based on, for example, the type of binders (properties such as molecular weight, solubility, and viscosity), the type and amount of other excipients, the type and amount of the composite, and its dosage form, and the formulation (granulation method and tableting method).

Exemplary binders include hydroxypropyl cellulose, hypromellose, hypromellose acetate succinate, methyl cellulose, hydroxyethyl cellulose, hydroxyethyl methylcellulose, hydroxypropyl starch, povidone, corn starch, potato starch, rice starch, and gelatin, and mixtures thereof. In one embodiment, the binder comprises hypromellose, povidone, methyl cellulose, hydroxypropyl cellulose, polyvinylpyrrolidone/vinyl acetate (PVPVA), hydroxypropyl methylcellulose acetate succinate (HPMCAS), and mixtures thereof. In one embodiment, the binder comprises hypromellose. In one embodiment, the binder comprises povidone (PVPK-30). In one embodiment, the binder comprises methyl cellulose. In one embodiment, the binder comprises hydroxypropyl cellulose. In one embodiment, the binder comprises polyvinylpyrrolidone/vinyl acetate (PVPVA). In one embodiment, the binder comprises hydroxypropyl methylcellulose acetate succinate (HPMCAS).

In certain embodiments, the pharmaceutical composition comprises a binder in an amount of about 0.5% to about 10% by weight based on the total weight of the pharmaceutical composition. In certain embodiments, the pharmaceutical composition comprises a binder in an amount from about 0.5% to about 5%, from about 2% to about 8%, or from about 2% to about 5% by weight based on the total weight of the pharmaceutical composition. In certain embodiments, the pharmaceutical composition comprises a binder in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises hypromellose in an amount from about 0.5% to about 10% by weight based on the total weight of the pharmaceutical composition. In certain embodiments, the pharmaceutical composition comprises hypromellose in an amount from about 0.5% to about 5%, from about 2% to about 8%, or from about 2% to about 5% by weight based on the total weight of the pharmaceutical composition. In certain embodiments, the pharmaceutical composition comprises hypromellose in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises povidone in an amount from about 0.5% to about 10% by weight based on the total weight of the pharmaceutical composition. In certain embodiments, the pharmaceutical composition comprises povidone in an amount from about 0.5% to about 5%, from about 2% to about 8%, or from about 2% to about 5% by weight based on the total weight of the pharmaceutical composition. In certain embodiments, the pharmaceutical composition comprises povidone in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises methyl cellulose in an amount from about 0.5% to about 10% by weight based on the total weight of the pharmaceutical composition. In certain embodiments, the pharmaceutical composition comprises methyl cellulose in an amount from about 0.5% to about 5%, from about 2% to about 8%, or from about 2% to about 5% by weight based on the total weight of the pharmaceutical composition. In certain embodiments, the pharmaceutical composition comprises methyl cellulose in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises hydroxypropyl cellulose in an amount from about 0.5% to about 10% by weight based on the total weight of the pharmaceutical composition. In certain embodiments, the pharmaceutical composition comprises hydroxypropyl cellulose in an amount from about 0.5% to about 5%, from about 2% to about 8%, or from about 2% to about 5% by weight based on the total weight of the pharmaceutical composition. In certain embodiments, the pharmaceutical composition comprises hydroxypropyl cellulose in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises polyvinylpyrrolidone/vinyl acetate (PVPVA) in an amount from about 0.5% to about 10% by weight based on the total weight of the pharmaceutical composition. In certain embodiments, the pharmaceutical composition comprises PVPVA in an amount from about 0.5% to about 5%, from about 2% to about 8%, or from about 2% to about 5% by weight based on the total weight of the pharmaceutical composition. In certain embodiments, the pharmaceutical composition comprises PVPVA in an amount of about 1%, about 2%, about 3%, about 4%, about 5%, about 6%, about 7%, about 8%, about 9%, or about 10% by weight based on the total weight of the pharmaceutical composition.

In certain embodiments, the pharmaceutical composition comprises hydroxypropyl methylcellulose acetate succinate (HPMCAS) in an amount from about 0.5% to about 10% by weight based on the total weight of the pharmaceutical composition. In certain embodiments, the pharmaceutical composition comprises HPMCAS in an amount from about 0.5% to about 5%, from about 2% to about 8%, or from about 2% to about 5% by weight based on the total weight of the pharmaceutical composition. In certain embodiments, the pharmaceutical composition comprises HPMCAS in an amount of about 1%, about 2%, about 3%, about 4%, about 5%, about 6%, about 7%, about 8%, about 9%, or about 10% by weight based on the total weight of the pharmaceutical composition.

In some embodiments, the pharmaceutical composition also includes a glidant, which is an excipient used in solid oral dosage forms to increase the flowability of a powder. Exemplary glidants include silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide, starch, and talc. In one embodiment, the glidant is colloidal silicon dioxide. In one embodiment, the glidant is starch. In one embodiment, the glidant is talc.

In certain embodiments, the glidant is present in an amount from about 0.1% to about 2% by weight based on the total weight of the pharmaceutical composition. In certain embodiments, the amount of the glidant is from about 0.1% to about 1%, from about 0.25% to about 1.5%, or from about 0.5% to about 1.0% by weight based on the total weight of the pharmaceutical composition. In one embodiment, the amount of the glidant is about 0.5%, about 0.75%, about 1%, or about 1.5% by weight based on the total weight of the pharmaceutical composition.

In certain embodiments, the pharmaceutical composition comprises colloidal silicon dioxide in an amount of from about 0.1% to about 2%; from about 0.1% to about 1%, from about 0.25% to about 1.5%; or from about 0.5% to about 1.0% by weight based on the total weight of the pharmaceutical composition. In one embodiment, the pharmaceutical composition comprises colloidal silicon dioxide in an amount of about 0.5%, about 0.75%, about 1%, or about 1.5% by weight based on the total weight of the pharmaceutical composition.

In certain embodiments, the pharmaceutical composition comprises starch in an amount of from about 0.1% to about 2%; from about 0.1% to about 1%, from about 0.25% to about 1.5%; or from about 0.5% to about 1.0% by weight based on the total weight of the pharmaceutical composition. In one embodiment, the pharmaceutical composition comprises starch in an amount of about 0.5%, about 0.75%, about 1%, or about 1.5% by weight based on the total weight of the pharmaceutical composition.

In certain embodiments, the pharmaceutical composition comprises talc in an amount of from about 0.1% to about 2%; from about 0.1% to about 1%, from about 0.25% to about 1.5%; or from about 0.5% to about 1.0% by weight based on the total weight of the pharmaceutical composition.

In one embodiment, the pharmaceutical composition comprises talc in the intragranular excipients in an amount of about 0.5%, about 0.75%, about 1%, or about 1.5% by weight based on the total weight of the pharmaceutical composition.

In some embodiments, the pharmaceutical composition also includes a lubricating agent, which is an excipient that reduces interparticle friction and sticking/adhesion to tablet punches and dies. Exemplary lubricating agents include magnesium stearate (vegetable grade), calcium stearate, zinc stearate, sucrose stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, sodium stearyl fumarate, polyvinyl alcohol, magnesium lauryl sulfate, and mixtures thereof. In certain embodiments, the lubricant is sodium stearyl fumarate, magnesium stearate, talc, silica, stearic acid, and glyceryl behenate. In one embodiment, the lubricant is sodium stearyl fumarate. In one embodiment, the lubricant is magnesium stearate. In one embodiment, the lubricant is talc. In one embodiment, the lubricant is silica. In one embodiment, the lubricant is stearic acid. In one embodiment, the lubricant is glyceryl behenate.

In certain embodiments, the lubricating agent is present in an amount from about 0.25% to about 3% by weight based on the total weight of the pharmaceutical composition. In certain embodiments, the amount of the lubricating agent is from about 0.5% to about 2% or from about 0.75% to about 1.5% by weight based on the total weight of the pharmaceutical composition. In certain embodiments, the amount of the lubricating agent is about 0.5%, about 0.75%, about 1%, about 1.25%, about 1.5%, about 1.75%, or about 2% by weight based on the total weight of the pharmaceutical composition.

In certain embodiments, the pharmaceutical composition comprises sodium stearyl fumarate in an amount of from about 0.25% to about 3%; from about 0.5% to about 2%; or from about 0.75% to about 1.5% by weight based on the total weight of the pharmaceutical composition. In certain embodiments, the pharmaceutical composition comprises sodium stearyl fumarate in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises magnesium stearate in an amount of from about 0.25% to about 3%; from about 0.5% to about 2%; or from about 0.75% to about 1.5% by weight based on the total weight of the pharmaceutical composition. In certain embodiments, the pharmaceutical composition comprises magnesium stearate in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises talc in an amount of from about 0.25% to about 3%; from about 0.5% to about 2%; or from about 0.75% to about 1.5% by weight based on the total weight of the pharmaceutical composition. In certain embodiments, the pharmaceutical composition comprises talc in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises silica in an amount of from about 0.25% to about 3%; from about 0.5% to about 2%; or from about 0.75% to about 1.5% by weight based on the total weight of the pharmaceutical composition. In certain embodiments, the pharmaceutical composition comprises silica in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises stearic acid in an amount of from about 0.25% to about 3%; from about 0.5% to about 2%; or from about 0.75% to about 1.5% by weight based on the total weight of the pharmaceutical composition. In certain embodiments, the pharmaceutical composition comprises stearic acid in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises glyceryl behenate in an amount of from about 0.25% to about 3%; from about 0.5% to about 2%; or from about 0.75% to about 1.5% by weight based on the total weight of the pharmaceutical composition. In certain embodiments, the pharmaceutical composition comprises glyceryl behenate in an amount of about 0.5%, about 0.75%, about 1%, about 1.25%, about 1.5%, about 1.75%, or about 2% by weight based on the total weight of the pharmaceutical composition.

Surfactants or wetting agents are excipients to improve wetting properties and help in the solubilization of an active agent. Exemplary surfactants and wetting agents include sodium lauryl sulfate (SLS), vitamin E or a derivative thereof (e.g., vitamin E TPGS), docusate sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is sodium lauryl sulfate, poloxamers, pluronic copolymers, and polysorbates. In one embodiment, the surfactant is sodium lauryl sulfate. In one embodiment, the surfactant is a poloxamer. In one embodiment, the surfactant is a pluronic copolymer. In one embodiment, the surfactant is a polysorbate.

In certain embodiments, the surfactant is present in an amount from about 0.1% to about 3% by weight based on the total weight of the pharmaceutical composition. In one embodiment, the amount of the surfactant is from about 0.5% to about 1.5% or from about 1% to about 2% by weight based on the total weight of the pharmaceutical composition. In some embodiments, the surfactant is present in an amount of about 0.5%, about 1%, about 1.5%, or about 2% by weight based on the total weight of the pharmaceutical composition.

In certain embodiments, the pharmaceutical composition comprises sodium lauryl sulfate in an amount from about 0.1% to about 3% by weight based on the total weight of the pharmaceutical composition. In one embodiment, the pharmaceutical composition comprises sodium lauryl sulfate in an amount of about 0.5% to about 1.5% or about 1% to about 2% by weight based on the total weight of the pharmaceutical composition. In some embodiments, the pharmaceutical composition comprises sodium lauryl sulfate in an amount of about 0.5%, about 1%, about 1.5%, or about 2% by weight based on the total weight of the pharmaceutical composition.

In certain embodiments, the pharmaceutical composition comprises a poloxamer in an amount from about 0.1% to about 3% by weight based on the total weight of the pharmaceutical composition. In one embodiment, the pharmaceutical composition comprises a poloxamer in an amount of about 0.5% to about 1.5% or about 1% to about 2% by weight based on the total weight of the pharmaceutical composition. In some embodiments, the pharmaceutical composition comprises a poloxamer in an amount of about 0.5%, about 1%, about 1.5%, or about 2% by weight based on the total weight of the pharmaceutical composition.

In certain embodiments, the pharmaceutical composition comprises a pluronic copolymer in an amount from about 0.1% to about 3% by weight based on the total weight of the pharmaceutical composition. In one embodiment, the pharmaceutical composition comprises a pluronic copolymer in an amount of about 0.5% to about 1.5% or about 1% to about 2% by weight based on the total weight of the pharmaceutical composition. In some embodiments, the pharmaceutical composition comprises a pluronic copolymer in an amount of about 0.5%, about 1%, about 1.5%, or about 2% by weight based on the total weight of the pharmaceutical composition.

In certain embodiments, the pharmaceutical composition comprises a polysorbate in an amount from about 0.1% to about 3% by weight based on the total weight of the pharmaceutical composition. In one embodiment, the pharmaceutical composition comprises a polysorbate in an amount of about 0.5% to about 1.5% or about 1% to about 2% by weight based on the total weight of the pharmaceutical composition. In some embodiments, the pharmaceutical composition comprises a polysorbate in an amount of about 0.5%, about 1%, about 1.5%, or about 2% by weight based on the total weight of the pharmaceutical composition.

The pharmaceutical compositions provided herein may also contain one or more additional pharmaceutically acceptable intragranular excipients other than the above-mentioned excipients. Examples of such additional excipients include, but are not limited to, solubility enhancers, stabilizers, pH adjustors, coating agents, and pigments.

In certain embodiments, the pharmaceutical compositions provided herein are in tablet form and may comprise a coating agent, such as, for example polyvinyl alcohol.

In certain embodiments, the pharmaceutical compositions provided herein are in tablet form and may comprise a pigment, such as, for example titanium dioxide.

2. Extragranular Excipients

In certain embodiments, the pharmaceutical compositions provided herein comprise one or more extragranular excipients selected from a glidant and a lubricant.

In certain embodiments, the glidant used in the extragranular excipients is colloidal silicon dioxide, starch, and talc. In one embodiment, the glidant is colloidal silicon dioxide. In one embodiment, the glidant is starch. In one embodiment, the glidant is talc.

In some embodiments, the glidant is present in the extragranular excipients in an amount from about 0.1% to about 2% by weight based on the total weight of the pharmaceutical composition. In certain embodiments, the amount of the glidant in the extragranular excipients is from about 0.1% to about 1%, from about 0.25% to about 1.5%, or from about 0.5% to about 1.0% by weight based on the total weight of the pharmaceutical composition. In one embodiment, the amount of the glidant in the extragranular excipients is about 0.5%, about 0.75%, or about 1% by weight based on the total weight of the pharmaceutical composition.

In certain embodiments, the pharmaceutical composition comprises colloidal silicon dioxide in the extragranular excipients in an amount of from about 0.1% to about 2%; from about 0.1% to about 1%, from about 0.25% to about 1.5%; or from about 0.5% to about 1.0% by weight based on the total weight of the pharmaceutical composition. In one embodiment, the pharmaceutical composition comprises colloidal silicon dioxide in the extragranular excipients in an amount of about 0.5%, about 0.75%, or about 1% by weight based on the total weight of the pharmaceutical composition.

In certain embodiments, the pharmaceutical composition comprises starch in the extragranular excipients in an amount of from about 0.1% to about 2%; from about 0.1% to about 1%, from about 0.25% to about 1.5%; or from about 0.5% to about 1.0% by weight based on the total weight of the pharmaceutical composition. In one embodiment, the pharmaceutical composition comprises starch in the extragranular excipients in an amount of about 0.5%, about 0.75%, or about 1% by weight based on the total weight of the pharmaceutical composition.

In certain embodiments, the pharmaceutical composition comprises talc in the extragranular excipients in an amount of from about 0.1% to about 2%; from about 0.1% to about 1%, from about 0.25% to about 1.5%; or from about 0.5% to about 1.0% by weight based on the total weight of the pharmaceutical composition. In one embodiment, the pharmaceutical composition comprises talc in the extragranular excipients in an amount of about 0.5%, about 0.75%, or about 1% by weight based on the total weight of the pharmaceutical composition.

In certain embodiments, the lubricating agent used in the extragranular excipients is sodium stearyl fumarate, magnesium stearate, talc, silica, stearic acid, and glyceryl behenate. In one embodiment, the lubricant is sodium stearyl fumarate. In one embodiment, the lubricant is magnesium stearate. In one embodiment, the lubricant is talc. In one embodiment, the lubricant is silica. In one embodiment, the lubricant is stearic acid. In one embodiment, the lubricant is glyceryl behenate.

In certain embodiments, the lubricating agent is present in the extragranular excipients in an amount from about 0.25% to about 1.5% by weight based on the total weight of the pharmaceutical composition. In certain embodiments, the amount of the lubricating agent in the extragranular excipients is about 0.5%, about 0.75%, about 1%, about 1.25%, or about 1.5% by weight based on the total weight of the pharmaceutical composition.

In certain embodiments, the pharmaceutical composition comprises sodium stearyl fumarate in the extragranular excipients in an amount of from about 0.25% to about 1.5% by weight based on the total weight of the pharmaceutical composition. In certain embodiments, the pharmaceutical composition comprises sodium stearyl fumarate in the intragranular excipients in an amount of about 0.5%, about 0.75%, about 1%, about 1.25%, or about 1.5% by weight based on the total weight of the pharmaceutical composition.

In certain embodiments, the pharmaceutical composition comprises magnesium stearate in the extragranular excipients in an amount of from about 0.25% to about 1.5% by weight based on the total weight of the pharmaceutical composition. In certain embodiments, the pharmaceutical composition comprises magnesium stearate in the extragranular excipients in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises talc in the extragranular excipients in an amount of from about 0.25% to about 1.5% by weight based on the total weight of the pharmaceutical composition. In certain embodiments, the pharmaceutical composition comprises talc in the extragranular excipients in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises silica in the extragranular excipients in an amount of from about 0.25% to about 1.5% by weight based on the total weight of the pharmaceutical composition. In certain embodiments, the pharmaceutical composition comprises silica in the extragranular excipients in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises stearic acid in the extragranular excipients in an amount of from about 0.25% to about 1.5% by weight based on the total weight of the pharmaceutical composition. In certain embodiments, the pharmaceutical composition comprises stearic acid in the extragranular excipients in an amount of about 0.5%, about 0.75%, about 1%, about 1.25%, about 1.5%, about 1.75%, or about 2% by weight based on the total weight of the pharmaceutical composition.

In certain embodiments, the pharmaceutical composition comprises glyceryl behenate in the extragranular excipients in an amount of from about 0.25% to about 1.5% by weight based on the total weight of the pharmaceutical composition. In certain embodiments, the pharmaceutical composition comprises glyceryl behenate in the extragranular excipients in an amount of about 0.5%, about 0.75%, about 1%, about 1.25%, about 1.5%, about 1.75%, or about 2% by weight based on the total weight of the pharmaceutical composition.

The pharmaceutical compositions provided herein may contain various extragranular excipients other than the above-mentioned excipients, which are pharmaceutically acceptable and used as excipients. Examples of the other excipients include, but are not limited to, diluents, disintegrants, coloring agents, coating agents, and flavoring agents.

3. Pharmaceutical Compositions

In certain embodiments, Compound 1 or a pharmaceutically acceptable salt thereof makes up from between about 10% w/w to about 20% w/w of the pharmaceutical composition, the diluent(s) makes up from between about 76.5% w/w to about 83% w/w of the pharmaceutical composition, the disintegrant makes up from between about 3% w/w to about 5% w/w of the pharmaceutical composition, and the lubricant makes up from between about 0.5% w/w to about 2.0% w/w of the pharmaceutical composition, thereby totaling 100% by weight of the composition. In some embodiments, the pharmaceutically acceptable salt of Compound 1 is the Tris salt.

In some embodiments, Compound 1 or a pharmaceutically acceptable salt thereof makes up from between about 48% w/w to about 60% w/w of the pharmaceutical composition, the diluent(s) makes up from between about 37.5% w/w to about 44% w/w of the pharmaceutical composition, the disintegrant makes up from between about 2% w/w to about 6% w/w of the pharmaceutical composition, and the lubricant makes up from between about 0.5% w/w to about 2.0% w/w of the pharmaceutical composition, thereby totaling 100% by weight of the composition. In some embodiments, the pharmaceutically acceptable salt of Compound 1 is the Tris salt.

In some embodiments, Compound 1 or a pharmaceutically acceptable salt thereof makes up from between about 36% w/w to about 54% w/w of the pharmaceutical composition, the diluent(s) makes up from between about 40.5% w/w to about 45% w/w of the pharmaceutical composition, the disintegrant makes up from between about 2% w/w to about 4% w/w of the pharmaceutical composition, the binder makes up from between about 2% w/w to about 8% w/w of the pharmaceutical composition, the surfactant makes up from between about 0.5% w/w to about 3% w/w of the pharmaceutical composition, the glidant makes up from between about 0.5% w/w to about 2.0% w/w of the pharmaceutical composition, and the lubricant makes up from between about 0.5% w/w to about 2.0% w/w of the pharmaceutical composition, thereby totaling 100% by weight of the composition. In some embodiments, the pharmaceutically acceptable salt of Compound 1 is the Tris salt.

In some embodiments, Compound 1 or a pharmaceutically acceptable salt thereof makes up from between about 42% w/w to about 63% w/w of the pharmaceutical composition, the diluent(s) makes up from between about 32.5% w/w to about 38% w/w of the pharmaceutical composition, the disintegrant makes up from between about 2% w/w to about 4% w/w of the pharmaceutical composition, the binder makes up from between about 2% w/w to about 8% w/w of the pharmaceutical composition, the surfactant makes up from between about 0% w/w to about 2% w/w of the pharmaceutical composition, the glidant makes up from between about 0% w/w to about 3% w/w of the pharmaceutical composition, and the lubricant makes up from between about 0.5% w/w to about 3.0% w/w of the pharmaceutical composition, thereby totaling 100% by weight of the composition. In some embodiments, the pharmaceutically acceptable salt of Compound 1 is the Tris salt.

In some embodiments, Compound 1 or a pharmaceutically acceptable salt thereof makes up from between about 47% w/w to about 70% w/w of the pharmaceutical composition, the diluent(s) makes up from between about 26.5% w/w to about 32% w/w of the pharmaceutical composition, the disintegrant makes up from between about 2% w/w to about 4% w/w of the pharmaceutical composition, the binder makes up from between about 1% w/w to about 9% w/w of the pharmaceutical composition, the surfactant makes up from between about 0% w/w to about 2% w/w of the pharmaceutical composition, the glidant makes up from between about 0% w/w to about 3% w/w of the pharmaceutical composition, the lubricant makes up from between about 0.5% w/w to about 3.0% w/w of the pharmaceutical composition, thereby totaling 100% by weight of the composition. In some embodiments, the pharmaceutically acceptable salt of Compound 1 is the Tris salt.

In certain embodiments, the pharmaceutical composition comprises an intragranular portion and an extragranular portion. In some embodiments, the intragranular portion of the pharmaceutical composition of the application comprises Compound 1 or a pharmaceutically acceptable salt thereof, a diluent, a disintegrant, a binder, a surfactant, a glidant, and a lubricant. In some embodiments, the extragranular portion of the pharmaceutical composition of the application comprises an additional amount of the glidant and lubricant.

In some embodiments, the intragranular portion of the pharmaceutical composition of the application comprises Compound 1 or a pharmaceutically acceptable salt thereof, a diluent, a disintegrant, a binder, and a lubricant. In some embodiments, the extragranular portion of the pharmaceutical composition of the application comprises an additional amount of the lubricant.

In some embodiments, the intragranular portion of the pharmaceutical composition of the application comprises Compound 1 or a pharmaceutically acceptable salt thereof, a diluent, a disintegrant, and a lubricant. In some embodiments, there is no extragranular portion of the pharmaceutical composition.

In some embodiments, the intragranular portion of the pharmaceutical composition of the application comprises: Compound 1 or the Tris salt of Compound 1 in an amount of from about 37% w/w to about 50% w/w of the pharmaceutical composition, a diluent (or one or more diluents) in an amount of from about 41% w/w to about 45% w/w of the pharmaceutical composition, a disintegrant in an amount of from about 2% w/w to about 4% w/w of the pharmaceutical composition, a binder in an amount of from between about 2% w/w to about 8% w/w of the pharmaceutical composition, a surfactant in an amount of from between about 0.5% w/w to about 3% w/w of the pharmaceutical composition, a glidant in an amount of from between about 0.5% w/w to about 1.5% w/w of the pharmaceutical composition, and a lubricant in an amount of from between about 0.5% w/w to about 1.5% w/w of the pharmaceutical composition.

In some embodiments, the intragranular portion of the pharmaceutical composition comprises: Compound 1 or the Tris salt of Compound 1 in an amount of from between about 42% w/w to about 63% w/w of the pharmaceutical composition, a diluent (or one or more diluents) in an amount of from between about 32% w/w to about 38% w/w of the pharmaceutical composition, a disintegrant in an amount of from between about 2% w/w to about 4% w/w of the pharmaceutical composition, a binder in an amount of from between about 2% w/w to about 8% w/w of the pharmaceutical composition, a surfactant in an amount of from between about 0% w/w to about 2% w/w of the pharmaceutical composition, a glidant in an amount of from between about 0% w/w to about 1.5% w/w of the pharmaceutical composition, and a lubricant in an amount of from between about 0.5% w/w to about 1.5% w/w of the pharmaceutical composition.

In some embodiments, the intragranular portion of the pharmaceutical composition comprises: Compound 1 or the Tris salt of Compound 1 in an amount from between about 51% w/w to about 68% w/w of the pharmaceutical composition, a diluent (or one or more diluents) in an amount of from between about 26% w/w to about 32% w/w of the pharmaceutical composition, a disintegrant in an amount of from between about 2% w/w to about 4% w/w of the pharmaceutical composition, a binder in an amount of from between about 1% w/w to about 9% w/w of the pharmaceutical composition, a surfactant in an amount of from between about 0% w/w to about 2% w/w of the pharmaceutical composition, a glidant in an amount of from between about 0% w/w to about 1.5% w/w of the pharmaceutical composition, a lubricant in an amount of from between about 0.5% w/w to about 2.0% w/w of the pharmaceutical composition.

In some embodiments, the extragranular portion of the pharmaceutical composition comprises: an additional amount of the glidant in an amount of from about 0.5% w/w to about 1% w/w of the pharmaceutical composition, and an additional amount of the lubricant in an amount of from about 0.5% w/w to about 1.5% w/w of the pharmaceutical composition. In some embodiments, the extragranular portion of the pharmaceutical composition comprises an additional amount of the lubricant in an amount of from about 0.5% w/w to about 1.5% w/w of the pharmaceutical composition 4. Solid Dispersions Pharmaceutical compositions comprising solid dispersions of a therapeutically active compound in a matrix can provide improved chemical and physical properties and can be prepared by forming a homogeneous solution or melt of the therapeutically active compound and matrix material followed by solidifying the mixture by cooling, or removal of the solvent. Such solid dispersions of therapeutically active compounds often show enhanced bioavailability when administered orally relative to oral compositions comprising the undispersed compound.

As used herein, the term "dispersion" refers to a disperse system in which one substance (the dispersed phase) is distributed, in discrete units, throughout a second substance (the continuous phase or vehicle). In general, the dispersed phases can be solids, liquids, or gases. In the case of a solid dispersion, the dispersed and continuous phases are both solids.

As used herein, the term "amorphous solid dispersion" generally refers to a solid dispersion of two or more components, usually a therapeutically active compound and a polymer (or plurality of polymers), but possibly containing other components such as surfactants or other pharmaceutical excipients, where the therapeutically active compound is in the amorphous phase. In some embodiments, an amorphous solid dispersion includes the polymer(s) (and optionally a surfactant) constituting the dispersed phase, and the therapeutically active compound constitutes the continuous phase. In some embodiments, an amorphous solid dispersion includes the polymer(s) (and optionally a surfactant) constituting the continuous phase, and the therapeutically active compound constitutes the dispersed phase. In some embodiments, the therapeutically active compound is substantially amorphous. In other embodiments, the therapeutically active compound is substantially crystalline.

In some embodiments, the solid dispersion comprises Compound 1, or a pharmaceutically acceptable salt of Compound 1, or the Tris salt of Compound 1, or the sodium salt of Compound 1, and one or more polymer(s). In some embodiments, the solid dispersion comprises Compound 1, or a pharmaceutically acceptable salt of Compound 1, or the Tris salt of Compound 1, or the sodium salt of Compound 1, one or more polymer(s), and one or more surfactant(s). In some embodiments, the solid dispersion comprises Compound 1, or a pharmaceutically acceptable salt of Compound 1, or the Tris salt of Compound 1, or the sodium salt of Compound 1, and one polymer. In some embodiments, the solid dispersion comprises Compound 1, or a pharmaceutically acceptable salt of Compound 1, or the Tris salt of Compound 1, or the sodium salt of Compound 1, one polymer, and a surfactant. In certain embodiments, the free form of Compound 1 is used in the solid dispersion. In other embodiments, a pharmaceutically acceptable salt of Compound 1 is used in the solid dispersion. In certain embodiments, the pharmaceutically acceptable salt of Compound 1 used in the solid dispersion is the Tris salt of Compound 1. In other embodiments, the pharmaceutically acceptable salt of Compound 1 used in the solid dispersion is the sodium salt of Compound 1.

In some embodiments, the polymer is selected from hydroxypropyl methyl cellulose (HPMC), hydroxypropyl methylcellulose acetate succinate (HPMCAS), hydroxypropyl methyl cellulose phthalate (HPMCP), hydroxypropyl cellulose (HPC), ethylcellulose, cellulose acetate phthalate, and polyvinylpyrrolidone (PVP), and mixtures thereof. In some embodiments the polymer is a cellulose based polymer such as HPMC, HPMCAS, HPC, and ethylcellulose. In other embodiments, the polymer is HPMCAS.

In some embodiments, the polymer is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer is (or the one or more polymers are) present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer is (or the one or more polymers are) present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, Compound 1, or a pharmaceutically acceptable salt of Compound 1, or the Tris salt of Compound 1, or the sodium salt of Compound 1 is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, Compound 1, or a pharmaceutically acceptable salt of Compound 1, or the Tris salt of Compound 1, or the sodium salt of Compound 1 is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, about 54% w/w, or about 60% w/w. In some embodiments, Compound 1, or a pharmaceutically acceptable salt of Compound 1, or the Tris salt of Compound 1, or the sodium salt of Compound 1 is present in the amorphous solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the solid dispersion further comprises a surfactant. In some embodiments, the surfactant is selected from sodium lauryl sulfate (SLS), vitamin E or a derivative thereof (e.g., vitamin E TPGS), docusate sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In other embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

In some embodiments, the solid dispersion comprises Compound 1, or a pharmaceutically acceptable salt of Compound 1, or the Tris salt of Compound 1, or the sodium salt of Compound 1 and HPMCAS. In some embodiments, the solid dispersion consists essentially of Compound 1, or a pharmaceutically acceptable salt of Compound 1, or the Tris salt of Compound 1, or the sodium salt of Compound 1 and HPMCAS. In some embodiments, the solid dispersion consists of Compound 1, or a pharmaceutically acceptable salt of Compound 1, or the Tris salt of Compound 1, or the sodium salt of Compound 1 and HPMCAS. In some embodiments, Compound 1, or a pharmaceutically acceptable salt of Compound 1, or the Tris salt of Compound 1, or the sodium salt of Compound 1 and HPMCAS are present in a weight ratio of between about 3:1 and about 1:3, or between about 2:1 and about 1:2, or between about 1.5:1 and about 1:1.5. In some embodiments, Compound 1, or a pharmaceutically acceptable salt of Compound 1, or the Tris salt of Compound 1, or the sodium salt of Compound land HPMCAS are present in a weight ratio of about 1:1.

In another aspect, the disclosure relates to a method of preparing a solid dispersion of Compound 1, or a pharmaceutically acceptable salt of Compound 1, or the Tris salt of Compound 1, or the sodium salt of Compound 1.

In some embodiments, the method comprises spray-drying a mixture comprising Compound 1, or a pharmaceutically acceptable salt of Compound 1, or the Tris salt of Compound 1, or the sodium salt of Compound 1, a polymer, and an appropriate solvent or solvent mixture.

In some embodiments, the solvent is a volatile solvent (e.g., methylene chloride, acetone, methanol, ethanol, chloroform, tetrahydrofuran (THF), or a mixture thereof). In some embodiments, the solvent is acetone.

In some embodiments, Compound 1, or a pharmaceutically acceptable salt of Compound 1, or the Tris salt of Compound 1, or the sodium salt of Compound 1 may be used as the starting material in a spray-drying process to prepare the solid dispersion. In some embodiments, one of the crystalline forms described herein may be used as the starting material in the spray-drying process.

Spray drying involves atomization of a liquid solution containing, e.g., a solid and a solvent or solvent mixture, and removal of the solvent or solvent mixture. Atomization may be done, for example, through a two-fluid or pressure or electrosonic nozzle or on a rotating disk. Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.). Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954).

5. Exemplary Capsule Formulations

Formulations for oral use may also be presented as hard gelatin or hydroxypropylmethylcellulose (HPMC) capsules wherein the active ingredient is mixed with an inert solid diluent, such as for example, calcium carbonate, calcium phosphate or kaolin and mixtures thereof, or as soft gelatin capsules wherein the active ingredient is mixed with water or an oil medium, for example peanut oil, liquid paraffin or olive oil.

In some embodiments, the capsule composition provided herein comprises about 10% w/w to about 20% w/w of the Tris salt of Compound 1 based on the total weight of the capsule and excipients comprising a diluent (or one or more diluents) in an amount of from about 76.5% w/w to about 83% w/w of the capsule, a disintegrant in an amount of from about 3% w/w to about 5% w/w of the capsule, and a lubricant in an amount of from about 0.5% w/w to about 2.0% w/w of the capsule, all based on the total weight of the capsule. In one embodiment, the Tris salt comprises Tris salt Form C.

In some embodiments, the capsule composition provided herein comprises about 48% w/w to about 60% w/w of the Tris salt of Compound 1 based on the total weight of the capsule, and excipients comprising a diluent (or one or more diluents) in an amount of from about 37.5% w/w to about 44% w/w of the capsule, a disintegrant in an amount of from about 2% w/w to about 6% w/w of the capsule, and a lubricant in an amount of from about 0.5% w/w to about 2.0% w/w of the capsule. In one embodiment, the Tris salt comprises Tris salt Form C.

In some embodiments, the capsule composition provided herein comprises about 37% w/w to about 50% w/w of the Tris salt of Compound 1 based on the total weight of the capsule; intragranular excipients comprising about 41% w/w to about 45% w/w of a diluent(s), about 2% w/w to about 4% w/w of a disintegrant, about 2% w/w to about 8% w/w of a binder, about 0.5% w/w to about 3% w/w of a surfactant, about 0.5% w/w to about 2.0% w/w of a glidant, and about 0.5% w/w to about 2.0% w/w of a lubricant; and extra-granular excipients comprising about 0.5% w/w to about 2.0% w/w of a glidant, and about 0.5% w/w to about 2.0% w/w of a lubricant, all based on the total weight of the capsule. In one embodiment, the Tris salt comprises Tris salt Form C.

In some embodiments, the capsule composition provided herein comprises about 42% w/w to about 63% w/w of the Tris salt of Compound 1 based on the total weight of the capsule; intragranular excipients comprising about 32% w/w to about 38% w/w of a diluent(s), about 2% w/w to about 4% w/w of a disintegrant, about 2% w/w to about 8% w/w of a binder, about 0% w/w to about 2% w/w of a surfactant, about 0% w/w to about 3.0% w/w of a glidant, and about 0.5% w/w to about 3.0% w/w of a lubricant; and extra-granular excipients comprising about 0% w/w to about 2.0% w/w of a glidant, and about 0.5% w/w to about 2.0% w/w of a lubricant, all based on the total weight of the capsule. In one embodiment, the Tris salt comprises Tris salt Form C.

In some embodiments, the capsule composition provided herein comprises about 51% w/w to about 68% w/w of the Tris salt of Compound 1 based on the total weight of the capsule; intragranular excipients comprising about 26% w/w to about 32% w/w of a diluent(s), about 2% w/w to about 4% w/w of a disintegrant, about 1% w/w to about 9% w/w of a binder, about 0% w/w to about 2% w/w of a surfactant, about 0% w/w to about 3.0% w/w of a glidant, about 0.5% w/w to about 3.0% w/w of a lubricant; and extra-granular excipients comprising about 0% w/w to about 2.0% w/w of a glidant, and about 0.5% w/w to about 2.0% w/w of a lubricant, all based on the total weight of the capsule. In one embodiment, the Tris salt comprises Tris salt Form C.

6. Exemplary Tablet Formulations

For tablet compositions, Compound 1 or a pharmaceutically acceptable salt thereof in admixture with one or more pharmaceutically acceptable excipients that are used for the manufacture of tablets may be used. Examples of such excipients include without limitation diluents, such as calcium carbonate, sodium carbonate, lactose, calcium phosphate, sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

In certain embodiments, the tablet is a coated tablet. In certain embodiments, the coating is a film coating. In certain embodiments, the coating agent is Opadry II. In certain embodiments, the coating agent comprises polyvinyl alcohol.

Any conventional method for obtaining a tablet can be used, for example, the methods described in pharmacopoeias such as the U.S. Pharmacopeia, and the European Pharmacopoeia, may be used.

In some embodiments, the tablet composition provided herein comprises about 10% w/w to about 20% w/w of the Tris salt of Compound 1 based on the total weight of the tablet and excipients comprising a diluent (or one or more diluents) in an amount of from about 76.5% w/w to about 83% w/w of the tablet, a disintegrant in an amount of from about 3% w/w to about 5% w/w of the tablet, and a lubricant in an amount of from about 0.5% w/w to about 2.0% w/w of the tablet, all based on the total weight of the tablet. In one embodiment, the Tris salt comprises Tris salt Form C.

In some embodiments, the tablet composition provided herein comprises about 48% w/w to about 60% w/w of the Tris salt of Compound 1 based on the total weight of the tablet, and excipients comprising a diluent (or one or more diluents) in an amount of from about 37.5% w/w to about 44% w/w of the tablet, a disintegrant in an amount of from about 2% w/w to about 6% w/w of the tablet, and a lubricant in an amount of from about 0.5% w/w to about 2.0% w/w of the tablet. In one embodiment, the Tris salt comprises Tris salt Form C.

In some embodiments, the tablet composition provided herein comprises about 37% w/w to about 50% w/w of the Tris salt of Compound 1 based on the total weight of the tablet; intragranular excipients comprising about 41% w/w to about 45% w/w of a diluent(s), about 2% w/w to about 4% w/w of a disintegrant, about 2% w/w to about 8% w/w of a binder, about 0.5% w/w to about 3% w/w of a surfactant, about 0.5% w/w to about 2.0% w/w of a glidant, and about 0.5% w/w to about 2.0% w/w of a lubricant; and extra-granular excipients comprising about 0.5% w/w to about 2.0% w/w of a glidant, and about 0.5% w/w to about 2.0% w/w of a lubricant, all based on the total weight of the tablet. In one embodiment, the Tris salt comprises Tris salt Form C.

In some embodiments, the tablet composition provided herein comprises about 42% w/w to about 63% w/w of the Tris salt of Compound 1 based on the total weight of the tablet; intragranular excipients comprising about 32% w/w to about 38% w/w of a diluent(s), about 2% w/w to about 4% w/w of a disintegrant, about 2% w/w to about 8% w/w of a binder, about 0% w/w to about 2% w/w of a surfactant, about 0% w/w to about 3.0% w/w of a glidant, and about 0.5% w/w to about 3.0% w/w of a lubricant; and extra-granular excipients comprising about 0% w/w to about 2.0% w/w of a glidant, and about 0.5% w/w to about 2.0% w/w of a lubricant, all based on the total weight of the tablet. In one embodiment, the Tris salt comprises Tris salt Form C.

In some embodiments, the tablet composition provided herein comprises about 51% w/w to about 68% w/w of the Tris salt of Compound 1 based on the total weight of the tablet; intragranular excipients comprising about 26% w/w to about 32% w/w of a diluent(s), about 2% w/w to about 4% w/w of a disintegrant, about 1% w/w to about 9% w/w of a binder, about 0% w/w to about 2% w/w of a surfactant, about 0% w/w to about 3.0% w/w of a glidant, about 0.5% w/w to about 3.0% w/w of a lubricant; and extra-granular excipients comprising about 0% w/w to about 2.0% w/w of a glidant, and about 0.5% w/w to about 2.0% w/w of a lubricant, all based on the total weight of the tablet. In one embodiment, the Tris salt comprises Tris salt Form C.

7. Other Formulations

For aqueous suspensions, a compound of the present disclosure is admixed with excipients suitable for maintaining a stable suspension. Examples of such excipients include without limitation sodium carboxymethylcellulose, methylcellulose, hydroxypropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water may be formulated by providing a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin and mixtures thereof. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensaturatedion products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to techniques known in the art using one of more suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compound 1 or a pharmaceutically acceptable salt thereof may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter, beeswax, and polyethylene glycols.

Compositions for parenteral administrations are administered in a sterile medium. Depending on the vehicle used and the concentration of the drug in the formulation, the parenteral formulation can either be a suspension or a solution containing dissolved drug. Adjuvants such as local anesthetics, preservatives and buffering agents can also be added to parenteral compositions.

Another embodiment of the invention is a liquid formulation comprising the sodium salt of Compound 1 that is suitable for administration orally or parenterally. Typically, the liquid formulation is aqueous. For oral administration, certain sweetening and/or flavoring and/or coloring agents may be added.

The amount of active ingredient that may be combined with one or more pharmaceutical excipients to produce a single dosage form will vary depending upon the patient treated and the particular mode of administration. In certain embodiments, the pharmaceutical composition comprises between about 10 mg to about 1500 mg of Compound 1 or a pharmaceutically acceptable salt thereof (based on the weight of the free form of Compound 1, apart from the weight of any conformer, salt former, water of hydration, solvent of solvation and the like.) In some embodiments, the pharmaceutical composition comprises between about 90 mg and about 240 mg; between about 100 mg and about 240 mg; between about 10 mg and about 500 mg; or between about 10 mg and about 1000 mg of Compound 1 or a pharmaceutically acceptable salt. In some embodiments, the pharmaceutical composition comprises about 10 mg, about 25 mg, about 50 mg, about 75 mg, about 90 mg, about 100 mg, about 110 mg, about 120 mg, about 125 mg, about 130 mg, about 140 mg, about 150 mg, about 160 mg, about 170 mg, about 175 mg, about 180 mg, about 190 mg, about 200 mg, about 210 mg, about 220 mg, about 225 mg, about 230 mg, about 240 mg, about 250 mg, about 260 mg, about 270 mg, about 275 mg, about 280 mg, about 290 mg, or about 300 mg of Compound 1 or a pharmaceutically acceptable salt thereof. In some embodiments, the pharmaceutical composition comprises about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, or about 1450 mg, or about 1500 mg. In certain embodiments, the pharmaceutical composition is in the form of an orally acceptable dosage form, such as for example a capsule, and comprises about 50 mg, about 75 mg, about 90 mg, about 100 mg, about 110 mg, about 120 mg, about 125 mg, about 130 mg, about 140 mg, about 150 mg, about 160 mg, about 170 mg, about 175 mg, about 180 mg, about 190 mg, about 200 mg, about 210 mg, about 220 mg, about 225 mg, about 230 mg, about 240 mg, about 250 mg, about 260 mg, about 270 mg, about 275 mg, about 280 mg, about 290 mg, or about 300 mg of the Tris salt of Compound 1.

Methods of Treatment, Uses for Manufacture of Medicament, Salts or Crystalline Forms for Use in Disease Treatment In one aspect, the crystalline and amorphous forms described herein and pharmaceutical compositions thereof are inhibitors of DHODH (but not so limited), and are generally useful for treating the underlying condition of DHODH. The tris(hydroxymethyl)aminomethane salt of Compound 1 described in the following paragraphs includes any of the Tris salt in accordance with the first through twenty-fifth embodiments described above. The crystalline form of Compound 1 described in the following paragraphs includes any of the crystalline form in accordance with any one of the twenty-seventh through fifty-ninth embodiments described above.

In one aspect, the present disclosure relates to a method of treating cancer in a subject, comprising administering to the subject an effective amount of the tris(hydroxymethyl) aminomethane salt of Compound 1, the sodium salt of Compound 1, the crystalline form of Compound 1, or the pharmaceutical composition thereof. In another aspect, the present disclosure relates to use of the tris(hydroxymethyl) aminomethane salt of Compound 1, the sodium salt of Compound 1, the crystalline form of Compound 1, or the pharmaceutical composition thereof for the manufacture of a medicament for treating cancer. In yet another aspect, the present disclosure relates to the tris(hydroxymethyl)aminomethane salt of Compound 1, the sodium salt of Compound 1, the crystalline form of Compound 1, or the pharmaceutical composition thereof for treating cancer.

In some embodiments, the cancer comprises a solid tumor. In some embodiments, the cancer is selected from lung cancer, breast cancer, triple negative breast cancer, melanoma, glioblastoma, prostate cancer, colon cancer, pancreatic cancer, bone cancer, cancer of the head or neck, skin cancer, cutaneous or intraocular malignant endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, an environmentally induced cancer, and a PTEN mutant cancer. In some embodiments, the cancer is selected from biliary tract cancer or cancer of the ampulla of Vater, non-small cell lung cancer, bronchoalveolar carcinoma, liver cancer, cancer of the ovary, and cancer of the upper aerodigestive tract. In another embodiment, the cancer is a hematological cancer. In one embodiment, the hematological cancer is selected from myeloma, lymphoma, and leukemia. In one embodiment, the hematological cancer is selected from acute myeloid leukemia, multiple myeloma, B-prolymphocytic leukemia, acute lymphoblastic leukemia, chronic lymphocytic leukemia, Hodgkin's disease, non-Hodgkin's lymphoma, follicular lymphoma, diffuse large B cell lymphoma, anaplastic large cell lymphoma, mantle cell lymphoma, lymphocytic lymphoma cancer of the bladder, primary CNS lymphoma, and T-cell lymphoma; In one embodiment, the hematological cancer is selected from chemotherapy-resistant acute myeloid leukemia, cytarabine-resistant acute myeloid leukemia, acute monocytic leukemia, acute lymphoblastic leukemia, B-cell lymphoma, diffuse mixed cell lymphoma, myelodysplastic syndrome, myelodysplastic/myeloproliferative neoplasms, primary effusion lymphoma, erythroleukemia, chronic myeloid leukemia, chronic monocytic leukemia, double hit diffuse large B cell lymphoma, and triple hit diffuse large B cell lymphoma. In one embodiment, the hematological cancer is selected from angioimmunoblastic lymphoma, Burkitt's lymphoma, Burkitt-like lymphoma, blastic NK-cell lymphoma, cutaneous T-cell lymphoma, lymphoblastic lymphoma, MALT lymphoma, mediastinal large B-cell lymphoma, nodal marginal zone B-cell lymphoma, small lymphocytic lymphoma, thyroid lymphoma, follicular lymphoma, Waldenstrom's macroglobulinemia, essential thrombocythemia, chronic idiopathic myelofibrosis, and polyeythemia rubra vera.

In a further aspect, the present disclosure relates to a method of treating cancer in a subject, wherein the cancer is responsive to inhibition of dihydroorotate dehydrogenase, comprising administering to the subject an effective amount of the tris(hydroxymethyl)aminomethane salt of Compound 1 (or one of the disclosed crystal forms thereof), the sodium salt of Compound 1, the crystalline form of Compound 1, or the pharmaceutical composition thereof. In another aspect, the present relates to use of the tris(hydroxymethyl)aminomethane salt of Compound 1, the sodium salt of Compound 1, the crystalline form of Compound 1, or the pharmaceutical composition thereof for the manufacture of a medicament for treating cancer, wherein the cancer is responsive to inhibition of dihydroorotate dehydrogenase. In yet another aspect, the present disclosure relates to the tris(hydroxymethyl)aminomethane salt of Compound 1, the sodium salt of Compound 1, the crystalline form of Compound 1, or the pharmaceutical composition thereof for treating cancer, wherein the cancer is responsive to inhibition of dihydroorotate dehydrogenase. In one embodiment, the cancer may be selected from the list of cancers described above.

In a further aspect, the present disclosure relates to a method of treating a condition or a disease selected from a viral-mediated disease, transplant rejection, rheumatoid arthritis, psoriasis, an autoimmune disease, or an inflammatory disorder in a subject, comprising administering to the subject an effective amount of the tris(hydroxymethyl)aminomethane salt of Compound 1 (or one of the disclosed crystal forms thereof), the sodium salt of Compound 1, the crystalline form of Compound 1, or the pharmaceutical composition thereof. In another aspect, the present relates to use of the tris(hydroxymethyl)aminomethane salt of Compound 1, the sodium salt of Compound 1, the crystalline form of Compound 1, or the pharmaceutical composition thereof for the manufacture of a medicament for treating a condition or a disease selected from a viral-mediated disease, transplant rejection, rheumatoid arthritis, psoriasis, an autoimmune disease, or an inflammatory disorder. In yet another aspect, the present disclosure relates to the tris(hydroxymethyl)aminomethane salt of Compound 1, the sodium salt of Compound 1, the crystalline form of Compound 1, or the pharmaceutical composition thereof for treating a condition or a disease selected from a viral-mediated disease, transplant rejection, rheumatoid arthritis, psoriasis, an autoimmune disease, or an inflammatory disorder.

In another aspect, the present disclosure relates to a method of inhibiting growth and/or metastasis of tumor cells in a subject wherein the tumor cells are responsive to inhibition of dihydroorotate dehydrogenase, comprising administering to the subject an effective amount of the tris(hydroxymethyl)aminomethane salt of Compound 1 (or one of the disclosed crystal forms thereof), the sodium salt of Compound 1, the crystalline form of Compound 1, or the pharmaceutical composition thereof.

In another aspect, the present disclosure relates to a method of inhibiting dihydroorotate dehydrogenase in a subject wherein the tumor cells are responsive to inhibition of dihydroorotate dehydrogenase, comprising administering to the subject an effective amount of the tris(hydroxymethyl)aminomethane salt of Compound 1 (or one of the disclosed crystal forms thereof), the sodium salt of Compound 1, the crystalline form of Compound 1, or the pharmaceutical composition thereof.

Another embodiment of the invention is a method of treating a subject with cancer with Compound 1 or a pharmaceutically acceptable salt thereof. Compound 1 or a pharmaceutically acceptable salt thereof is preferably provided as i) the Tris salt (e.g., in amorphous form or in one of the disclosed crystalline forms); ii) the sodium salt of Compound 1; iii) one the disclosed crystalline forms of Compound 1; or iv) the amorphous form of Compound 1. The cancer being treated is a haematological cancer is selected from myeloma, lymphoma, leukaemia, such as acute myeloid leukaemia (AML), chronic myeloproliferative disease, monoclonal gammopathy of uncertain significance, myelodysplastic syndrome, amyloidosis, and myelodysplastic/myeloproliferative neoplasms; the myeloma being treated is selected from multiple myeloma, amyloidosis, plasmacytoma, monoclonal gammopathy of undetermined significance, asymptomatic myeloma, symptomatic myeloma and Kahler's disease; the lymphoma being treated is selected from anaplastic large cell lymphoma, Burkitt lymphoma, Burkitt-like lymphoma, cutaneous T-cell lymphoma, diffuse large B-cell lymphoma, diffuse large B-cell lymphoma, lymphoblastic lymphoma, MALT lymphoma, mantle cell lymphoma, mediastinal large B-cell lymphoma, nodal marginal zone B-cell lymphoma, small lymphocytic lymphoma, thyroid lymphoma, and Waldenstrom's macroglobulinaemia; the chronic myeloproliferative disease being treated is selected from essential thrombocythaemia, chronic idiopathic myelofibrosis, and polycythaemia rubra vera; and the leukaemia being treated is selected from acute myeloid leukaemia (AML), hairy cell leukaemia, acute lymphoblastic leukaemia, and chronic lymphoblastic leukaemia.

In yet another aspect, the present disclosure relates to a method of treating cancer in a subject, comprising administering to the subject an effective amount of Compound 1 or a pharmaceutically acceptable salt thereof. In one embodiment, the Compound 1 or a pharmaceutically acceptable salt thereof is a tris(hydroxymethyl)aminomethane (Tris) salt of Compound 1 as described herein (including all partially crystalline or crystalline Tris salt forms of Compound 1 disclosed herein), sodium salt of Compound 1 as described herein, or the free acid Compound 1 (including all partially crystalline or crystalline forms of the free acid Compound 1 disclosed herein), wherein one of the dosing regimens described in the following paragraphs is implemented. In one embodiment, the subject is treated by administering an effective amount of a crystalline Tris salt of Compound 1 to the subject. In one particular embodiment, the crystalline Tris salt is crystalline Tris salt Form C as described herein. In another embodiment, the subject is treated by administering an effective amount of a crystalline form of the free acid Compound 1 to the subject.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) once a week in one or more 28-day or 4-week cycles.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for a period of 2 to 5 days each week, with 1 cycle of therapy defined as 4 consecutive weeks of treatment.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for a period of 2 to 4 consecutive days followed by a 3 to 5 day break each week, in one or more 28-day or 4-week cycle.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for 2 consecutive days followed by a 5-day break each week, in one or more 28-day or 4-week cycles.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for 3 consecutive days followed by a 4-day break each week, in one or more 28-day or 4-week cycles.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for 4 consecutive days followed by a 3-day break each week, in one or more 28-day or 4-week cycles.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for a period of 2 to 4 consecutive days followed by a 3 to 5 day break each week, in one or more 28-day or 4-week cycle, where the number of consecutive days of treatment is increased in at least one of the weeks of the 28-day or 4-week cycle. In another embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) for a period of 2 to 4 consecutive days followed by a 3 to 5 day break each week, in one or more 28-day or 4-week cycle, where the number of consecutive days of treatment is decreased in at least one of the weeks of the 28-day or 4-week cycle.

In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 2 consecutive days followed by a 5-day break for the first week of a 28-day or 4-week cycle, where the number of consecutive days of treatment is increased in at least one of the weeks of the 28-day or 4-week cycle. In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 2 consecutive days followed by a 5-day break for the first week of a 28-day or 4-week cycle, where the number of consecutive days of treatment is decreased in at least one of the weeks of a 28-day or 4-week cycle.

In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 3 consecutive days followed by a 4-day break for the first week of a 28-day or 4-week cycle, where the number of consecutive days of treatment is increased in at least one of the weeks of a 28-day or 4-week cycle. In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 3 consecutive days followed by a 4-day break for the first week of a 28-day or 4-week cycle, where the number of consecutive days of treatment is decreased in at least one of the weeks of a 28-day or 4-week cycle.

In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 4 consecutive days followed by a 3-day break for the first week of a 28-day or 4-week cycle, where the number of consecutive days of treatment is increased in at least one of the weeks of the 28-day or 4-week cycle. In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered to the subject for 4 consecutive days followed by a 3-day break for the first week of a 28-day or 4-week cycle, where the number of consecutive days of treatment is decreased in at least one of the weeks of a 28-day or 4-week cycle.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) orally. In one embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered as an oral capsule. In another embodiment, the effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) is administered as an oral tablet.

In one embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) once daily (QD). In another embodiment, the dosing regimen for the cancer treatment method described in the foregoing paragraphs comprises administering an effective amount of Compound 1 (including the amorphous form and all partially crystalline or crystalline forms of the free acid Compound 1 described herein) or a pharmaceutically acceptable salt thereof (e.g. a Tris salt of Compound 1, including the amorphous form and all partially crystalline or crystalline Tris salt forms of Compound 1 disclosed herein, or the sodium salt of Compound 1) twice daily (BID).

In one embodiment, the cancer treated in the method described in foregoing two paragraphs is selected from the lists of solid tumors and hematological cancers provided herein. In one embodiment, the cancer is a non-Hodgkin lymphoma or Hodgkin lymphoma. In one particular embodiment, the treated subject belongs to a subpopulation of non-Hodgkin lymphoma or Hodgkin lymphoma patients, where the non-Hodgkin lymphoma or Hodgkin lymphoma has progressed in spite of prior treatment, and for whom additional effective (curative or life-prolonging) standard therapy is not available. In other words, the treated subject belongs to a subpopulation of resistant or refractory non-Hodgkin lymphoma or Hodgkin lymphoma. In one embodiment, the standard curative therapy is high-dose chemotherapy and autologous stem cell transplantation (HD-ASCT). In one embodiment, the subject's non-Hodgkin lymphoma or Hodgkin lymphoma has relapsed after HD-ASCT. In other words, the treated subject belongs to a subpopulation of relapsed non-Hodgkin lymphoma or Hodgkin lymphoma (e.g., HD-ASCT-relapsed). In another embodiment, the subject is not eligible for HD-ASCT. In another embodiment, the subject has refused HD-ASCT.

In one embodiment, the lymphoma in accordance with the present disclosure is:
  a) a Mature B-cell neoplasm
  b) a Mature T- and NK-cell neoplasm
  c) a Hodgkin lymphoma
  d) an Immunodeficiency-associated lymphoproliferative disorder The invention is illustrated by the following examples, which are not intended to be limiting.

EXEMPLIFICATIONS

As depicted in the Examples below, crystalline and amorphous forms are prepared according to the following general procedures.

Example 1—Abbreviations, Solutions, Instruments, Synthesis of Compound 1

Typical abbreviations used are outlined below.

TABLE 1

Abbreviations

| Name | Abbreviation |
|---|---|
| Solvents | |
| Isopropyl alcohol | IPA |
| Acetonitrile | ACN |
| Dichloromethane | DCM |
| Dimethyl Sulfoxide | DMSO |
| Ethanol | EtOH |
| Ethyl Acetate | EtOAc |
| Isopropyl Acetate | IPAc |

TABLE 1-continued

| Abbreviations | |
|---|---|
| Name | Abbreviation |
| Methanol | MeOH |
| Methyl Isobutyl Ketone | MIBK |
| Methyl tert-Butyl Ether | MTBE |
| 2-Methyltetrahydrofuran | 2-MeTHF |
| N-Methyl pyrrolidone | NMP |
| N,N-Dimethylformamide | DMF |
| tert-Butyl Methyl Ether | MtBE |
| Tetrahydrofuran | THF |
| Trichloromethane | $CHCl_3$ |
| Trifluoroacetic Acid | TFA |
| Units | |
| Celsius | C. |
| Degrees | ° |
| Equivalents | eq. |
| Gram | g |
| Hour | hr |
| Kelvin | K |
| Liters | L |
| Milligrams | mg |
| Milliliters | mL |
| Minute | min |
| Second | sec |
| volume | vol. |
| Watt | W |
| weight | wt. |

Solutions

FaSSGF/SGF (Fast State Simulated Gastric Fluid)

Weigh 100 mg of sodium chloride into a 50-mL volumetric flask. Add appropriate volume of purified water and sonicate until all solids are completely dissolved. Add sufficient purified water closely to the target volume and adjust to pH 1.6. Weigh 3 mg of FaSSIF/FeSSIF/FaSSGF powder into the volumetric flask and sonicate until the powder is completely dissolved. Dilute to target volume with purified water and mix well.

FaSSIF (Fast State Simulated Intestinal Fluid)

Weigh 0.170 g of monobasic sodium phosphate, 0.021 g of sodium hydroxide and 0.31 g of sodium chloride into a 50-mL volumetric flask. Add appropriate volume of purified water and sonicate until all solids are completely dissolved. Add sufficient purified water closely to the target volume and adjust to pH 6.5. Weigh 110 mg of FaSSIF/FeSSIF/FaSSGF powder into the volumetric flask and sonicate until the powder is completely dissolved. Dilute to target volume with purified water and mix well.

FeSSIF (Fed State Simulated Intestinal Fluid)

Weigh 0.41 mL of glacial acetic acid, 0.202 g of sodium hydroxide and 0.594 g of sodium chloride into a 50-mL volumetric flask. Add appropriate volume of purified water and sonicate until all solids are completely dissolved. Add sufficient purified water closely to the target volume and adjust to pH 5.0. Weigh 560 mg of FaSSIF/FeSSIF/FaSSGF powder into the volumetric flask and sonicate until the powder is completely dissolved. Dilute to target volume with purified water and mix well.

XRPD

The XRPD data were collected using PANalytical X'Pert³ X-ray powder diffractometer. Sample was spread on the middle of a zero-background Si holder. The XRPD parameters are listed in Table 2.

TABLE 2

| Parameters for XRPD | | |
|---|---|---|
| Parameters | Reflection mode | Reflection mode |
| Model | X' Pert3 | X' Pert3 |
| X-Ray wavelength | Cu, kα, Kα1 (Å): 1.540598, Kα2 (Å): 1.544426 Kα2/Kα1 intensity ratio: 0.50 | Cu, kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA |
| Divergence slit | 1/8° | 1/8° |
| Scan mode | Continuous | Continuous |
| Scan range (°2TH) | 3°-40° | 3°-40° |
| Scan step time (s) | 45.390 | 46.665 |
| Step size (°2TH) | 0.0263 | 0.0263 |
| Test time (s) | ~5 min | ~5 min |

TGA and DSC

TGA data were collected using a TA Q500/Q5000 TGA from TA Instruments and DSC was performed using a TA Q200/Q2000 DSC from TA Instruments. Detailed parameters are listed in Table 3.

TABLE 3

| Parameters for TGA and DSC | | |
|---|---|---|
| Parameters | TGA | DSC |
| Method | Ramp | Ramp |
| Sample pan | Aluminum, open | Aluminum, crimped |
| Temperature | RT - desired temperature | 25° C. - desired temperature |
| Heating rate | 10° C./min | 10° C./min |
| Purge gas | $N_2$ | $N_2$ |

DVS was measured via a SMS (Surface Measurement Systems) DVS Intrinsic. The relative humidity at 25° C. was calibrated against deliquescence point of LiCl, $Mg(NO_3)_2$ and KCl. Parameters for DVS test were listed in Table 4.

TABLE 4

| Parameters for DVS | |
|---|---|
| Parameters | DVS |
| Temperature | 25° C. |
| Sample size | 10~20 mg |
| Gas and flow rate | $N_2$, 200 mL/min |
| dm/dt | 0.002%/min |
| Min. dm/dtstabilityduration | 10 min |
| Max. equilibrium time | 180 min |
| RH range | 0% RH to 95% RH |
| RH step size | 10% RH from 0% RH to 90% RH 5% RH from 90% RH to 95% RH |

HPLC

An Agilent 1260 HPLC with DAD detector was utilized and detailed chromatographic conditions for solubility analysis are listed in Table 5.

TABLE 5

| Chromatographic conditions for solubility analysis | |
|---|---|
| Analysis Type | Solubility |
| HPLC | Agilent 1260 with DAD detector |
| Column | Kinetex 5 μm EVO C18, 150 × 4.6 mm, 5 μm |
| Mobile phase | A: 0.05% $H_3PO_4$ in $H_2O$ B: 0.05% $H_3PO_4$ in ACN |

TABLE 5-continued

| Chromatographic conditions for solubility analysis | | |
|---|---|---|
| Analysis Type | Solubility | |
| Gradient table | Time (min) | % B |
| | 0.0 | 50 |
| | 1.0 | 50 |
| | 10.0 | 80 |
| | 12.0 | 80 |
| | 12.1 | 50 |
| | 16.0 | 50 |
| Run time | 16.0 min | |
| Post time | 0.0 min | |
| Flow rate | 1.0 mL/min | |
| Injection volume | 5 μL | |
| Detector wavelength | UV at 254 nm | |
| Column temperature | 40° C. | |
| Sampler temperature | 37° C. | |
| Diluent | ACN:H$_2$O (v/v, 1:1) | |

Solution $^1$H NMR

Solution $^1$H NMR was collected on Bruker 400M NMR Spectrometer using DMSO-d6.

Synthesis of Compound 1

The synthesis of the non-crystalline Compound 1, i.e., the non-crystalline free acid was previously described in International Patent Application Publication No. WO 2014/128669 and U.S. Pat. No. 9,630,932.

Additional methods for synthesizing non-crystalline Compound 1 are described in Schemes 1 and 2.

Scheme 1
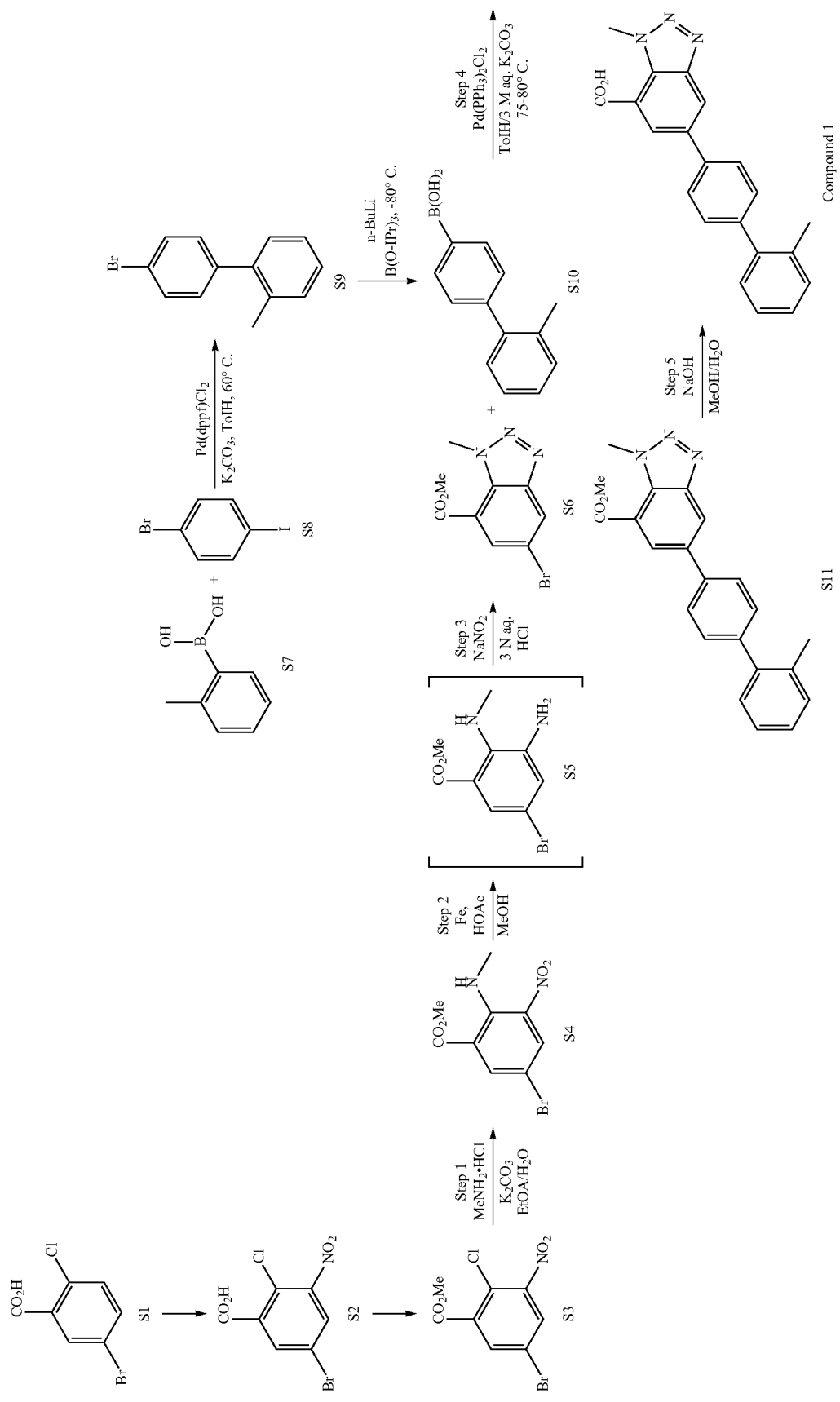

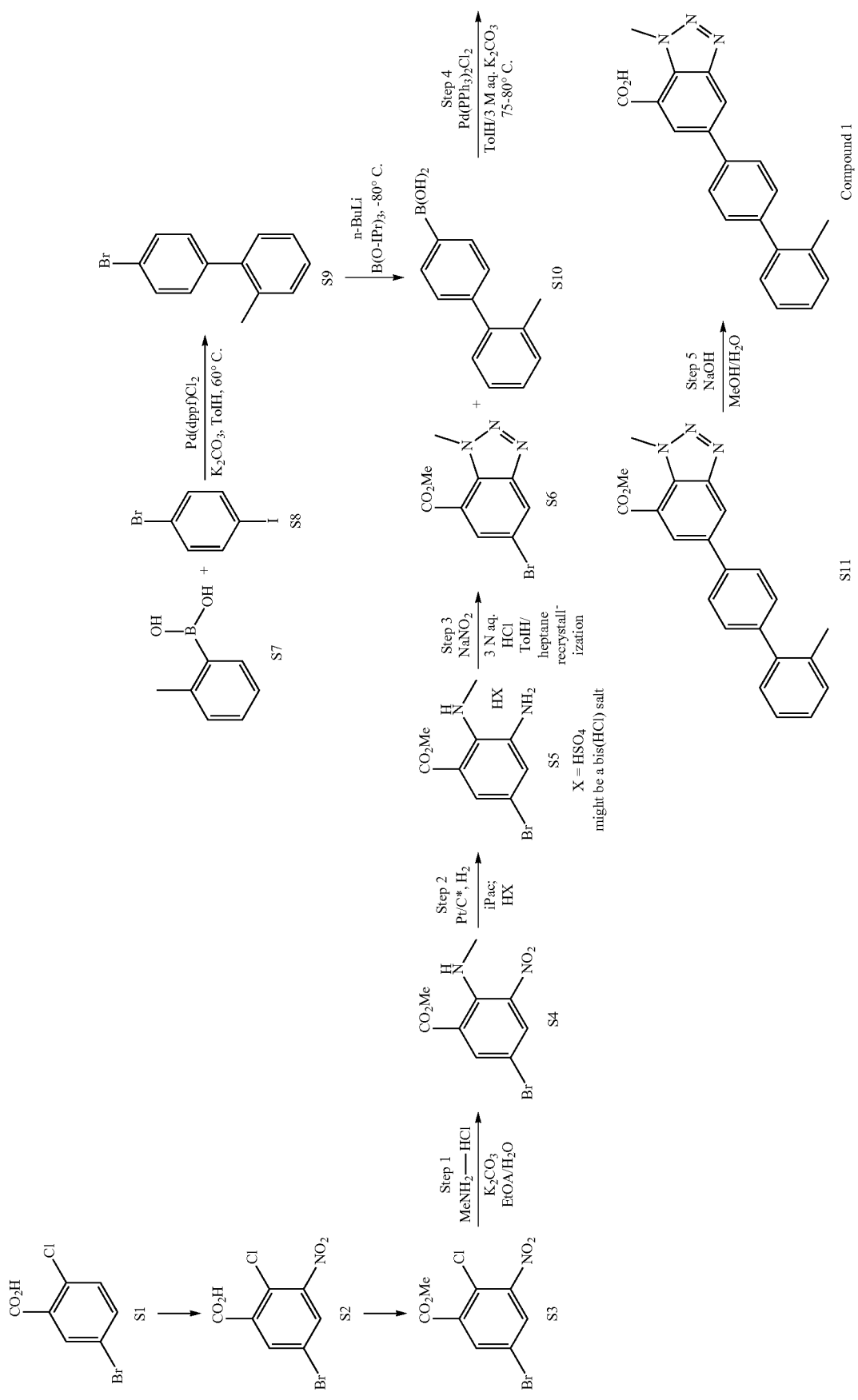

The tetra-substituted aromatic compound S3 was synthesized following earlier precedents starting with S1. See International Patent Application Publication No WO2012/142513 and Chi-Linh et al., J. Agricultural & Food Chem. 2016, 64(18) 3533, supplementary info, page S7. S3 was aminated by nucleophilic aromatic substitution of the chloride group with methylamine in the presence of aqueous base and ethyl acetate to provide S4. The nitro functionality in S4 is reduced with either iron in the presence of acid (such as acetic acid), with platinum on carbon (with or without vanadium) or with palladium on carbon. In some cases, using palladium on carbon causes de-bromination. The intermediate diamine (S5) can be used directly in the next step as shown in Scheme 1 or isolated as a salt (HCl or $H_2SO_4$) as shown in Scheme 2. S5, either as a free base or as a salt, is converted to the bromo-triazole S6 by reaction with sodium nitrite in aqueous hydrogen chloride.

In parallel, 2-methylboronic acid (S7) was coupled to 4-iodo-bromobenzene (S8) under Suzuki coupling conditions to afford biphenyl S9. The bromide in S9 was replaced with a boronic acid functionality by low-temperature lithium-halogen exchange and reaction with tri-isopropyl-borate (S10).

A solution of the bromo triazole (S6) and the boronic acid (S10) in toluene were coupled under Pd-catalyzed conditions in the presence of aqueous potassium carbonate (Suzuki coupling) to yield S11. The methyl ester in S11 was hydrolyzed to the carboxylic acid with aqueous sodium hydroxide in methanol to yield the free acid form of Compound 1.

Example 2—Amorphous Solid Dispersion of Compound 1

Compound 1 and Hypromellose Acetate Succinate-MG (Hypromellose Acetate Succinate, MG grade, Shin-Etsu Chemical Co.) (HPMCAS) (50%/50%, w/w) are weighed and dissolved in methanol and spray-dried on a Buchi B-290 to produce an amorphous Compound 1 and hypromellose acetate succinate (HPMCAS) solid dispersion. Spray drying processing parameters include nitrogen as the drying gas, an inlet temperature of about 80° C. to 95° C., an outlet temperature of about 37° C. to 45° C., spray solution concentration of about 15% w/w. The amorphous solid dispersion is further dried in a vacuum oven for 12 to 18 hours at 40° C. and then screened. The amorphous solid dispersion may be packaged in double polyethylene bags with twisted nylon tie and placed in a high density polyethylene (HDPE) container containing desiccant and stored at 2-8° C. until the next step of processing.

Example 3—Polymorph and Salt Screening of Compound 1

Polymorph Screening

A total of 74 polymorph screening experiments were conducted with different solution crystallization and solid transition methods, as listed in Table 6. Solids isolated were characterized using XRPD, TGA and DSC (see Table 7) and the pattern comparison results in FIG. 2 showed that four different crystal forms were obtained.

TABLE 6

Summary of polymorph screening experiments of free acid Compound 1

| Methods | Amount of Experiments | Identified solid forms |
|---|---|---|
| Anti-solvent addition | 10 | Free acid Form C |
| Slow evaporation | 3 | Free acid Form C |
| Slow cooling | 5 | Free acid Form C |
| Slurry at RT | 20 | Free acid Form A/B/C/D |
| Slurry at 50° C. | 10 | Free acid Form B/C/D |
| Solid vapor diffusion | 10 | Free acid Form A/C |
| Liquid vapor diffusion | 7 | Free acid Form A/C |
| Polymer-induced crystallization | 6 | Free acid Form C |
| Manual grinding | 3 | Free acid Form A |
| Total | 74 | Free acid Form A/B/C/D |

TABLE 7

Summary of solid-state characterization of free acid Form A/B/C/D

| Crystal form | Weight loss in TGA (wt %) | Thermal event in DSC (onset temperature, ° C.) | Identification |
|---|---|---|---|
| Freeform Type A | 1.0 | 212.1**, 326.8 | Anhydrous form |
| Freeform Type B | 2.9 | 321.9 | Anhydrous form |
| Freeform Type C | 3.6* | 322.5 | Anhydrous form |
| Freeform Type D | 1.0 | 286.7, 327.4 | Anhydrous form |

*By heating treatment to 150° C. for freeform Type C, no solid form change with reduced weight loss of 2.3% was observed.
**Exothermal peak, peak temperature.

Characterization of Identified Crystalline Forms of Free Acid Compound 1

Representative sample of each identified form (Form A/B/C/D) was characterized using TGA and DSC. Heating experiments were also carried out to study the relationship among different forms.

Free Acid Form A

The XRPD pattern of free acid Form A is shown in FIG. 2A, with the list of peaks shown in FIG. 2B. TGA/DSC curves in FIG. 3C indicated a weight loss of 1.0% up to 200° C. and a weak exotherm at 212.1° C. (peak temp) before the sharp endotherm at 326.8° C. (onset temp). Heating treatment showed no form change for free acid Form A after heating to 150° C. and then cooling to ambient conditions. Form A converted to Form B after heating to 220° C. Based on the low TGA weight loss and heating experiment results, freeform Type A was postulated to be an anhydrous form.

Free Acid Form B

Free acid Form B can be obtained by heating experiments and slurry at RT/50° C. Free acid Form B was obtained by heating the free acid Form A starting material to 220° C. and then cooling to ambient conditions, and the XRPD pattern is shown in FIG. 3A, with the peak list shown in FIG. 3B and TGA/DSC curves in FIG. 3C indicated a weight loss of 2.9% up to 200° C. and a single sharp endotherm at 321.9° C. (onset temp). Combining the prepared method (transformation from anhydrous free acid Form A) and the neat TGA/DSC curves, free acid Form B was postulated to be a hygroscopic anhydrous form.

Free Acid Form C

Free acid Form C can be obtained by anti-solvent addition, evaporation, slow cooling and slurry etc. Free acid Form C was obtained by slurrying the starting material Compound 1 in 1,4-dioxane at RT for ~2 days, and the XRPD pattern is shown in FIG. 4A, and the corresponding peak list is provided in FIG. 4B. TGA/DSC curves in FIG.

4C indicated a weight loss of 3.6% up to 200° C. and a single sharp endotherm at 322.5° C. (onset temp). Heating treatment showed no form change for free acid Form C after heating to 150° C., and it converted to Form B after heating to 300° C. TGA characterization was further performed for the heated free acid Form C and decrease of TGA weight loss (from 3.6% to 2.3% up to 200° C.) was observed. Based on the TGA/DSC and heating experiment results, free acid Form C was postulated to be a hygroscopic anhydrous form.

Free Acid Form D

Free acid Form D can be obtained by slurry in multiple solvent systems. Free acid Form D was obtained by slurry the starting material Compound 1 in EtOAc at RT for ~7 days, and the XRPD pattern was shown in FIG. 5A, with the corresponding peak list shown in FIG. 5B. TGA/DSC curves in FIG. 5C indicated a weight loss of 1.0% up to 200° C. and a weak endotherm at 286.7° C. (onset temp) before a sharp endotherm at 327.4° C. (onset temp). Heating treatment showed free acid Form D converted to Form B after heating to 305° C. Based on the low TGA weight loss and heating experiment results, free acid Form D was postulated to be an anhydrous form.

Thermodynamic Stability Study

To investigate and compare the thermodynamic stability among the identified four crystalline forms of Compound 1 (free acid Form A/B/C/D), two stages of slurry competition experiments were conducted, of which the first one was to study the anhydrous solvent systems and the second stage was solvent systems with different water activities ($a_w$).

In the first stage, ~2 mg of each solid form (free acid Form A/B/C/D) was physically mixed first, followed by addition of 0.5 mL solvent to form suspension. At various slurrying conditions, a small amount of solid was isolated after ~7 days for XRPD test. By XRPD characterization, free acid Form A/B/C converted to Form D after slurry at RT, 50° C. and 70° C., indicating that Form D is more stable than Form A/B/C between RT and 70° C. thermodynamically.

To further explore any impact of water content on the conversion relationship, six conditions with different water activities and temperatures were applied. Approximately 2 mg of each solid form (free acid Form A/B/C/D) was mixed and suspended in 1.0 mL corresponding solvent systems. After slurry for ~1 month, the solids were isolated for XRPD test. By XRPD characterization, free acid Form A/B/C converted to Form D after slurry at RT, 50° C. and 70° C., indicating that Form D is more stable than Form A/B/C in solvent mixtures with different water activities ($a_w$: 0~1).

Salt Screening

Solvent-mediated reaction crystallization was applied for the salt screening. A total of 55 salt screening experiments were conducted, including 10 counterions and five different solvents, as well as five blank experiments. The specific experimental procedures were described as following:

1. Weigh ~15 mg freeform Type A and molar equivalent of counter-ions into each HPLC vial;
2. Add 0.5~1.0 mL corresponding solvent to form suspension or solution;
3. Stir the mixtures magnetically (~1000 rpm) at RT (25±3° C.) for ~2 days;
4. Isolate remaining solids by centrifugation (10000 rpm, 2 mins);
5. Characterize solids by XRPD after drying at 50° C. for ~2 hours.

As summarized in Table 8, 12 potential salt hits were identified, including five Na salt hits (Type A-E), three Ca salt hits (Type A-C), one Mg salt hit (Type A), two Tris salt hits (Forms A and B) and one betaine salt hit (Type A) (highlighted in bold print in Table 8). Solid-state characterization of the identified salt hits is described in Table 9.

TABLE 8

Summary of salt screening results for Compound 1

| No. | Counter ion | A EtOH | B acetone | C THF | D 1,4-dioxane | E ACN/water (9/1, v/v) |
|---|---|---|---|---|---|---|
| 1 | NaOH | Na salt Type B* (Clear) | Na salt Type C* (Clear) | Na salt Type D* (Clear) | freeform Type A + D* (Clear) | Na salt Type E* (Clear) |
| 2 | Ca(OH)$_2$ | Ca salt Type A | Ca salt Type A | Ca salt Type A | Ca salt Type B | Ca salt Type C |
| 3 | Mg(OH)$_2$ | freeform Type C + Mg(OH)$_2$ | freeform Type C + Mg(OH)$_2$ | Mg salt Type A | Mg salt Type B + Mg(OH)2 | Mg salt Type A |
| 4 | NH$_4$OH | freeform Type B + C | freeform Type B | freeform Type C* | freeform Type B | free acid Form B |
| 5 | tris | tris salt Form B | tris salt Form A | tris salt Form A | tris salt Form A | free acid Form C |
| 6 | arginine | amorphous* | weak crystallinity (amorphous) | amorphous* | weak crystallinity (amorphous) | amorphous* |
| 7 | lysine | freeform Type A | freeform Type A | freeform Type C | freeform Type A | free acid Form C |
| 8 | choline | freeform Type B + C | freeform Type C | freeform Type C | freeform Type C | free acid Form B |
| 9 | betaine | freeform Type B + C | freeform Type B + C | betaine salt Type A | betaine salt Type A | free acid Form B |
| 10 | meglumine | amorphous* | freeform Type C | amorphous* | freeform Type C | amorphous* |
| 11 | blank | freeform Type B + C | freeform Type B + C | freeform Type B + C | freeform Type C | free acid Form B + C |

*Clear solution was obtained after slurry at RT or 5° C., followed by transferring to evaporate at RT to isolate any solid.

TABLE 9

Summary of characterization of different potential salt hits

| Salt hits | Weight loss in TGA (wt %) | Thermal event in DSC (peak temp., ° C.) |
|---|---|---|
| Na salt Type A** | 10.2%, up to 150° C. | 113.9 |
| Na salt Type B | 10.3%, up to 150° C. | 84.6, 110.8, 143.5 |
| Na salt Type C | N/A | N/A |
| Na salt Type D | N/A | N/A |
| Na salt Type E | 22.1%, up to 200° C. | 113.7 |
| Ca salt Type A | 10.2, up to 200° C. | 94.5, 153.8, 199.4, 231.5 |
| Ca salt Type B | N/A | N/A |
| Ca salt Type C | N/A | N/A |
| Mg salt Type A | 8.7, up to 200° C. | 120.8, 214.0 |
| Tris salt Form A[1] | 1.0, up to 150° C. | 196.3* |

TABLE 9-continued

Summary of characterization of different potential salt hits

| Salt hits | Weight loss in TGA (wt %) | Thermal event in DSC (peak temp., ° C.) |
|---|---|---|
| Tris salt Form A[2] | 2.8, up to 150° C. | 202.0 (see FIG. 7C) |
| Tris salt Form B | 10.8, up to 190° C. | 129.9, 205.8 (see FIG. 8C) |
| Tris salt Form C | 1.2, up to 150° C. | 196.9 (see FIG. 9C) |
| Betaine salt Type A | 9.1, up to 100° C. | 124.2 |

[1]This Tris salt Form A was prepared as a ~15 mg batch during salt screening using the procedure described above.
[2]This Tris salt Form A was re-prepared as a ~200.7 mg batch.
*Onset temperature.
**Na salt Type A was obtained by humidity-induced transformation for amorphous Na salt.
N/A: Since weak crystallinity was observed for the isolated solids, no more characterization was performed.

Example 4—Polymorph Screening and Characterization of Tris Salt Form A, Tris Salt Form B and Tris Salt Form C of Compound 1

Polymorph Screening

Figure 6:
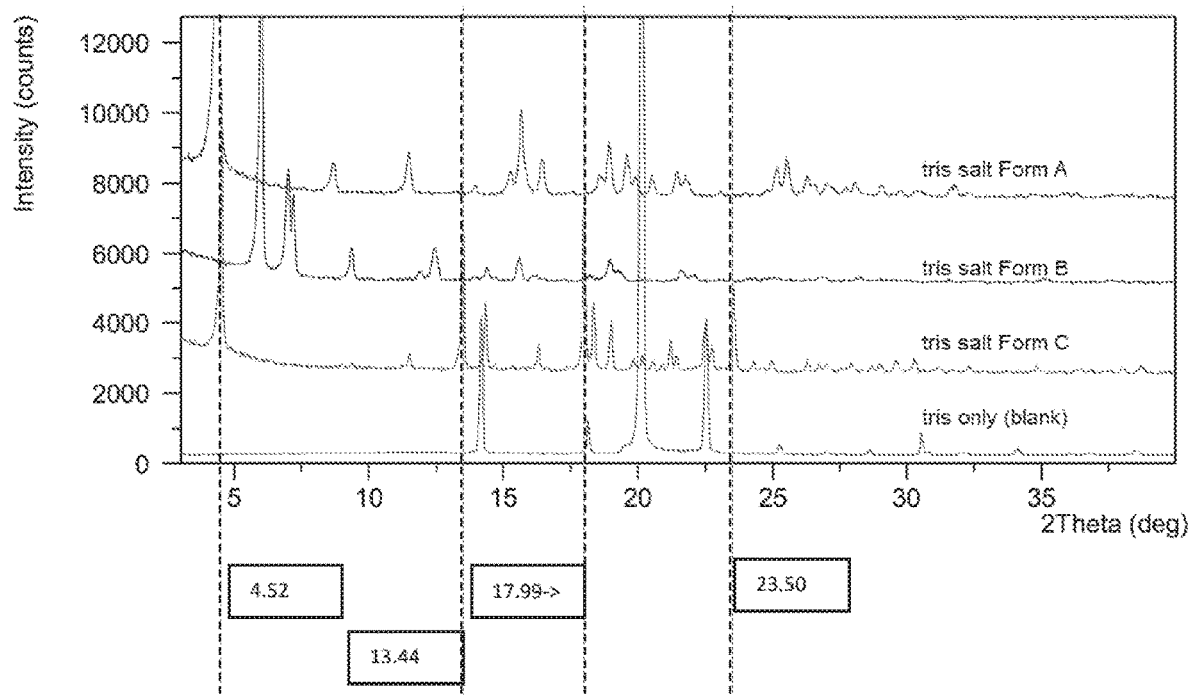
FIG. 6 depicts an overlay of X-ray powder diffraction (XRPD) pattern for 3 crystalline forms of the tris(hydroxymethyl)aminomethane (Tris) salt of Compound 1.

A total of 107 polymorph screening experiments were conducted using 11 solution crystallization or solid transition methods and using a Tris salt form of Compound 1 and a free acid form of Compound 1, as listed in Table 10. A total of 105 experiments isolated solids for XRPD characterization. No new form was obtained for the free acid in addition to the crystalline free acid Forms A/B/C/D that had been identified in Example 3. A new crystalline Form C was obtained for the Tris salt, in addition to the crystalline Tris salt Forms A/B that had been identified in Example 3. Solids isolated were characterized using XRPD, TGA and DSC (see Table 9) and the pattern comparison results in FIG. 6 showed that three different crystal forms were obtained.

TABLE 10

Summary of polymorph screening experiments of free acid Compound 1 and Tris salt of Compound 1

| Methods | Starting Material | No. of Experiments | Obtained Solid Forms |
|---|---|---|---|
| Anti-solvent addition | Tris Salt | 18 | Tris Salt Form A/C; Tris Salt Form A + C; Tris Salt Form C+ Free acid Form C/D; Free acid Form C |
| Reverse anti-solvent addition | Tris Salt | 10 | Tris Salt Form C; Tris Salt Form C+ Free acid Form C; Free acid Form C |
| Solid-vapor diffusion | Tris Salt | 9 | Tris Salt Form C |
| Liquid-vapor diffusion | Tris Salt | 12 | Tris Salt Form B/C; Tris Salt Form A + C; Tris Salt Form C+ Free acid Form C; Free acid Form B + C; |
| Slow evaporation | Tris Salt | 8 | Tris Salt Form A/B/C Free acid Form B/C |
| Slow cooling | Tris Salt | 8 | Tris Salt Form A Tris Salt Form A/C+ Free acid Form C; Tris Salt Form A + C+ Free acid Form C Free acid Form C |
| Slurry at RT (25 ± 3° C.) | Tris Salt | 20 | Tris Salt Form C; Tris Salt Form C+ Free acid Form B/D; |
| Slurry at 50° C. | Tris Salt | 12 | Tris Salt Form C; Tris Salt Form C+ Free acid Form B/D; |
| Polymer induced crystallization | Tris Salt | 4 | Tris Salt Form A; Tris Salt Form B + C; Freeform Form C; Freeform Form B + C |
| Reactive crystallization | Free Acid; Tris Salt | 4 | Tris Salt Form C; Tris Salt Form C + Free acid Form D |
| Solvothermal | Free Acid; Tris Salt | 2 | Tris Salt Form C Tris Salt Form C+ Free acid Form B/D |
| Total | / | 107 | Tris Salt Form A/B/C Free acid Form B/C/D |

Characterization of Identified Crystalline Forms of Tris Salt Compound 1

A representative sample of each identified form (Form A/B/C) was characterized using XRPD, TGA and DSC. Heating experiments were also carried out to study the relationship among different forms.

Tris Salt Form A

Figure 7D:
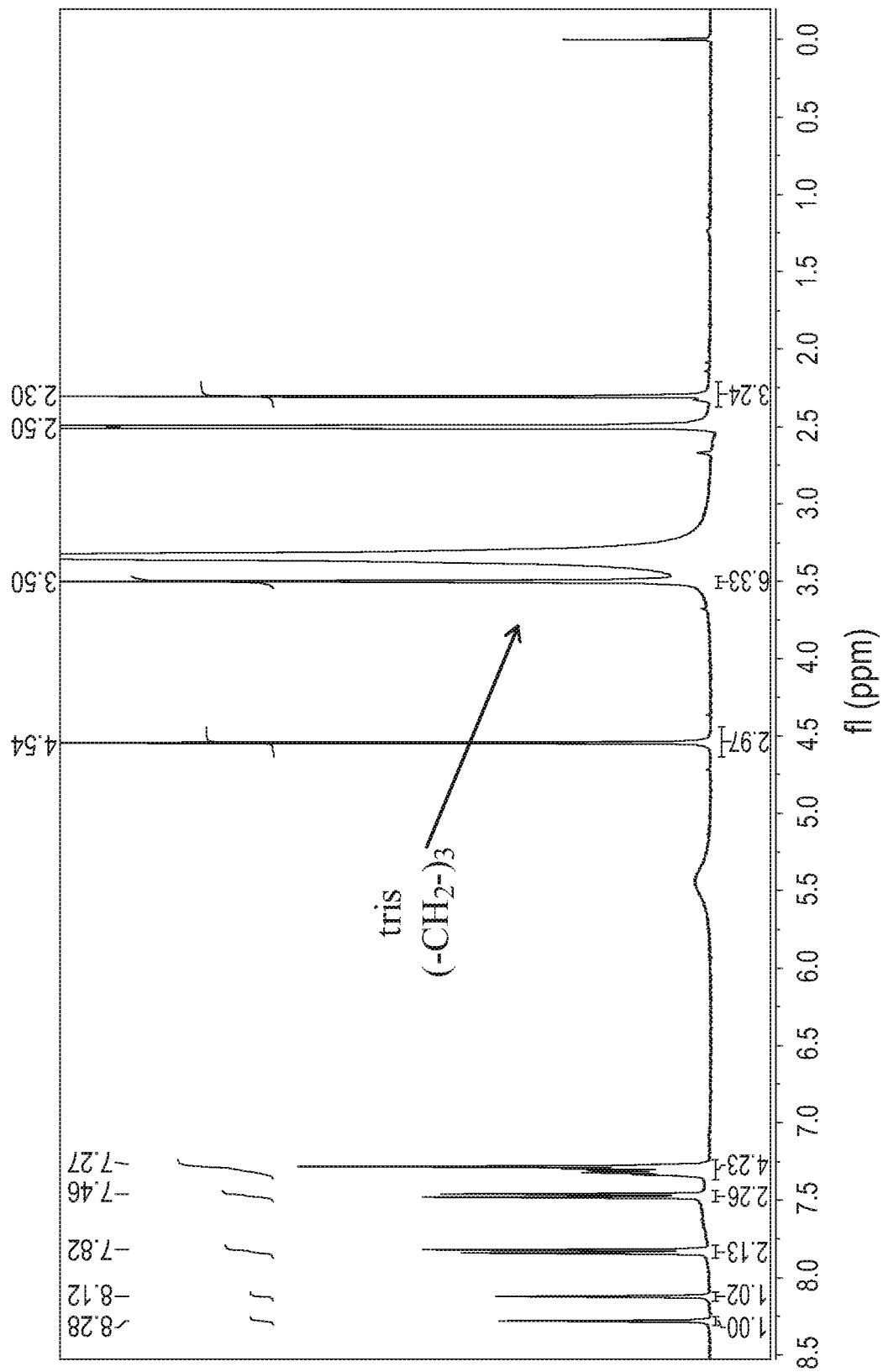
FIG. 7D depicts the $^1$H NMR pattern for the crystalline Form A of the Tris salt of Compound 1.

Tris salt Form A was obtained by slurrying the free acid Form A with Tris in acetone at RT for ~2 days. XRPD pattern is shown in FIG. 7A, with the corresponding peak list shown in FIG. 7B. TGA/DSC curves in FIG. 7C indicated a weight loss of 2.8% up to 150° C. and a sharp endotherm at 198.6° C. (onset temp.). Based on the $^1$H NMR results in FIG. 7D, the stoichiometry of Tris salt Form A was determined to be 1.0:1.1 (Free acid/Tris).

Tris Salt Form B

Figure 8C:
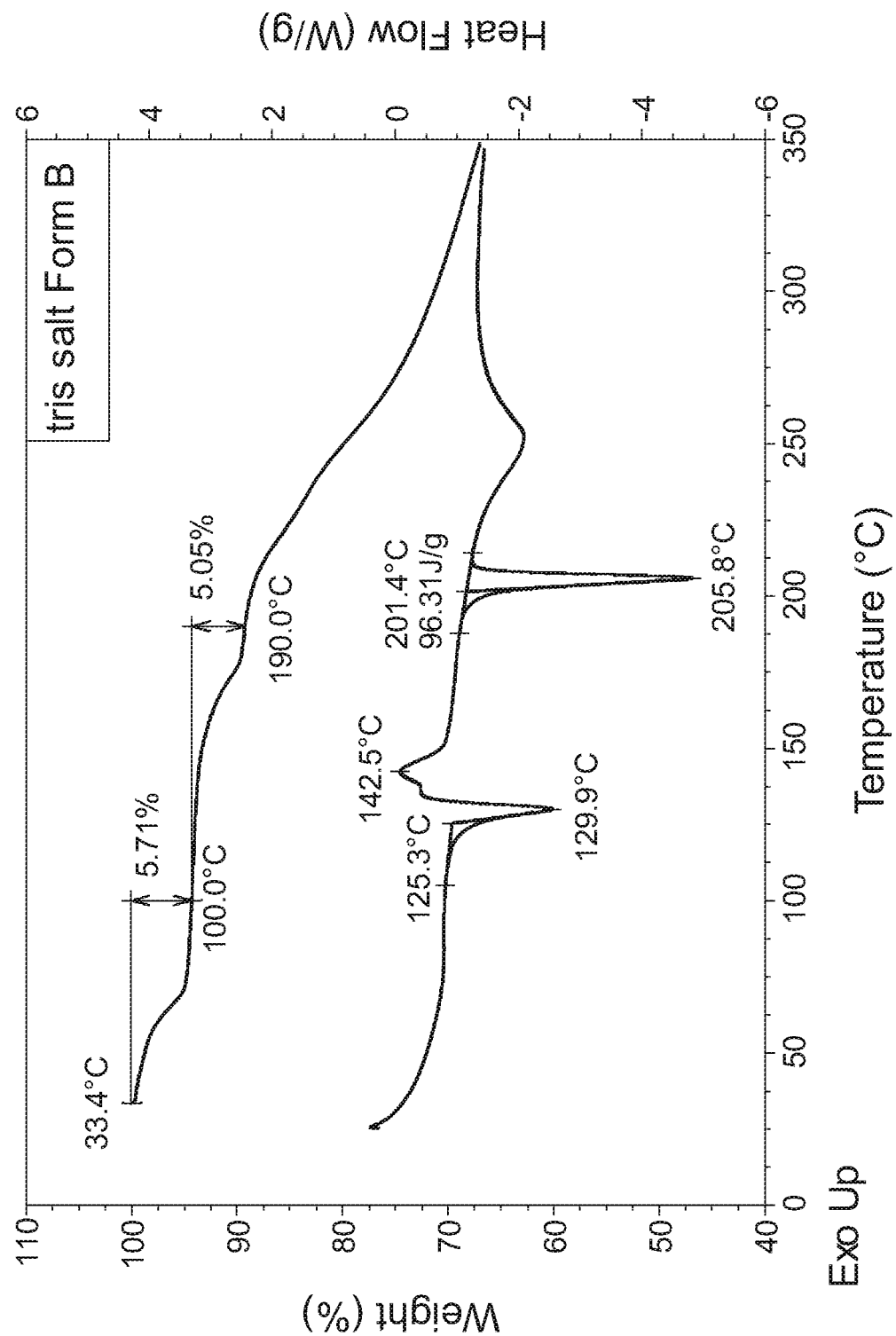
FIG. 8C depicts the combined DSC thermogram and TGA thermogram for the crystalline Form B of the Tris salt of Compound 1.
Figure 8D:
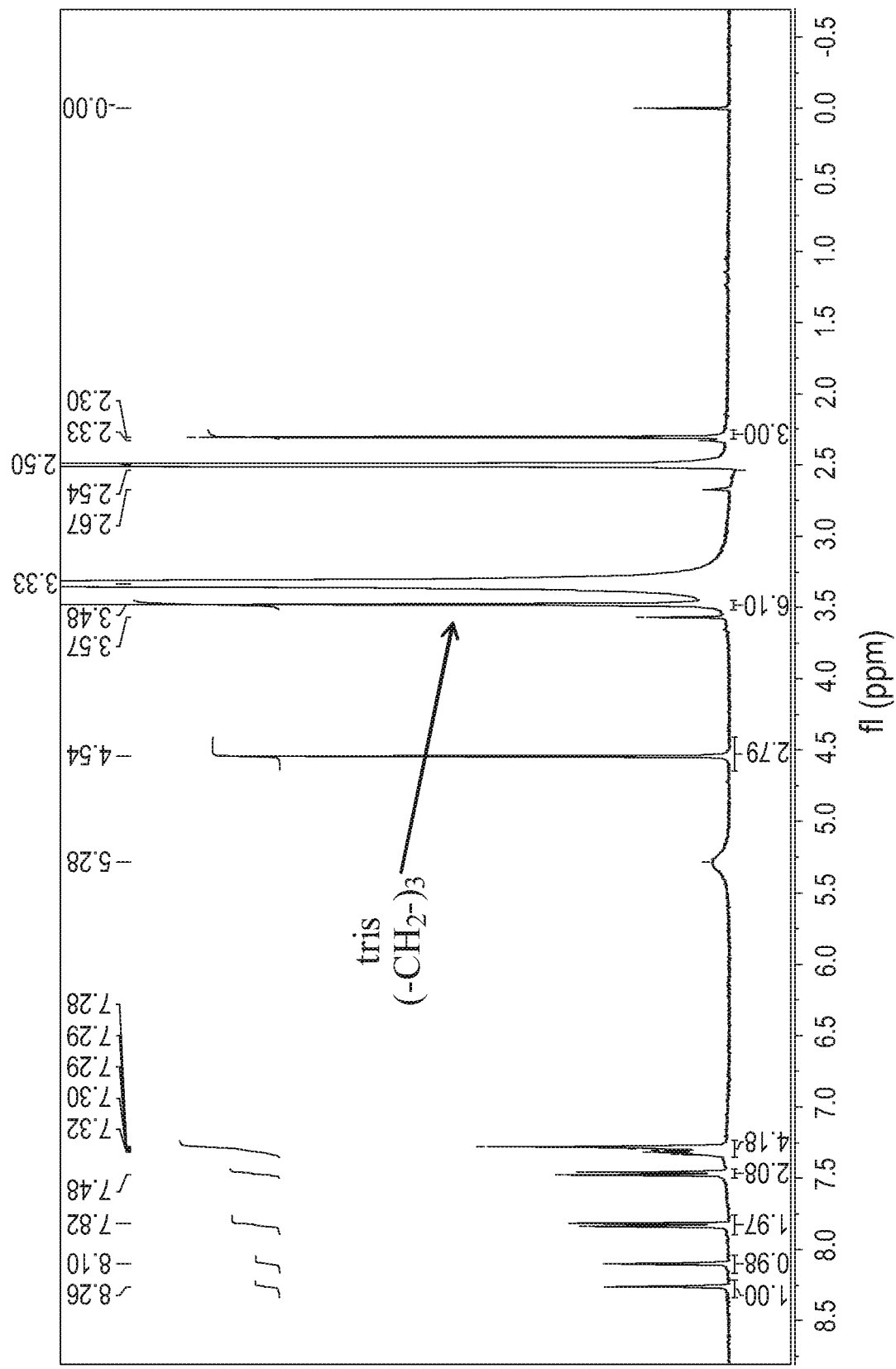
FIG. 8D depicts the $^1$H NMR pattern for the crystalline Form B of the Tris salt of Compound 1.

Tris salt Form B was obtained by slurrying the free acid Form A with Tris in EtOH at RT for ~2 days. XRPD pattern is shown in FIG. 8A, with the corresponding peak list shown in FIG. 8B. TGA/DSC curves in FIG. 8C showed a two-step weight loss of 10.8% up to 190° C. and an overlapped endo-/exotherm at 125.3° C. (onset temp.) before a sharp endotherm at 201.4° C. (onset temp.). Tris salt Form B converted to Tris salt Form A after heating to 150° C. followed by cooling to ambient conditions. Based on the $^1$H NMR results in FIG. 8D, the stoichiometry of tris salt Type B was determined to be 1.0:1.0 (Free acid/Tris).

Tris Salt Form C

Tris salt Form C was obtained by slurrying the free acid form of Compound 1 with Tris in DMSO at RT for ~2 days. The resulting slurry was heated to 100° C. and stirred for 30 min, after which the reaction became a clear solution. The reaction solution was then cooled to RT, and no solids were formed at RT. 320 mL EtOH was then slowly added to the reaction solution then stirred for 30 min at RT. This step was repeated. After the second EtOH addition and stirring, the solids were formed. The reaction mixture containing the formed solids was stirred overnight at 20-25° C., then filtered. The filtrate cake was washed with 2×320 mL EtOH and dried in vacuum at 50° C. to obtain a white solid. Next, 150 mL of EtOH was added to the white solid and the slurry was mechanically stirred at 65° C. for 4 hr. The reaction solution was left to cool to RT for about an hour and stirred at RT for 3 hr, then filtered. The filtrate cake was washed with 2×32 mL EtOH and dried in vacuum at 50° C. for 20 hr to obtain 29.8 g of off-white or white powder. Next, 150 mL of EtOH was added to the white solid and the slurry was mechanically stirred at 65° C. for 4 hr. As a further and final purification step, the obtained off-white/white powder was re-dissolved in DMSO (45 mL) at 100° C. for over 15 min. The solution was then cooled to 45° C., then EtOH (500 mL) was added dropwise. The reaction mixture started to become cloudy after adding 150 mL of the EtOH. The resulting slurry was stirred for 20 h at 25-30° C., then filtered. The filtrate cake was washed with 2×100 mL EtOH. The resulting Tris salt was triturated for 5 hr at 70° C. in 20 vol. EtOH, then cooled to 25-30° C. for over 2 hr and stirred at the same temperature for 3 hr. This procedure was repeated three times before 28 g of Tris salt Form C was obtained as an off-white solid. The XRPD pattern of Tris salt Form C is shown in FIG. 9A, with the corresponding peak list shown in FIG. 9B. TGA/DSC curves in FIG. 9C indicated a weight loss of 1.2% up to 150° C. and a sharp endotherm at 193.1° C. (onset temp.) with a peak at 196.9° C. The stoichiometry was confirmed to be 1.00:1.02 (Free acid/Tris) by $^1$H NMR (data not shown).

Additional procedures that may be used to obtain Tris salt Form C are described below. Four grams of the free acid form of Compound 1 was slurried with 1.5 g Tris in 10 mL DMSO at RT. The reaction solution was cooled to about 30° C. and 20 mL EtOH was added. 10 mg of Tris salt Form A was charged and stirred for 5 min. to form a cloudy solution. The mixture was stirred for 2 hr and diluted with 60 mL of EtOH to form a slurry. The slurry was stirred at 28-32° C. overnight. Solid was collected by filtration, washed with 2×20 mL EtOH and dried to yield Tris salt Form C as an off-white solid.

The free acid form of Compound 1 and 1.05 eq. of Tris were mixed in 2.5 vol. of DMSO in a flask. The mixture was heated to ~100° C. and stir for 0.5 to 1 hr to form clear solution. The solution was cooled to 60-70° C. and diluted slowly with additional volumes of EtOH (can range from 5-15 vol.). Seeds of Tris salt Form C were added, followed by charging slowly an additional volume of EtOH (can range from 5-15 vol.) over 2 hours. The mixture was stirred for 16-24 hr at 60-70° C. and cooled to 20-30° C. The mixture was stirred at 20-30° C. for 2-4 hr. Solid was collected by filtration, washed with EtOH, and dried at 40-50° C. for 8-12 hr under vacuum to yield Tris salt Form C as an off-white solid.

Example 5—Thermodynamic Stability Studies Comparing Tris Salt Form A and Tris Salt Form C The thermodynamic stability relationship between Tris salt Forms A and C was investigated via slurry competition experiments in 2 process related solvent systems, DMSO/EtOH (1:8, v/v) and EtOH at 4 temperature conditions (5° C./RT/50° C./75° C.). Two stages of slurry competition experiments were conducted, of which the first stage included temperature as a variable and the second stage used newly opened reagents to minimize the effect of absorbed moisture. Typical experimental procedures are described below.

About 5-10 mg of crystalline Tris salt Form C was first dissolved in ~1.0 mL of corresponding solvent to form nearly saturated solution under corresponding temperature (equilibrating method: stirring magnetically, ~1000 rpm, ~2 hrs). Then ~15 mg of each form (crystalline Tris salt Forms A and C) was physically mixed, followed by addition of the nearly saturated solution to form a suspension. The suspensions were then stirred (~1000 rpm) under corresponding temperature for 7 days (a small amount of solids were sampled at 2 day point in the second stage experiments). The obtained solids were isolated via centrifugation (10000 rpm, 2 mins) and tested by XRPD to confirm the form.

Tris salt Form A was shown to have converted to Tris salt Form C, indicating that Tris salt Form C was thermodynamically more stable between 5° C. and 50° C.

Example 6—Kinetic Solubility Studies Comparing Free Acid Form D, Tris Salt Form A and Tris Salt Form C Kinetic solubility of Tris salt Form A and free acid Form D were measured in three bio-relevant media (SGF, FaSSIF and FeSSIF) at 37° C. In details, ~30 mg solids were suspended into 4.0 mL of each medium initially and equilibrated via shaking (500 rpm) at 37° C. Approximately 0.8 mL suspension was extracted at each time point of 15/30/60/120 mins and 24 hrs. The supernatant and precipitate were separated by centrifugation (10000 rpm, ~3 mins) followed by concentration (HPLC) and pH measurement for supernatant and the corresponding solid forms were characterized by XRPD.

As the data summarized in Table 11 shows, the solubility of free acid Form D was measured to be 3~8 μg/mL in FaSSIF and FeSSIF, and <1 μg/mL in SGF. Compared with free acid Form D, enhanced solubility was observed for Tris salt Form A in all SGF/FaSSIF/FeSSIF media during the equilibration (>100 μg/mL at 24 hours point). In the meantime, pH change was observed in the three media, particularly in SGF (pH: 1.8) changed to 7.4 (at 24 hrs) which may cause the solubility enhancement since this freeform exhibited acidity in water phase.

TABLE 11

Summary of kinetic solubility data of Free Acid Form D and Tris salt Form A in SGF/FaSSIF/FeSSIF

| Media | Solid (Sample ID) | Solubility (μg/mL) | | | | | pH | | | | | |
|---|---|---|---|---|---|---|---|---|---|---|---|---|
| | | 15 mins | 30 mins | 60 mins | 120 mins | 24 hrs | blank | 15 mins | 30 mins | 60 mins | 120 mins | 24 hrs |
| SGF | Free acid Form D | 0.13 | 0.11 | 0.14 | 0.13 | 0.18 | 1.8 | 2.0 | 2.1 | 2.1 | 2.1 | 2.2 |
| | Tris salt Form A | 60 | 94 | 100 | N/A | 110 | 1.8 | 6.6 | 7.2 | 7.3 | 7.4 | 7.4 |
| FaSSIF | Free acid Form D | 3.8 | 4.3 | 4.8 | 5.0 | 4.8 | 6.5 | 6.4 | 6.5 | 6.5 | 6.5 | 6.4 |
| | Tris salt Form A | 490 | 260 | 200 | 170 | 130 | 6.5 | 7.5 | 7.5 | 7.5 | 7.5 | 7.5 |
| FeSSIF | Free acid Form D | 5.6 | 7.3 | 5.9 | 7.7 | 6.4 | 5.0 | 5.0 | 5.0 | 5.0 | 5.0 | 5.0 |
| | Tris salt Form A | 160 | 200 | 290 | 81 | 120 | 5.0 | 5.4 | 5.5 | 5.5 | 5.5 | 5.5 |

Due to the thermodynamic stability of Tris salt Form C, further evaluation was conducted, including kinetic solubility in three bio-relevant media (FaSSGF/FaSSF/FeSSIF) and $H_2O$ at 37° C. The solubility of Tris salt Form C was also found to be significantly higher than the solubility of the free acid form and comparable to the Tris salt Form A in simulated intestinal media reflecting both fasting and fed conditions (FaSSIF and FeSSIF), with a gradual decline of API concentration value detected in FaSSIF/FeSSIF/$H_2O$ (FaSSIF: from 0.39 mg/mL to 0.17 mg/mL; FeSSIF: from 0.33 mg/mL to 0.04 mg/mL; $H_2O$: from 0.81 mg/mL to 0.40 mg/mL).

TABLE 12

Summary of kinetic solubility data of Tris salt Form C in SGF/FaSSIF/FeSSIF

| Media | Solubility (μg/mL)** | | | | | pH | | | | |
| --- | --- | --- | --- | --- | --- | --- | --- | --- | --- | --- |
| | 15 min | 30 min | 1 h | 2 h | 24 h | 15 min | 30 min | 1 h | 2 h | 24 h |
| FaSSGF | <LOD | <LOD | <LOD | <LOD | <LOD | 3.0 | 3.1 | 4.0 | 4.1 | 3.1 |
| FaSSIF | 390 | 320 | 250 | 220 | 170 | 7.7 | 7.8 | 7.8 | 7.8 | 7.9 |
| FeSSIF | 330* | 270* | 50 | 40 | 40 | 5.5* | 5.6* | 5.6 | 5.6 | 5.6 |
| $H_2O$ | 810 | 820 | 720 | 750 | 400 | 8.9 | 9.0 | 9.0 | 9.0 | 9.2 |

*Precipitation occurred during HPLC/pH test (samples for HPLC test were diluted to clear).

Example 7—Hygroscopicity Studies Comparing Free Acid Form D, Tris Salt Form A and Tris Salt Form C To assess the hygroscopicity of the free acid Form D, Tris Salt Form A and Tris salt Form C of Compound 1, dynamic vapor sorption (DVS) data of each sample was collected under 25° C. ~5 wt % moisture uptake was observed for both of freeform Type D and Tris salt Form A when humidity varied from 0% RH to 80% RH at 25° C. Tris salt Form C was less hygroscopic, where only ~0.04 wt % of moisture uptake was observed at the same humidity range. The solid form remained as Tris salt Form C after the DVS test, as confirmed by XRPD (data not shown).

Example 8—Pharmacokinetic Studies Comparing Free Acid and Tris Salt

The objective of the pharmacokinetic (PK) studies was to determine the pharmacokinetics of the different forms of Compound 1 in intact Sprague Dawley rats after oral (PO) administration. Briefly, several lots of Compound 1 free acid from different manufacture batches (crystallinity not tested) and having different particle size distributions and a Tris salt of Compound 1 (crystallinity not tested) were formulated with 0.5% (w/v) methylcellulose and 0.2% (v/v) Tween 80 in water at a concentration of 100 mg/mL. Food and water were available to all animals ad libitum and Compound 1 or Tris salt Form C of Compound was dosed orally at 100 mg/kg (100 mL/kg). Approximately 110 μL of whole blood was collected via tail vein bleeding predose and at 0.083, 0.25, 0.5, 1, 2, 4, 8, 12 and 24 hours postdose into tubes containing the anticoagulant $K_2EDTA$, processed to obtain plasma, and stored at approximately −70° C. until analysis. Concentrations of the active pharmaceutical ingredient in plasma samples were quantified using a nonvalidated liquid chromatography with tandem mass spectrometry (LC-MS/MS) method. Pharmacokinetic analysis of the individual plasma concentration data was performed using WinNonlin© (Version 6.4; Pharsight Corporation, Mountain View, CA, USA). Pharmacokinetic parameters were estimated using a noncompartmental extravascular models method. Area under the concentration-time curve (AUC) was calculated using the linear trapezoidal rule. For the calculation of PK parameters, concentrations of AG-636 that were below the limit of quantitation (BLQ) in the terminal phase were excluded. Concentrations that were <80% of the LLOQ were designated as BLQ.

Figure 10A:
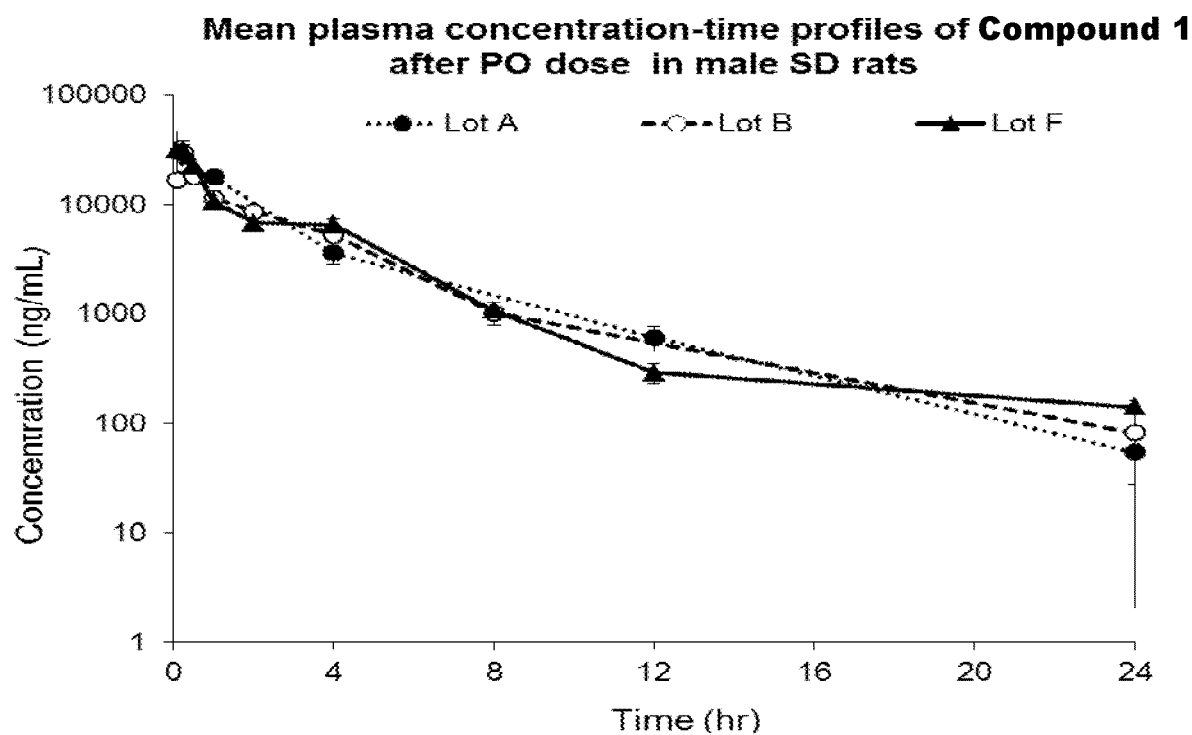
FIG. 10A depicts the pharmacokinetic (PK) profiles of free acid samples Compound 1 (Lot A and Lot B) and a Tris salt sample of Compound 1 (Lot F).
Figure 10B:
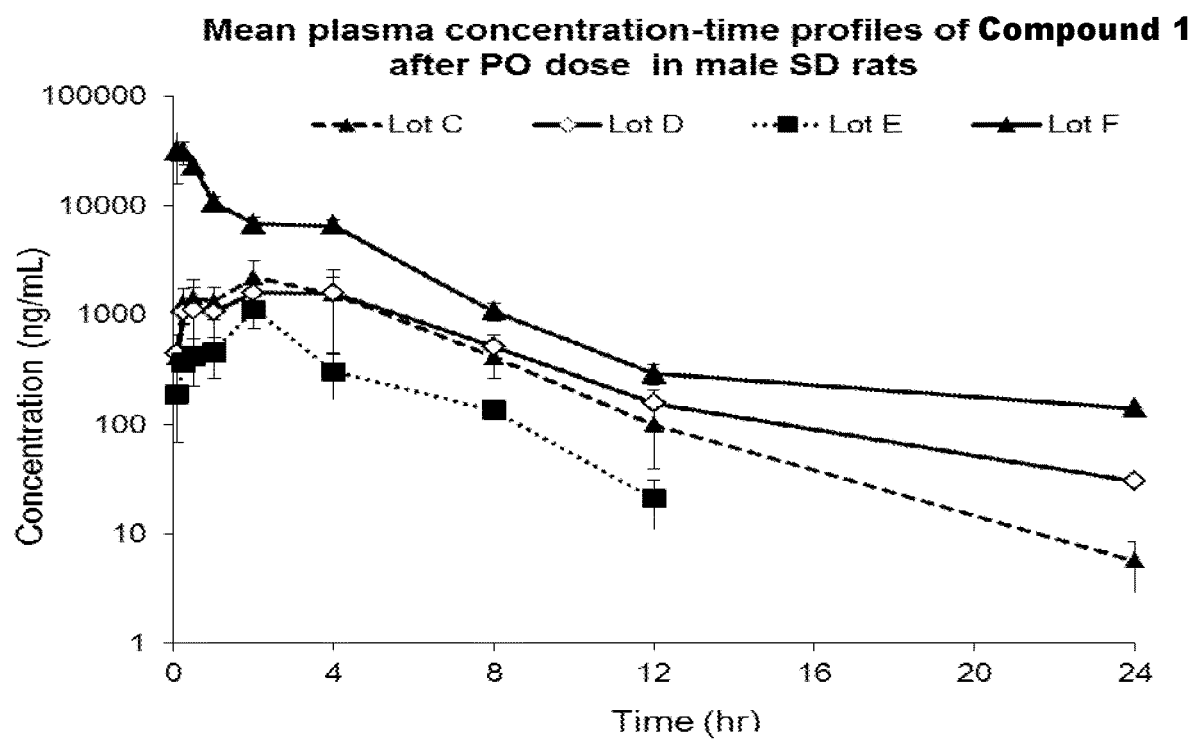
FIG. 10B depicts the pharmacokinetic (PK) profiles of free acid samples Compound 1 (Lot C, Lot D, Lot E) and a Tris salt sample of Compound 1 (Lot F).

The results from the PK experiments using the SD male rats are summarized in Tables 13 below, and the PK profile for both the Tris salt and free base of Compound 1 is shown in FIGS. 10A-10B. Among the free acid forms evaluated, Lot A and Lot B achieved some of the most elevated exposures, as can be seen in FIG. 10A. However, Lot A and Lot B were early batches of the free acid of Compound 1 that were only partially crystalline and were characterized by presence of larger amounts of residual organic solvents and therefore, not suitable for use for formulation development. Moreover, Lot A and Lot B were generated by processes not deemed suitable for large scale synthesis.

Hence, to identify a final form that would provide similar exposure as Lots A and B, a new free form of Compound 1 with better crystallinity and acceptable levels of residual solvents was synthesized with an improved process. This new free form of Compound 1 was also synthesized with different particle size distributions as Lot C, Lot D and Lot E, as summarized in Table 13, so as to evaluate the effective of particle size reduction on exposure of the free form in PK studies. Unfortunately, none of Lot C, Lot D and Lot E showed equivalent exposure previously observed, despite the enhanced crystallinity and purity (see FIG. 10B).

In sum and referring to Table 13, the $T_{max}$ and $C_{max}$ of the Tris salt of Compound 1, which respectively indicate the time at which the maximum API concentration takes place and the maximum API concentration itself, are clearly superior to the corresponding parameters observed in the free acid. Specifically, faster absorption of higher maximum API concentrations could be observed for the Tris salt compared to all batches of the free acid, as indicated with low values of $T_max$ and higher values of $C_{max}$. Significantly, even comparing the Tris salt with the best free acid batch of Lot B, the $T_{max}$ is ~2-fold lower and the $C_{max}$ is ~1.5-fold higher. Based on the in vivo PK data, it is expected that the in vitro solubility and/or rate of dissolution of the Tris salt would be significantly higher.

TABLE 13

PK parameters of free acid and Tris salt of Compound 1

| PK parameters Unit | | $T_{max}$ hr | $C_{max}$ ng/mL | $AUC_{0\ to\ 24h}$ hr*ng/mL | $AUC_{0\ to\ \infty}$ hr*ng/ml |
|---|---|---|---|---|---|
| Lot A (free acid, Batch 1) | Mean | 1.00 | 17900 | 62100 | 62300 |
| | SD | 0.00 | 1610 | 8940 | 9030 |
| | CV(%) | 0.00 | 8.96 | 14.4 | 14.5 |
| Lot B (free acid, Batch 2) | Mean | 0.25 | 29400 | 63000 | 63500 |
| | SD | 0.00 | 5370 | 559 | 871 |
| | CV(%) | 0.00 | 18.3 | 0.89 | 1.37 |
| Lot C (free acid, Batch 3, PSD: D90 ≤ 332.4 µm) | Mean | 2.17 | 2720 | 12300 | 12300 |
| | SD | 1.76 | 542 | 3930 | 3930 |
| | CV(%) | 81.0 | 19.9 | 32.1 | 32.0 |
| Lot D (free acid, Batch 4, PSD: D90 ≤ 50.9 µm) | Mean | 3.00 | 1950 | 12100 | 12300 |
| | SD | 1.73 | 195 | 2410 | 2350 |
| | CV(%) | 57.7 | 10.0 | 20.0 | 19.1 |
| Lot E (free acid, Batch 5, PSD: D90 ≤ 135.3 µm) | Mean | 2.00 | 1110 | 3740 | 3810 |
| | SD | 0.00 | 363 | 691 | 698 |
| | CV(%) | 0.00 | 32.8 | 18.5 | 18.4 |
| Lot F (Tris salt) | Mean | 0.14 | 39100 | 63300 | 64100 |
| | SD | 0.10 | 5440 | 1460 | 1130 |
| | CV(%) | 69.5 | 13.9 | 2.31 | 1.76 |

Example 9—Capsule Compositions 10 mg dose strength capsules (free-form equivalent) may be prepared as described in Table A using a dry granulation process and direct encapsulation process.

TABLE A

Batch formulation composition

| | Weighted Composition (% w/w) | |
|---|---|---|
| Component | Capsule A | Capsule B |
| Tris salt of Compound 1 | 15.9% | 15.9% |
| Diluent | 78.1% | 79.6% |
| Disintegrant | 5% | 3% |
| Lubricant | 1% | 1.5% |
| Total (%) | 100% | 100% |

50, 100, and 125 mg dose strength capsules (free-form equivalent) may be prepared as described in Table B using a dry granulation process and direct encapsulation process.

TABLE B

Batch formulation composition

| | Weighted Composition (% w/w) | |
|---|---|---|
| Component | Capsule C | Capsule D |
| Tris salt of Compound 1 | 54% | 54% |
| Diluent | 40% | 41.5% |
| Disintegrant | 5% | 3% |
| Lubricant | 1% | 1.5% |
| Total (%) | 100% | 100% |

100 and 125 mg dose strength capsules (free-form equivalent) may be prepared as described in Tables C and D using the dry granulation and direct encapsulation process described below.

TABLE C

Batch formulation composition

| | | Weighted Composition (% w/w) | | | |
|---|---|---|---|---|---|
| Component | | Capsule E | Capsule F | Capsule G | Capsule H |
| Intragranular | Tris salt of Compound 1 | 45% | 54% | 54% | 54% |
| | Diluent | 32% | 34% | 23.5% | 28% |
| | Diluent | 11% | N/A | 10% | 9% |
| | Disintegrant | 3% | 3% | 3% | 3% |
| | Binder | 5% | 5% | 8% | 2% |
| | Surfactant | 1% | 1% | 0% | 1% |
| | Glidant | 0.75% | 0.75% | 0% | 0.75% |
| | Lubricant | 0.75% | 0.75% | 0.75% | 0.75% |
| Extragranular | Glidant | 0.75% | 0.75% | 0% | 0.75% |
| | Lubricant | 0.75% | 0.75% | 0.75% | 0.75% |
| Total | | 100% | 100% | 100% | 100% |

TABLE D

Batch formulation composition

| | | Weighted Composition (% w/w) | | | | | |
|---|---|---|---|---|---|---|---|
| Component | | Capsule I | Capsule J | Capsule K | Capsule L | Capsule M | Capsule N |
| Intragranular | Tris salt of Compound 1 | 60% | 60% | 60% | 60% | 60% | 60% |
| | Diluent | 28% | 27.5% | 22% | 21.6% | 23% | 22.6% |
| | Diluent | N/A | N/A | 5.5% | 5.4% | 8% | 7.9% |
| | Disintegrant | 3% | 3% | 3% | 3% | 3% | 3% |
| | Binder | 5% | 5% | 8% | 8% | 2% | 2% |
| | Surfactant | 1% | 1% | 0% | 0% | 1% | 1% |
| | Glidant | 0.75% | 0.75% | 0% | 0% | 0.75% | 0.75% |
| | Lubricant | 0.75% | 1.5% | 0.75% | 1.5% | 0.75% | 1.5% |
| Extragranular | Glidant | 0.75% | 0.75% | 0% | 0% | 0.75% | 0.75% |
| | Lubricant | 0.75% | 0.5% | 0.75% | 0.5% | 0.75% | 0.5% |
| Total | | 100% | 100% | 100% | 100% | 100% | 100% |

The Tris salt of Compound 1 and the excipients listed in Tables C and D were weighed and sieved for blending. The Tris salt of Compound 1 and the intragranular ingredients (diluent(s), disintegrant, binder, surfactant, glidant, and lubricant) were mixed in a suitable blender. The intragranule blend was roller compacted (Capsules E, F, H, I, J, M, and N) and the compacted material was sized to produce granules. For Capsules K and L, the intragranule blend was granulated and the granulated blend was sized.

The extragranular ingredients (glidant and lubricant) were weighed and sieved for blending. The extragranular ingredients and milled granules were screened and then added to a suitable blender and blended.

The blended materials were then encapsulated into Size 1 capsules by hand filling the capsules. The capsules were stored at ambient conditions (15-25° C.).

While a number of embodiments have been described, the scope of this disclosure is to be defined by the appended claims, and not by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A tris(hydroxymethyl)aminomethane salt of a compound represented by the formula of Compound 1:

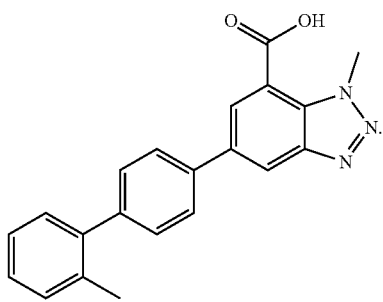 [SMILES: Cc1ccccc1-c1ccc(-c2cc(C(=O)O)c3c(c2)nnn3C)cc1]

2. The tris(hydroxymethyl)aminomethane salt of claim 1, wherein the salt is anhydrate.

3. The tris(hydroxymethyl)aminomethane salt of claim 1, wherein the salt is crystalline Form A characterized by X-ray powder diffraction peaks at 2θ angles (±0.2°) 4.4°, 15.6°, and 18.9°.

4. The tris(hydroxymethyl)aminomethane salt of claim 3, wherein the crystalline Form A is further characterized by X-ray powder diffraction peaks at 2θ angles (±0.2°) 11.5°, 16.4°, 19.6° and 25.5°.

5. The tris(hydroxymethyl)aminomethane salt of claim 3, wherein the crystalline Form A is further characterized by at least one X-ray powder diffraction peaks at 2θ angles (±0.2°) selected from 8.7°, 15.2°, 18.6°, 21.4° and 25.1°.

6. The tris(hydroxymethyl)aminomethane salt of claim 3, wherein the crystalline Form A is characterized by an X-ray powder diffraction pattern substantially similar to FIG. 7A.

7. The tris(hydroxymethyl)aminomethane salt of claim 1, wherein the crystalline form is crystalline Form B characterized by X-ray powder diffraction peaks at 2θ angles (±0.2°) 6.0°, 7.0°, and 7.2°.

8. The tris(hydroxymethyl)aminomethane salt of claim 7, wherein the crystalline Form B is further characterized by at least one X-ray powder diffraction peak at 2θ angles (±0.2°) selected from 9.3° and 12.5°.

9. The tris(hydroxymethyl)aminomethane salt of claim 7, wherein the crystalline Form B is further characterized by at least one X-ray powder diffraction peaks at 2θ angles (±0.2°) selected from 15.6° and 19.0°.

10. The tris(hydroxymethyl)aminomethane salt of claim 7, wherein the crystalline Form B is characterized by an X-ray powder diffraction pattern substantially similar to FIG. 8A.

11. The tris(hydroxymethyl)aminomethane salt of claim 1, wherein the crystalline form is crystalline Form C characterized by X-ray powder diffraction peaks at 2θ angles (±0.2°) 4.5°, 13.5°, and 18.0°.

12. The tris(hydroxymethyl)aminomethane salt of claim 11, wherein the crystalline Form C is further characterized by at least one X-ray powder diffraction peak at 2θ angles (±0.2°) selected from 14.3°, 18.3°, and 23.5°.

13. The tris(hydroxymethyl)aminomethane salt of claim 11, wherein the crystalline Form C is further characterized by at least one X-ray powder diffraction peaks at 2θ angles (±0.2°) selected from 16.3°, 19.0°, 21.2°, 22.5°, and 22.8°.

14. The tris(hydroxymethyl)aminomethane salt of claim 11, wherein the crystalline Form C is characterized by an X-ray powder diffraction pattern substantially similar to FIG. 9A.

15. A pharmaceutical composition comprising the tris(hydroxymethyl)aminomethane salt of claim 1 and one or more pharmaceutically acceptable excipients.

16. A method of treating cancer in a subject, comprising administering to the subject an effective amount of the tris(hydroxymethyl)aminomethane salt of claim 1.

17. The method of claim 16, wherein the cancer is selected from
lung cancer, breast cancer, triple negative breast cancer, melanoma, glioblastoma, prostate cancer, colon cancer, pancreatic cancer, bone cancer, cancer of the head or neck, skin cancer, cutaneous or intraocular malignant endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the kidney or ureter, carcinoma of the renal pelvis, neoplasm of the central nervous system (CNS), tumor angiogenesis, spinal axis tumor, brain stem glioma, pituitary adenoma, Kaposi's sarcoma, epidermoid cancer, squamous cell cancer, an environmentally induced cancer, and a PTEN mutant cancer; and biliary tract cancer or cancer of the ampulla of Vater, non-small cell lung cancer, bronchoalveolar carcinoma, liver cancer, cancer of the ovary, and cancer of the upper aerodigestive tract.

18. The method of claim 16, wherein the cancer is a hematological cancer selected from
acute myeloid leukemia, multiple myeloma, B-prolymphocytic leukemia, acute lymphoblastic leukemia, chronic lymphocytic leukemia, Hodgkin's disease, non-Hodgkin's lymphoma, follicular lymphoma, diffuse large B cell lymphoma, anaplastic large cell lymphoma, mantle cell lymphoma, lymphocytic lymphoma cancer of the bladder, primary CNS lymphoma, and T-cell lymphoma;

chemotherapy-resistant acute myeloid leukemia, cytarabine-resistant acute myeloid leukemia, acute monocytic leukemia, acute lymphoblastic leukemia, B-cell lymphoma, diffuse mixed cell lymphoma, myelodysplastic syndrome, myelodysplastic/myeloproliferative neoplasms, primary effusion lymphoma, erythroleukemia, chronic myeloid leukemia, chronic monocytic leukemia, double hit diffuse large B cell lymphoma, and triple hit diffuse large B cell lymphoma;

angioimmunoblastic lymphoma, Burkitt's lymphoma, Burkitt-like lymphoma, blastic NK-cell lymphoma, cutaneous T-cell lymphoma, lymphoblastic lymphoma, MALT lymphoma, mediastinal large B-cell lymphoma, nodal marginal zone B-cell lymphoma, small lymphocytic lymphoma, thyroid lymphoma, follicular lymphoma, Waldenstrom's macroglobulinemia, essential thrombocythemia, chronic idiopathic myelofibrosis, and polyeythemia rubra vera.

19. A method of treating cancer in a subject wherein the cancer is responsive to inhibition of dihydroorotate dehydrogenase, comprising administering to the subject an effective amount of the tris(hydroxymethyl)aminomethane salt of claim 1.

20. A method of treating a condition or a disease selected from a viral-mediated disease, transplant rejection, rheumatoid arthritis, psoriasis, an autoimmune disease, or an inflammatory disorder in a subject, comprising administering to the subject an effective amount of the tris(hydroxymethyl)aminomethane salt of claim 1.

21. A method of inhibiting growth and/or metastasis of tumor cells in a subject wherein the tumor cells are responsive to inhibition of dihydroorotate dehydrogenase, comprising administering to the subject an effective amount of the tris(hydroxymethyl)aminomethane salt of claim 1.

22. A method of inhibiting dihydroorotate dehydrogenase in a subject, comprising administering to the subject an effective amount of the tris(hydroxymethyl)aminomethane salt of claim 1.

* * * * *